US007118854B2

United States Patent
Liao et al.

(10) Patent No.: US 7,118,854 B2
(45) Date of Patent: Oct. 10, 2006

(54) PAK2: MODULATORS OF LYMPHOCYTE ACTIVATION

(75) Inventors: X. Charlene Liao, Palo Alto, CA (US); Peter Chu, San Francisco, CA (US); Jorge Pardo, San Francisco, CA (US); Congfen Li, Davis, CA (US); Haoran Zhao, Foster City, CA (US); Jun Wu, Sunnyvale, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/967,624

(22) Filed: Sep. 28, 2001

(65) Prior Publication Data

US 2002/0142325 A1   Oct. 3, 2002

Related U.S. Application Data

(60) Provisional application No. 60/280,647, filed on Mar. 30, 2001.

(51) Int. Cl.
*C12Q 1/70* (2006.01)
*C12Q 1/68* (2006.01)
*C07H 21/04* (2006.01)

(52) U.S. Cl. .............................. 435/4; 435/6; 536/23.1
(58) Field of Classification Search ............... 435/7.24, 435/4
See application file for complete search history.

(56) References Cited

FOREIGN PATENT DOCUMENTS

DK    WO 99/25347   *   5/1999
WO    WO 01/34201 A2 *   5/2001

OTHER PUBLICATIONS

Renkema et al. Current Biology, vol. 9(23) 1407-1410).*
Martin, GA et al. The EMBO J. vol. 14(9) 1970-1978 (1995).*
Rudel, T et al. Science vol. 276:1571-1574 (1997).*
Schrager et al. Proc. Natl. Acad. Sci USA, 1999. 96:8167-8172.*
Chu et al., Journal of Biology 2003, 2:21, 2101-21016.*
Renkema et al. Current Biology 1999, 9:1407-1410.*
Bagrodia et al., "PAK to the future," trends in *Cell Biology*, vol. 9, pp. 350-355, (Sep. 1999).
Bokoch et al., "Caspase-mediated activation of PAK2 during apoptosis: proteolytic kinase activation as a general mechanism of apoptotic signal transduction?," Cell Death and Differentiation, vol. 5, pp. 637-645, Stockton Press (1998).
Knaus et al., "Regulation of Human Leukocyte p21-Activated Kinases Through G Protein-Coupled Receptors," *Science*, vol. 269, pp. 221-223, (Jul. 14, 1995).
Luria et al. "Expression of the type 1 human immunodeficiency virus Hef protein in T cells prevents antigen receptor-mediated induction of interleukin 2 mRNA," Proc. Natl. Sci. USA, vol. 88, pp. 5326-5330, Medical Sciences, (Jun. 1991).
Manser et al., "Molecular Cloning of a New Member of the p21-Cdc42/Rac-activated Kinase (PAK) Family," *The Journal of Biological Chemistry*, vol. 270, No. 42, pp. 25070-25078, The American Society for Biochemistry and Molecular Biology, Inc., U.S.A., (Oct. 20, 1995).
Martin et al., "A novel serine kinase activated by rac1/CDC42Hs-dependent autophosphorylation is related to PAK65 and STE20," *The EMBO Journal*, vol. 14, No. 9, pp. 1970-1978, Oxford University Press, (1995).
M.KU et al., "A PAK1-PIX-PKL complex is activated by the T-cell receptor independent of Nck, Slp-76 and LAT," *The EMBO Journal*, vol. 20, N. 3, pp. 457-465, European Molecular Biology Organization, (2001).
Renkema et al., "Human Immunadeficiency Virus Type 1 Nef Selectively Associates with a Catalytically Active Subpopulation of p21-Activated Kinase 2 (PAK2) Independently of PAK2 Binding to Nck or β-PIX," *Journal of Virology*, vol. 75, No. 5, pp. 2154-2160, American Society for Microbiology, (Mar. 2001).
Renkema et al., "Identification of the Nef-associated kinase as p21-activated kinase 2," *Current Biology*, vol. 9, No. 23, pp. 1407-1410, Elsevier Science Ltd., (1999).
Rudel et al., "Membrane and Morphological Changes in Apoptotic Cells Regulated by Caspase-Mediated Activation of PAK2," *Science*, vol. 276, pp. 1571-1574, (Jun. 6, 1997).
Kaga et al., Activation of p21-CDC42/Rac-Activated Kinases by CO28 Signaling: p21-Actived Kinase (PAK) and MEK Kinase 1 (MEKK1) May Mediate the Interplay Between CD3 and CD28 Signals, Journal of Immunology 160:4182-4189 (1998).
Jaffer et al., "p21-Activated kinases: three more join the Pak" The International Journal of Biochemistry & Cell Biology 34:713-717 (2002).

* cited by examiner

*Primary Examiner*—James Schultz
(74) *Attorney, Agent, or Firm*—Townsend and Townsend and Crew LLP

(57) ABSTRACT

The present invention relates to regulation of lymphocyte activation. More particularly, the present invention is directed to nucleic acids encoding PAK2, which is involved in modulation of lymphocyte activation. The invention further relates to methods for identifying and using agents, including small organic molecules, peptides, circular peptides, antibodies, lipids, antisense nucleic acids, and ribozymes, that modulate lymphocyte activation via modulation of PAK2; as well as to the use of expression profiles and compositions in diagnosis and therapy related to lymphocyte activation and suppression.

12 Claims, 55 Drawing Sheets

Schematic representation of PAK proteins
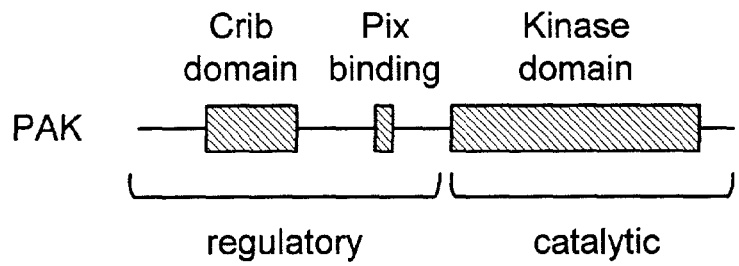
The CRIB domain contains both a p21(cdc42/Rac)-binding domain and an auto-inhibitory domain. Pix (Pak-interactive exchange factors) are members of the GEF family.
Schematic model for Cdc42/Rac activation of PAK proteins
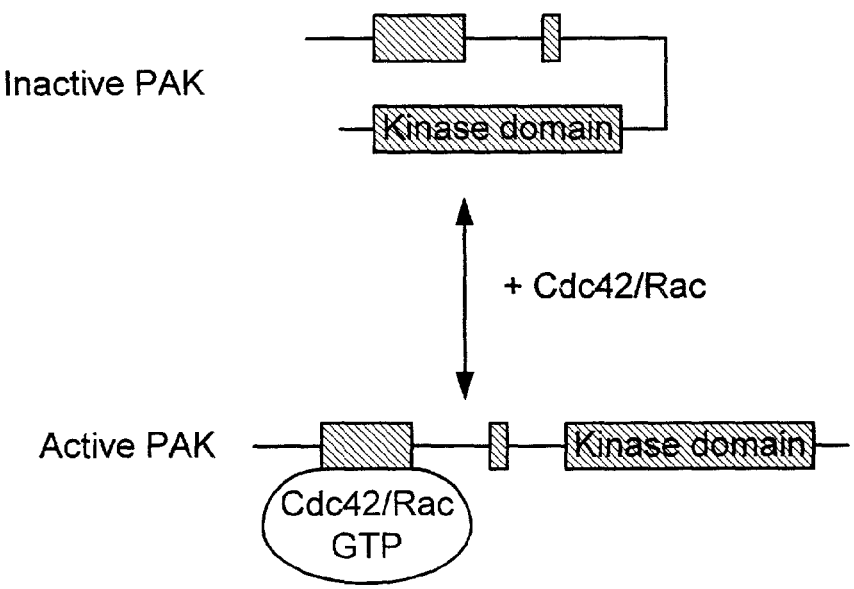
*FIG. 1.*

Figure 2

PAK2
```
LOCUS       NM_002577       2019 bp    mRNA            PRI       31-OCT-2000
DEFINITION  Homo sapiens p21 (CDKN1A)-activated kinase 2 (PAK2),
            mRNA.
ACCESSION   NM_002577
VERSION     NM_002577.1  GI:4505598
KEYWORDS    .
SOURCE      human.
  ORGANISM  Homo sapiens
            Eukaryota; Metazoa; Chordata; Craniata; Vertebrata;
            Euteleostomi; Mammalia; Eutheria; Primates; Catarrhini;
            Hominidae; Homo.
FEATURES             Location/Qualifiers
     source          1..2019
                     /organism="Homo sapiens"
                     /db_xref="taxon:9606"
                     /chromosome="3"
                     /map="3"
```

Figure 2 gene    1..2019
        /gene="PAK2"
        /note="PAK65; PAKgamma"
        /db_xref="LocusID:5062"
        /db_xref="MIM:605022"
CDS     40..1617
        /gene="PAK2"
        /EC_number="2.7.1.-"
        /note="hPAK65; novel serine kinase"
        /codon_start=1
        /db_xref="LocusID:5062"
        /db_xref="MIM:605022"
        /product="p21 (CDKN1A)-activated kinase 2"
        /protein_id="NP_002568.1"
        /db_xref="GI:4505599"

Figure 2

```
/translation="MSDNGELEDKPPAPPVRMSSTIFSTGGKDPLSANHSLK
PLPSVPEEKKPRHKIISIFSGTEKGSKKKEKERPEISPPSDFEHTIHVGFDA
VTGEFTGMPEQWARLLQTSNITKLEQKKNPQAVLDVLKFYDSNTVKQKYLSF
TPPEKDGLPSGTPALNAKGTEAPAVVTEEDDDEETAPPVIAPRPDHTKSIY
TRSVIDPVPAPVGDSHVDGAAKSLDKQKKKPKMTDEEIMEKLRTIVSIGDPK
KKYTRYEKIGQGASGTVFTATDVALGQEVAIKQINLQKQPKKELIINEILVM
KELKNPNIVNFLDSYLVGDELFVVMEYLAGGSLTDVVTETACMDEAQIAAVC
RECLQALEFLHANQVIHRDIKSDNVLLGMEGSVKLTDFGFCAQITPEQSKRS
TMVGTPYWMAPEVVTRKAYGPKVDIWSLGIMAIEMVEGEPPYLNENPLRALY
LIATNGTPELQNPEKLSPIFRDFLNRCLEMDVEKRGSAKELLQHPFLKLAKP
LSSLTPLIMAAKEAMKSNR"
``` misc_feature  259..366
              /note="PBD; Region: P21-Rho-binding domain"

misc_feature  259..441
              /note="PBD; Region: P21-Rho-binding domain"

misc_feature  784..1530
              /note="TyrKc; Region: Tyrosine kinase, catalytic domain"

Figure 2 misc_feature   784..1542
               /note="S_TKc; Region: Serine/Threonine protein
               kinases, catalytic domain"
misc_feature   784..1542
               /note="pkinase; Region: Eukarytic protein kinase
               domain"

Figure 2

BASE COUNT    615 a    413 c    481 g    510 t    SEQ ID NO:1
ORIGIN
  1 gaccttggct tgcccggggc catttcataa ttctgaatca tgtctgataa
 51 cggagaactg gaagataagc ctccagcacc tcctgtgcga atgagcagca
101 ccatctttag cactggaggc aaagaccctt tgtcagccaa tcacagtttg
151 aaaccttgc cctctgttcc agaagagaaa aagcccaggc ataaaatcat
201 ctccatattc tcaggcacag agaaaggaag taaaaagaaa gaaaaggaac
251 ggccagaaat ttctcctcca tctgattttg agcacaccat ccatgttggc
301 tttgatgctg ttactggaga attcactggc atgccagaac agtgggctcg
351 attactacag acctccaata tcaccaaact agagcaaaag aagaatcctc
401 aggctgtgct ggatgtccta aagttctacg actccaacac agtgaagcag
451 aaatatctga gctttactcc tcctgagaaa gatggccttc cttctggaac
501 gccagcactg aatgccaagg gaacagaagc acccgcagta gtgacagagg

Figure 2

```
 551 aggaggatga tgatgaagag actgctcctc ccgttattgc cccgcgaccg
 601 gatcatacga aatcaattta cacacggtct gtaattgacc ctgttcctgc
 651 accagttggt gattcacatg ttgatggtgc tgccaagtct ttagacaaac
 701 agaaaaagaa gcctaagatg acagatgaag agattatgga gaaattaaga
 751 actatcgtga gcataggtga ccctaagaaa aaatatacaa gatatgaaaa
 801 aattggacaa gggcttctg gtacagtttt cactgctact gacgttgcac
 851 tgggacagga ggttgctatc aaacaaatta attacagaa acagccaaag
 901 aaggaactga tcattaacga gattctggtg atgaaagaat tgaaaaatcc
 951 caacatcgtt aactttttgg acagttacct ggtaggagat gaattgtttg
1001 tggtcatgga atacctttgct gggggtcac tcactgatgt ggtaacagaa
1051 acagcttgca tggatgaagc acagattgct gctgtatgca gagagtgttt
1101 acaggcattg gagtttttac atgctaatca agtgatccac agagacatca
1151 aaagtgacaa tgtactttttg ggaatggaag gatctgttaa gctcactgac
1201 tttggttttct gtgcccagat caccccctgag cagagcaaaac gcagtaccat
1251 ggtcggaacg ccatactgga tggcaccaga ggtggttaca cggaaagctt
1301 atggccctaa agtcgacata tggtctctgg gtatcatggc tattgagatg
1351 gtagaaggag agcctccata cctcaatgaa aatcccttga gggccttgta
1401 cctaatagca actaatggaa ccccagaact tcagaatcca gagaactttt
1451 ccccaatatt tcgggatttc ttaaatcgat gtttggaaat ggatgtggaa
```

Figure 2

```
1501  aaaaggggtt  cagccaaaga  attattacag  catcctttcc  tgaaactggc
1551  caaaccgtta  tctagcttga  caccactgat  catggcagct  aaagaagcaa
1601  tgaagagtaa  ccgttaacat  cactgctgtg  ggctcatact  cttttttcca
1651  ttttctacaa  gaagccttt   agtatatgaa  aatgatgact  ctgttgggggg
1701  tttaagaaa   tggtctgcat  aacctgaatg  aaagaaggaa  atgactattc
1751  tctgaagaca  accaagagaa  aattggaaaa  gacaaggtat  gactttgtta
1801  tgaaccctg   cttttagggg  tccaggaagg  gatttgtggg  acttgaattc
1851  actaggctta  ggtctttcag  gaaacaggct  atcaggggca  tttatcatgt
1901  gtgagattgg  attctacttg  ggtgattgg   tggatagacc  catgaatggc
1951  ccctggggt   tttcaatctt  ggattggagg  tggggttttc  agagtgttgc
2001  cacgtctagc  tcctctccc
```

Figure 3

Alignment of PAK1, PAK2, PAK3 (PAK4 is more divergent)

```
1   MSNGLDIQDKPPAPPMRNTSTMIGVGSKDAGTLNHGSKPLPPNPEEKKK  huPAK1.pep
1   MSDNG-ELEDKPPAPPVRMSSTIFSTGGKDPLSANHSLKPLPSVPEEKKP  huPAK2.pep
1   MSD-IGLDNEEKPPAPPLE-----MNSNNRDSSALNHSSKPLPMAPEEKNK  huPAK3.pep 51  KDEFYRSILPG--DKTNKKKEKERPEISLPSDFEHTIHVGFDAVTGEFTG  huPAK1.pep
50  RHKII-SIFSGT-EKGSKKKEKERPEISLPSDFEHTIHVGFDAVTGEFTG  huPAK2.pep
45  KABL-RSIFPGGGDKTNKKKEKERPEISLPSDFEHTIHVGFDAVTGEFTG  huPAK3.pep 99  MPEQWARLLQTSNITKSEQKKNPQAVLDVLEFYNSKKTSNSQKYMSFT--  huPAK1.pep
98  MPEQWARLLQTSNITKLEQKKNPQAVLDVLKFYDSNTV--KQKYLSFTPP  huPAK2.pep
94  IPEQWARLLQTSNITKLEQKKNPQAVLDVLKFYDSKETVNNQKYMSFTSG  huPAK3.pep 147 DKSAEDYNSSNALNVKAVSETPAVPPVSEDEDDDD----DDATPPPVIAP  huPAK1.pep
146 EKDGLP-SGTPALNAKGTEAPAVVT--------EEEDDDEITAPPVIAP   huPAK2.pep
144 DKSAHGVIAAHPSSTKTASEPPLAPPVSEEDEEREEEDENEPPPVIAP    huPAK3.pep 193 RPEHTKSVYTRSVIEPLEVTPTRDVATSPISPTENNTTPPDATRNTEKQ   huPAK1.pep
186 RPDHTKSIYTRSVDDPVE-----------APVGDSHVDGAA--KSLDKQ   huPAK2.pep
194 RPEHTKSIYTRSVVESI---ASPAVPNKEVTPSAENANSSTIYRNTDRQ   huPAK3.pep 243 KKKPKMSDEEILEKLRSIVSVGDPKKKYTRFEKIGQGASGTVYTAMDVAT  huPAK1.pep
222 KKKPKMTDEEIMEKLRTIVSLGDPKKKYTRMEKIGQGASGTVETATDVAL  huPAK2.pep
241 RLKNSKMTDEEILEKLRSIVSVGDPKKKYTRFEKIGQGASGTVYTALDIAT huPAK3.pep 293 GQEVAIKQMNLQQQPKKELIINEILVMRENKNPNIVNYLDSYLVGDELWV  huPAK1.pep
272 GQEVAIKQINLQKQPKKELIINEILVMKELKNPNIVNELDSYLVGDELFV  huPAK2.pep
291 GQEVAIKQMNLQQQPKKELIINEILVMRENKNPNIVNYLDSYLVGDELWV  huPAK3.pep 343 VMEYLAGGSLTDVVTET-CMDEGQIAAVCRECLQALEFLHSNQVIHRDIK  huPAK1.pep
322 VMEYLAGGSLTDVVTETACMDEAQIAAVCRECLQALEFLHANQVIHRDIK  huPAK2.pep
341 VMEYLAGGSLTDVVTET-CMDEGQIAAVCRECLQALDFLHSNQVIHRDIK  huPAK3.pep 392 SDNILLGMDGSVKLTDFGFCAQITPEQSKRSTMVGTPYWMAPEVVTRKAY  huPAK1.pep
372 SDNVLLGMEGSVKLTDFGFCAQITPEQSKRSTMVGTPYWMAPEVVTRKAY  huPAK2.pep
390 SDNILLGMDGSVKLTDFGFCAQITPEQSKRSTMVGTPYWMAPEVVTRKAY  huPAK3.pep 442 GPKVDIWSLGIMAIEMIEGEPPYLNENPLRALYLIATNGTPELQNPEKLS  huPAK1.pep
422 GPKVDIWSLGIMAIEMVEGEPPYLNENPLRALYLIATNGTPELQNPEKLS  huPAK2.pep
440 GPKVDIWSLGIMAIEMVEGEPPYLNENPLRALYLIATNGTPELQNPERLS  huPAK3.pep 492 AIFRDFLNRCLDMDVEKRGSAKELLQHQFLKIAKPLSSLTPLIAAKEAT   huPAK1.pep
472 PIFRDFLNRCLEMDVEKRGSAKELLQHPFLKLAKPLSSLTPLIMAAKEAM  huPAK2.pep
490 AVFRDFLNRCLEMDVDRRGSAKELLQHPFLKLAKPLSSLTPLTIAAKEAI  huPAK3.pep 542 KNN-H.  huPAK1.pep
522 KSN-R.  huPAK2.pep
540 KNSSR.  huPAK3.pep
```

Decoration 'Decoration #1': Box residues that match the Consensus exactly.

```
PAK2 FEATURES      Location/Qualifiers
     Protein       1..525
                   /product="p21 (CDKN1A)-activated kinase 2"
                   /EC_number="2.7.1.-"
                   /note="hPAK65; novel serine kinase"
     Region        74..134
                   /region_name="P21-Rho-binding domain"
                   /db_xref="CDD:pfam00786"
                   /note="PBD"
     Region        249..501
                   /region_name="Eukaryotic protein kinase domain"
                   /db_xref="CDD:pfam00069"
                   /note="pkinase"
```

Figure 4A
Phenotypic Assays in Jurkat Cells
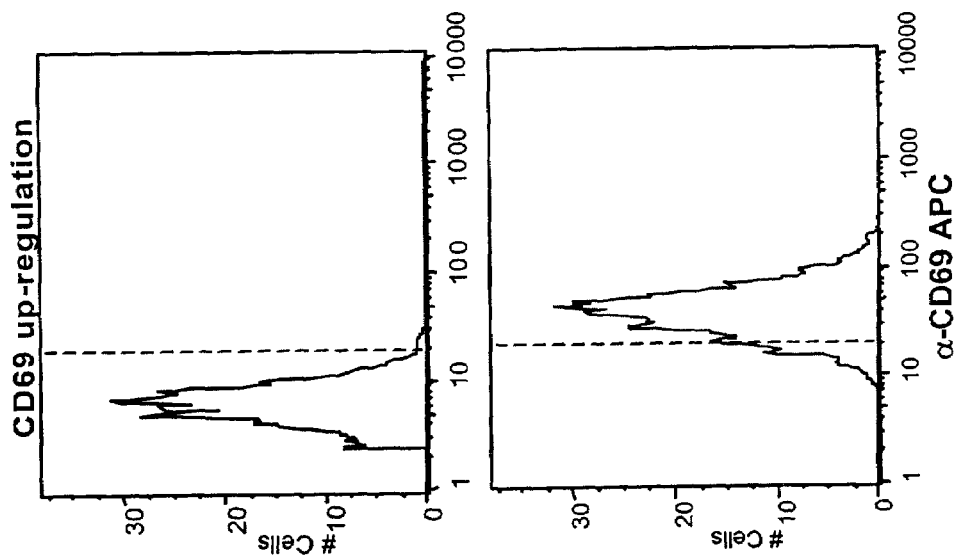
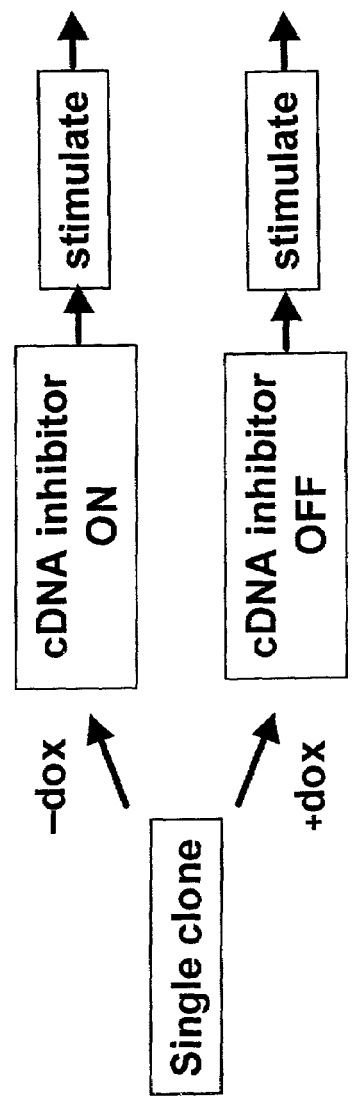

Identification of Inhibitory Hits

An original Dox-regulatable clone from the CD69 screen in Jurkat cells

The cDNA insert encodes a truncated form of PAK2

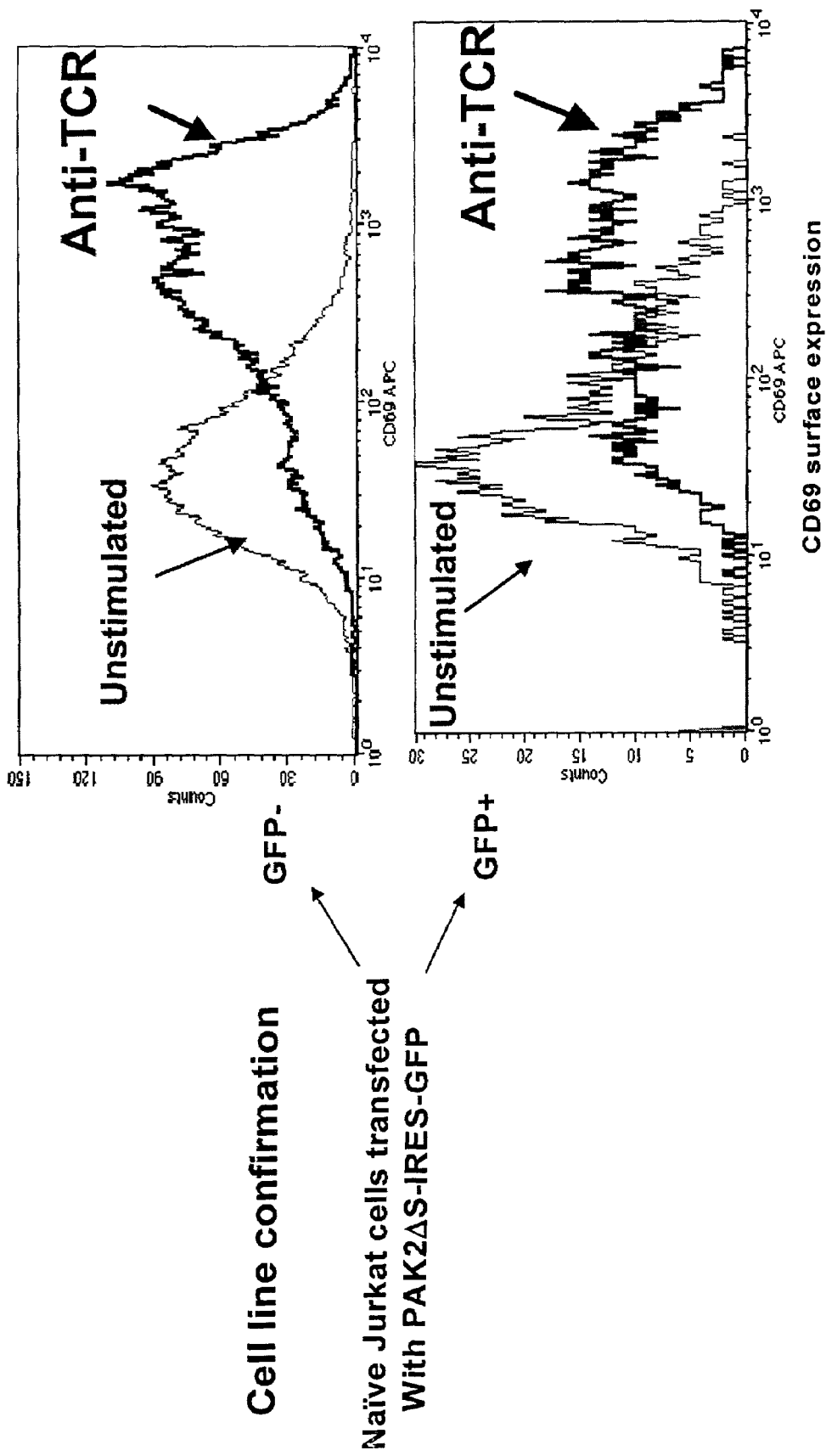

Successful Phenotype Transfer of PAK2 ΔL

Naïve Jurkat N cells infected with PAK2ΔL-IRES-GFP

Following TCR Stimulation

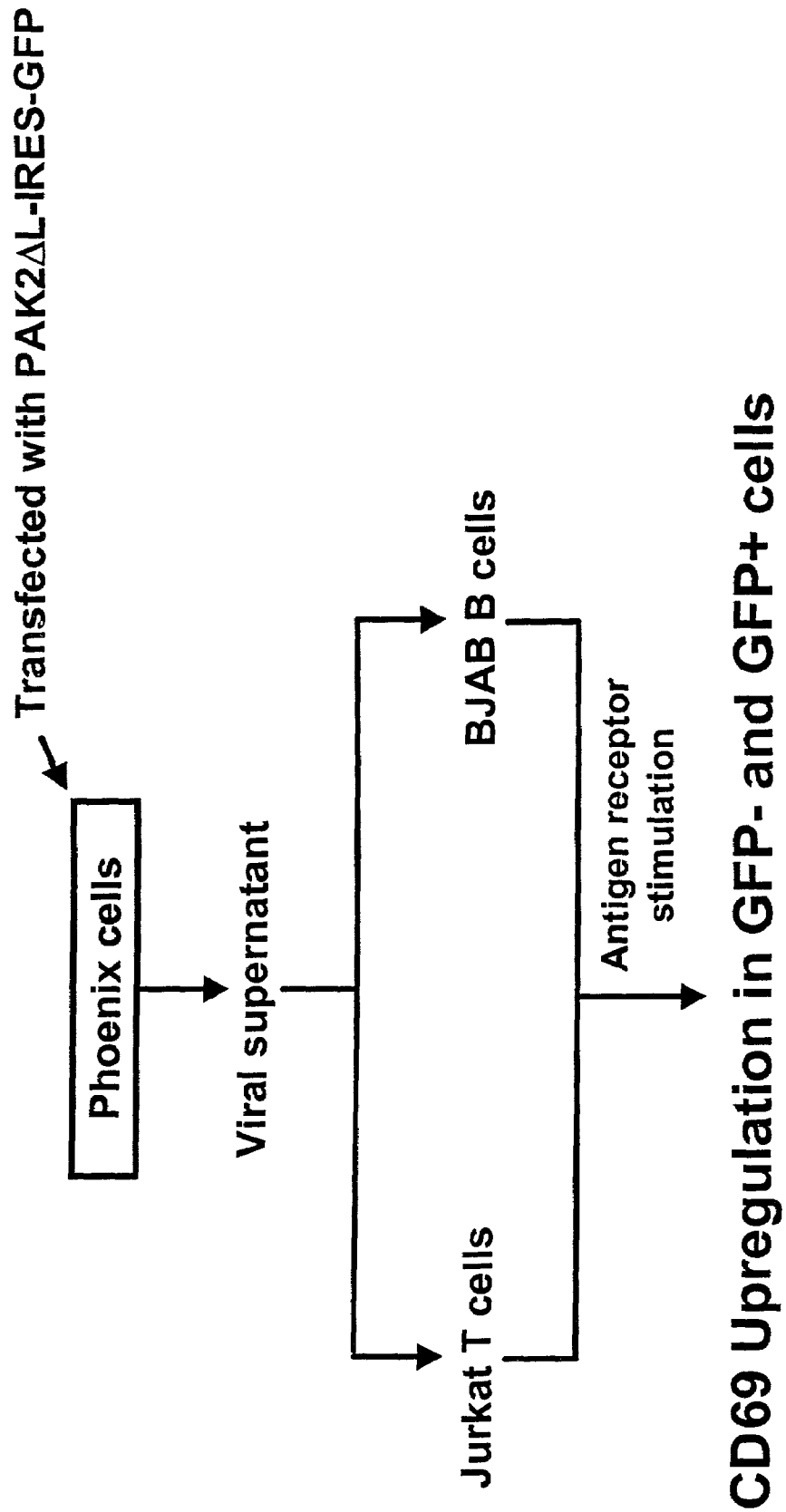

DN-Syk Inhibits Both TCR and BCR Signaling

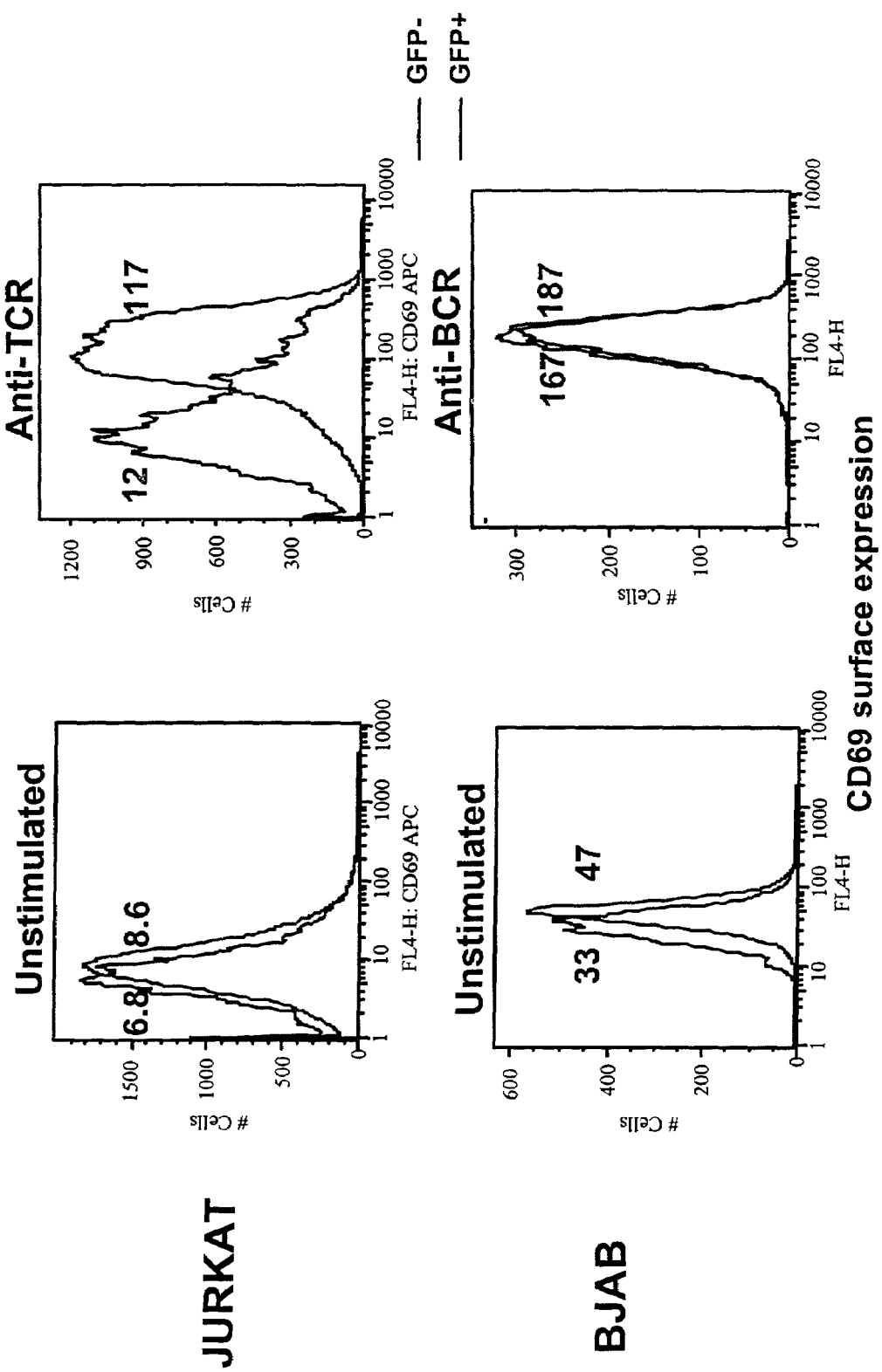

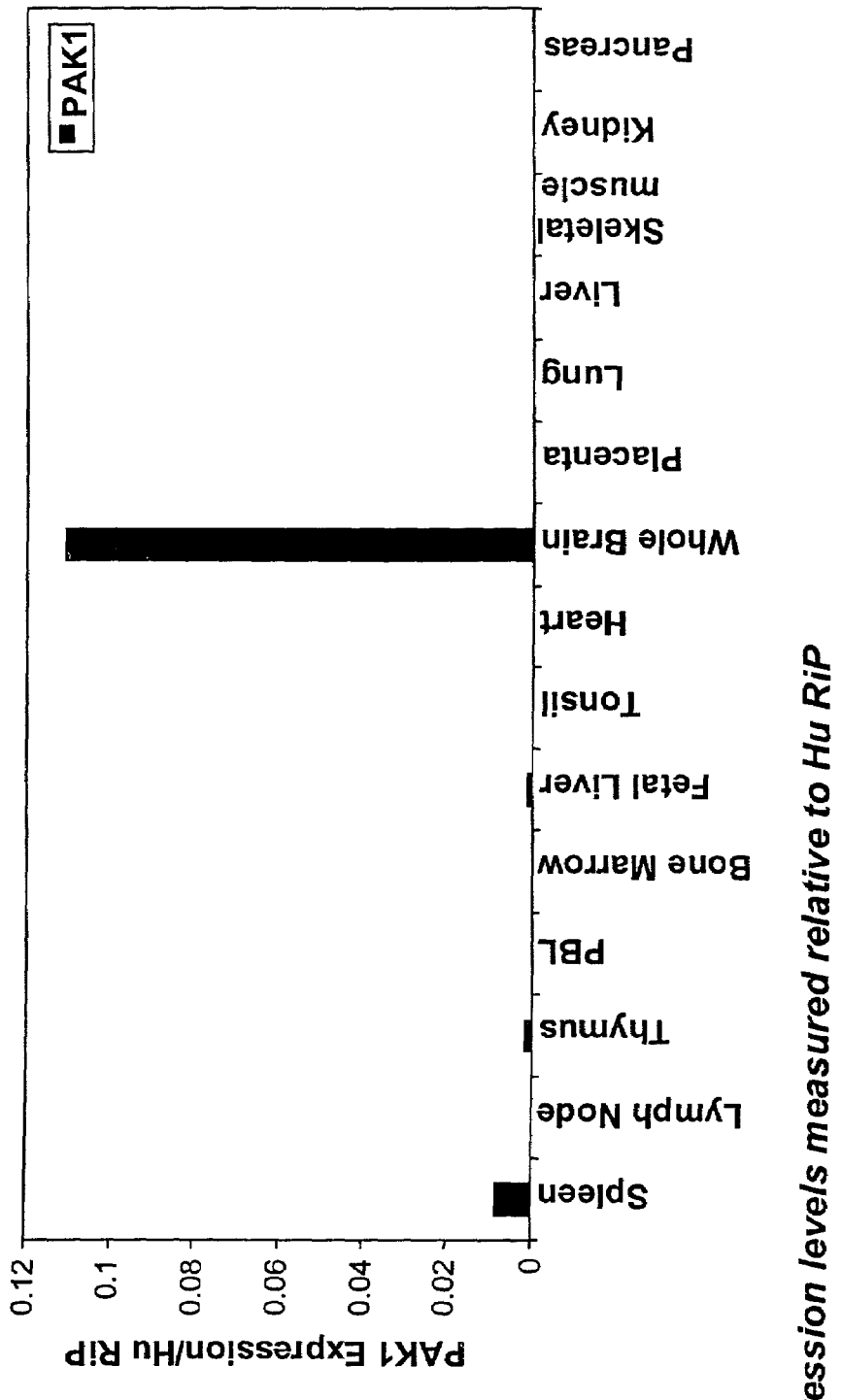

The Relative Level of PAK2 Message in Various Human Cell Lines and Cell Populations

*Expression levels measured relative to Hu RiP*

Anti-CD3 alone was not Sufficient to Induce IL-2 Secretion

Wild-type & Kinase-inactive PAK2

A Transient Overexpression Assay to Examine the TCR-induced CD69 Upregulation

CD69 Upregulation in GFP- and GFP+ cells

Graphical Summary of PAK2 Inhibition of CD69

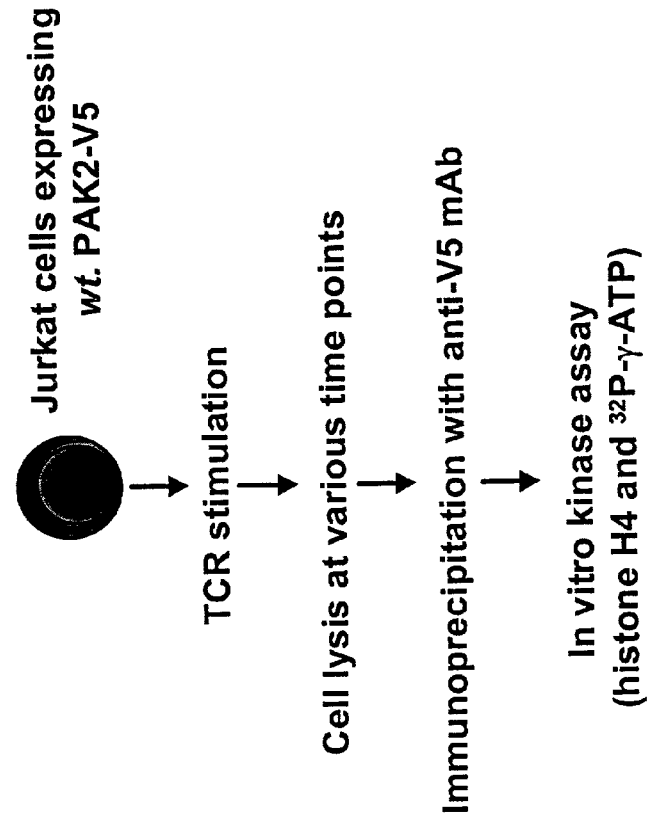

TCR Stimulates PAK2 Kinase Activity

Figure 18

PAK2 full-length

GI "4505598" [GenBank]

LOCUS       NM_002577  2019 bp  mRNA  PRI  31-OCT-2000
DEFINITION  Homo sapiens p21 (CDKN1A)-activated kinase 2 (PAK2),
            mRNA.
ACCESSION   NM_002577
VERSION     NM_002577.1  GI:4505598

ORIGIN
        1 gaccttggct tgcccggggc catttcataa ttctgaatca tgtctgataa
       51 cggagaactg gaagataagc ctccagcacc tcctgtgcga atgagcagca
      101 ccatctttag cactggaggc aaagaccctt tgtcagccaa tcacagtttg
      151 aaacctttgc cctctgttcc agaagagaaa aagcccaggc ataaaatcat
      201 ctccatattc tcaggcacag agaaaggaag taaaaagaaa gaaaaggaac
      251 ggccagaaat ttcctctcca tctgattttg agcacaccat ccatgttggc
      301 tttgatgctg ttactggaga attcactggc atgccagaac agtgggctcg
      351 attactacag acctccaata tcaccaaact agagcaaaag aagaatcctc

Figure 18

```
 401 aggctgtgct ggatgtccta aagttctacg actccaacac agtgaagcag
 451 aaatatctga gctttactcc tcctgagaaa gatggccttc cttctggaac
 501 gccagcactg aatgccaagg gaacagaagc acccgcagta gtgacagagg
 551 aggaggatga tgatgaagag actgctcctc ccgttattgc cccgcgaccg
 601 gatcatacga aatcaattta cacacggtct gtaattgacc ctgttcctgc
 651 accagttggt gattcacatg ttgatggtgc tgccaagtct ttagacaaac
 701 agaaaaagaa gcctaagatg acagatgaag agattatgga gaaattaaga
 751 actatcgtga gcataggtga ccctaagaaa aaatatacaa gatatgaaaa
 801 aattggacaa gggcttctg gtacagtttt cactgctact gacgttgcac
 851 tgggacagga ggttgctatc aaacaaatta atttacagaa acagccaaag
 901 aaggaactga tcattaacga gattctggtg atgaaagaat tgaaaaatcc
 951 caacatcgtt aacttttttgg acagttacct ggtaggagat gaattgtttg
1001 tggtcatgga atacctttgct gggggtcac tcactgatgt ggtaacagaa
1051 acagcttgca tggatgaagc acagattgct gctgtatgca gagagtgttt
1101 acaggcattg gagttttttac atgctaatca agtgatccac agagacatca
1151 aaagtgacaa tgtacttttg ggaatggaag gatctgttaa gctcactgac
1201 tttggtttct gtgcccagat caccccctgag cagagcaaac gcagtaccat
1251 ggtcggaacg ccatactgga tggcaccaga ggtggttaca cggaaagctt
```

Figure 18

```
1301 atggccctaa agtcgacata tggtctctgg gtatcatggc tattgagatg
1351 gtagaaggag agcctccata cctcaatgaa aatcccttga gggcctttgta
1401 cctaatagca actaatggaa ccccagaact tcagaatcca gagaaactt
1451 ccccaatatt tcgggatttc ttaaatcgat gtttggaaat ggatgtggaa
```

Figure 18

PAK2 hit 1 (corresponding to nt 9-380 of the above sequence)
SEQ ID NO:3

```
  ct tgcccggggc catttcataa ttctgaatca tgtctgataa cggagaactg
  61 gaagataagc ctccagcacc tcctgtgcga atgagcagca ccatctttag
 111 cactggaggc aaagacccct tgtcagccaa tcacagtttg aaacctttgc
 161 cctctgttcc agaagagaaa aagcccaggc ataaaatcat ctccatattc
 211 tcaggcacag agaaaggaag taaaaagaaa gaaaaggaac ggccagaaat
 261 ttctcctcca tctgattttg agcacaccat ccatgttggc tttgatgctg
 311 ttactggaga attcactggc atgccagaac agtgggctcg attactacag
 361 acctccaata tcaccaaact
```

Figure 18

PAK2 Hit 2 (corresponds to nt 1-711 of the reference sequence)
SEQ ID NO:4

```
  1 gaccttggct tgcccggggc catttcataa ttctgaatca tgtctgataa
 51 cggagaactg gaagataagc ctccagcacc tcctgtgcga atgagcagca
101 ccatctttag cactggaggc aaagaccctt tgtcagccaa tcacagtttg
151 aaacctttgc cctctgttcc agagagaaaa aagcccaggc ataaaatcat
201 ctccatattc tcaggcacag agaaaaggaag taaaaagaaa gaaaaggaaac
251 ggccagaaat ttctcctcca tctgattttg agcacaccat ccatgttggc
301 tttgatgctg ttactggaga attcactggc atgccagaac agtgggctcg
351 attactacag acctccaata tcaccaaact agagcaaaag aagaatcctc
401 aggctgtgct ggatgtccta aagttctacg actccaacac agtgaagcag
451 aaatatctga gcttactcc tcctgagaaa gatggccttc cttctggaaac
501 gccagcactg aatgccaagg gaacagaagc acccgcagta gtgacagagg
551 aggaggatga tgatgaagag actgctcctc ccgttattgc cccgcgaccg
601 gatcatacga aatcaattta cacacggtct gtaattgacc ctgttcctgc
651 accagttggt gattcacatg ttgatggtgc tgccaagtct tgccaaaac
701 agaaaaagaa g
```

PAK2 is Expressed Ubiquitously

Northern probe: nt 9-380 of PAK2 (nt 40=start codon)

Four RNA species (~7.5, 5, 4.4, and 3 kb) were detected in most tissues (Martin et al., EMBO J. 14, pp1970, 1995)

PAK2ΔL Inhibits Calcium Influx

Calcium Influx: Vector Control

PAK2 Kinase Activity is Required for TCR-induced NFAT Activation

Model for A Trans-Dominant Fragment Directly Inhibiting the Kinase Domain

Attempts to Generate a Kinase Inhibitory Segment

Effect of GFP-PAK2 Fragments on CD69

24hr anti-TCR stimulation

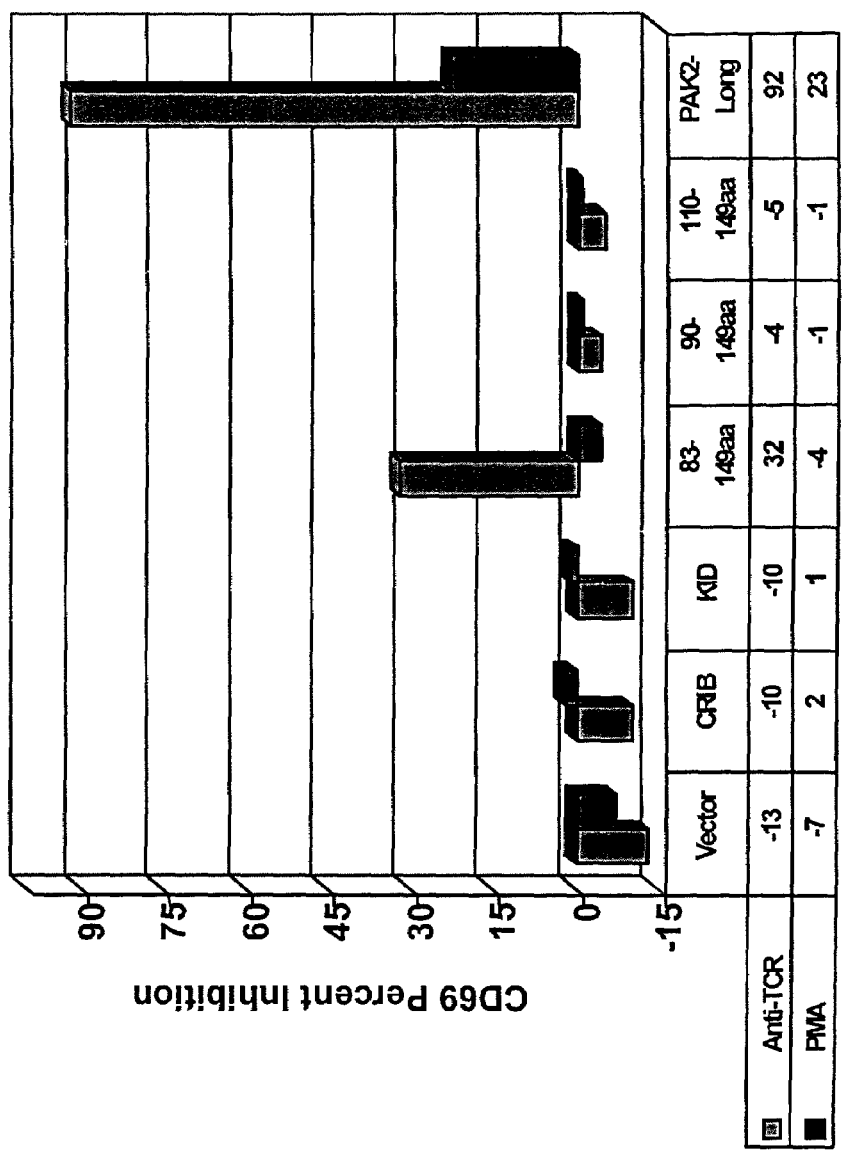

Figure 25B
Does the Inhibitory 83-149 PAK2 Fragment Bind to the PAK2 Kinase Domain?
Generating the PAK2 kinase domain alone:
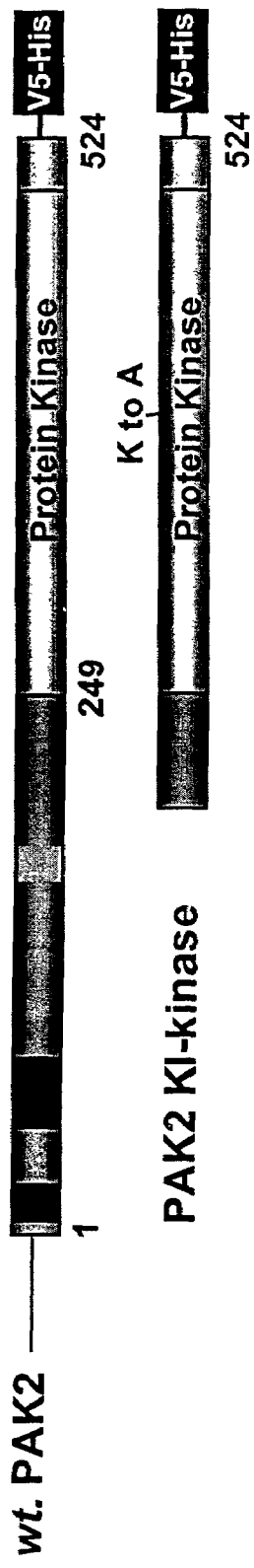
Expression of the PAK2 KI-kinase
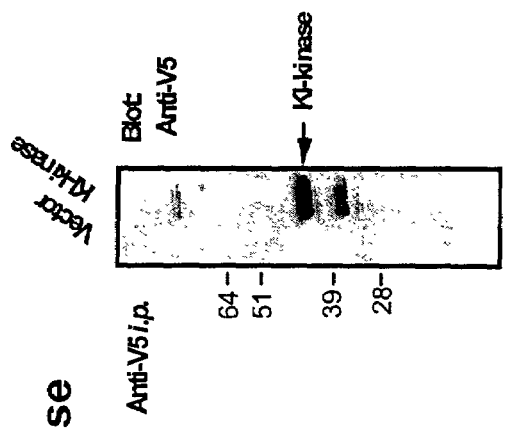

Trans Dominant GFP-PAK2 83-149aa Co-IPs With the Kinase Domain

This result strongly suggests that GFP-PAK2 83-149aa is mechanistically dominant negative via it's direct interaction with the the kinase domain.

US 7,118,854 B2

PAK2: MODULATORS OF LYMPHOCYTE ACTIVATION

CROSS-REFERENCES TO RELATED APPLICATIONS

The present application claims priority to U.S. Ser. No. 60/280,647, filed Mar. 30, 2001, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of T lymphocyte activation. More particularly, the present invention is directed to nucleic acids encoding PAK2, which is involved in modulation of T lymphocyte activation and TCR signaling. The invention further relates to methods for identifying and using agents, including small organic molecules, peptides, circular peptides, antibodies, lipids, antisense nucleic acids, and ribozymes, that modulate lymphocyte activation and TCR signaling via modulation of PAK2; as well as to the use of expression profiles and compositions in diagnosis and therapy related to lymphocyte activation and suppression.

BACKGROUND OF THE INVENTION

The immune response includes both a cellular and a humoral response. The cellular response is mediate largely by T lymphocytes (alternatively and equivalently referred to herein as T cells), while the humoral response is mediated by B lymphocytes (alternatively and equivalently referred to herein as B cells). Lymphocytes play a number of crucial roles in immune responses, including direct killing of virus-infected cells, cytokine and antibody production, and facilitation of B cell responses. Lymphocytes are also involved in acute and chronic inflammatory disease; asthma; allergies; autoimmune diseases such as scleroderma, pernicious anemia, multiple sclerosis, myasthenia gravis, IDDM, rheumatoid arthritis, systemic lupus erythematosus, and Crohn's disease; and organ and tissue transplant disease, e.g., graft vs. host disease.

B lymphocytes produce and secrete antibodies in response to the concerted presentation of antigen and MHC class II molecules on the surface of antigen presenting cells. Antigen presentation initiates B cell activation through the B cell receptor (BCR) at the B cell surface. Signal transduction from the BCR leads to B cell activation and changes in B cell gene expression, physiology, and function, including secretion of antibodies.

T cells do not produce antibodies, but many subtypes of T cells produce co-stimulatory molecules that augment antibody production by B cells during the humoral immune response. In addition, many T cells engulf and destroy cells or agents that are recognized by cell surface receptors. Engagement of the cell surface T cell receptor (TCR) initiates T cell activation. Signal transduction from the TCR leads to T cell activation and changes in T cell gene expression, physiology, and function, including the secretion of cytokines.

Identifying ligands, receptors, and signaling proteins downstream of TCR, as well as BCR, activation is important for developing therapeutic regents to inhibit immune response in inflammatory disease, autoimmune disease, and organ transplant, as well as to activate immune response in immunocompromised subjects, and in patients with infectious disease and cancer (see, e.g., Rogge et al., Nature Genetics 25:96–101 (2000); U.S. Pat. Nos. 5,518,911; 5,605,825; 5,698,428; 5,698,445; 6,013,464; and 6,048,706).

SUMMARY OF THE INVENTION

The present invention provides nucleic acids encoding PAK2, which is a serine/threonine kinase involved in modulation of T lymphocyte activation and TCR signaling. The invention therefore provides methods of screening for compounds, e.g., small organic molecules, antibodies, peptides (such as PAK2 kinase domain fragments), circular peptides, lipids, antisense molecules, and ribozymes, that are capable of modulating lymphocyte activation, including TCR signaling, e.g., either activating or inhibiting T lymphocytes. Therapeutic and diagnostic methods and reagents are also provided.

In one aspect of the invention, nucleic acids encoding PAK2 are provided. In another aspect, the present invention provides nucleic acids, such as probes, antisense oligonucleotides, and ribozymes, that hybridize to a gene encoding a PAK2 protein. In another aspect, the invention provides expression vectors and host cells comprising PAK2-encoding nucleic acids. In another aspect, the present invention provides PAK2 protein, and antibodies thereto.

In another aspect, the present invention provides a method for identifying a compound that modulates T lymphocyte activation, the method comprising the steps of: (i) contacting a T cell comprising a PAK2 polypeptide or fragment thereof with the compound, the PAK2 polypeptide or fragment thereof encoded by a nucleic acid that hybridizes under stringent conditions to a nucleic acid encoding a polypeptide having an amino acid sequence of SEQ ID NO:2; and (ii) determining the chemical or phenotypic effect of the compound upon the cell comprising the PAK2 polypeptide or fragment thereof, thereby identifying a compound that modulates T lymphocyte activation.

In another aspect, the present invention provides a method for identifying a compound that modulates T lymphocyte activation, the method comprising the steps of: (i) contacting the compound with a PAK2 polypeptide or a fragment thereof, the PAK2 polypeptide or fragment thereof encoded by a nucleic acid that hybridizes under stringent conditions to a nucleic acid encoding a polypeptide having an amino acid sequence of SEQ ID NO:2; (ii) determining the physical effect of the compound upon the PAK2 polypeptide; and (iii) determining the chemical or phenotypic effect of the compound upon a cell comprising the PAK2 polypeptide or fragment thereof, thereby identifying a compound that modulates T lymphocyte activation.

In one embodiment, the host cell is primary T lymphocyte or a cultured T lymphocyte, e.g., a Jurkat cell.

In another embodiment, the chemical or phenotypic effect is determined by measuring CD69 expression, NFAT expression, CD40L expression, IL-2 production, intracellular $Ca^{2+}$ mobilization, $Ca^{2+}$ influx, or lymphocyte proliferation.

In another embodiment, modulation is inhibition of T lymphocyte activation.

In another embodiment, the polypeptide is recombinant. In another embodiment, the PAK2 polypeptide comprises an amino acid sequence of SEQ ID NO:2. In another embodiment, the PAK2 polypeptide is encoded by a nucleic acid comprising a nucleotide sequence of SEQ ID NO:1.

In another embodiment, the compound is an antibody, antisense molecule, small organic molecule, peptide, or a circular peptide.

In another aspect, the present invention provides a method of modulating T lymphocyte activation in a subject, the method comprising the step of administering to the subject a therapeutically effective amount of a compound identified using the methods described above.

In one embodiment, the subject is a human.

In another asepct, the present invention provides a method of modulating T lymphocyte activation in a subject, the method comprising the step of administering to the subject a therapeutically effective amount of a PAK2 polypeptide, the polypeptide encoded by a nucleic acid that hybridizes under stringent conditions to a nucleic acid encoding a polypeptide having an amino acid sequence of SEQ ID NO:2.

In another aspect, the present invention provides a method of modulating T lymphocyte activation in a subject, the method comprising the step of administering to the subject a therapeutically effective amount of a nucleic acid encoding a PAK2 polypeptide, wherein the nucleic acid hybridizes under stringent conditions to a nucleic acid encoding a polypeptide having an amino acid sequence of SEQ ID NO:2.

BRIEF DESCRIPTION OF THE DRAWINGS

FIG. 1 shows a schematic representation of PAK proteins.

FIG. 2 shows an nucleotide (SEQ ID NO:1) and amino acid (SEQ ID NO:2) sequence for human PAK2.

FIG. 3 provides an alignment of PAK1 (SEQ ID NO:5), PAK2 (SEQ ID NO:2) and PAK3 (SEQ ID NO:6) amino acid sequences.

FIG. 4A shows phenotypic assays in Jurkat cells.

FIG. 6A shows successful phenotype transfer of PAK2ΔS.

FIG. 7A shows cell specificity of the PAK2ΔL effect.

FIG. 8B shows that PAK2ΔL specifically inhibits PCR signaling.

FIG. 9B shows the relative level of PAK1 message in various human tissues.

FIG. 17A shows an assay for determining the involvement of PAK2 in TCR signaling.

FIG. 18 shows the nucleotide sequence for PAK2 full-length (SEQ ID NO:1), PAK2ΔS (SEQ ID NO:3) and PAK2ΔL (SEQ ID NO:4).

FIG. 25A shows the effect of GFP-PAK2 fragments on Jurkat TAgCD69 (% inhibition).

FIG. 25B shows binding of the PAK3 fragment to the kinase domain.

DETAILED DESCRIPTION OF THE INVENTION

Introduction

Figure 4B:
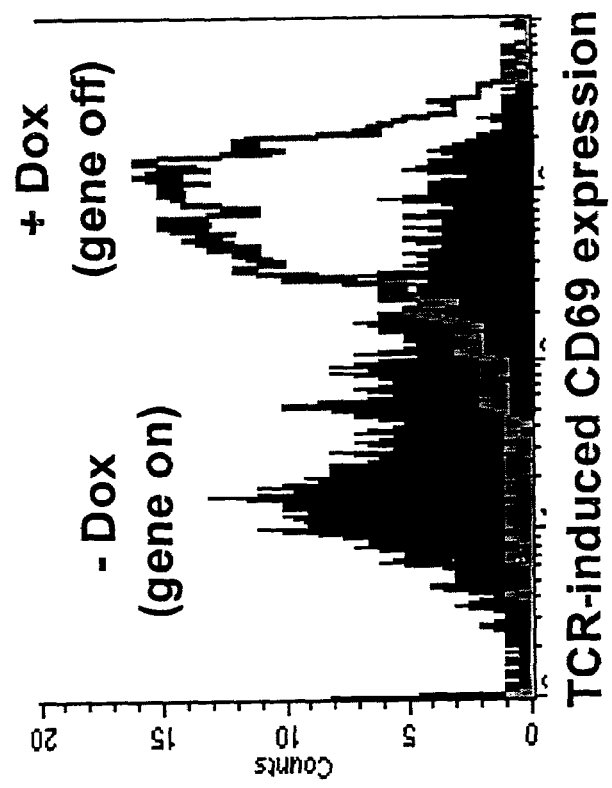
FIG. 4B shows identification of inhibitory hits.
Figure 5A:
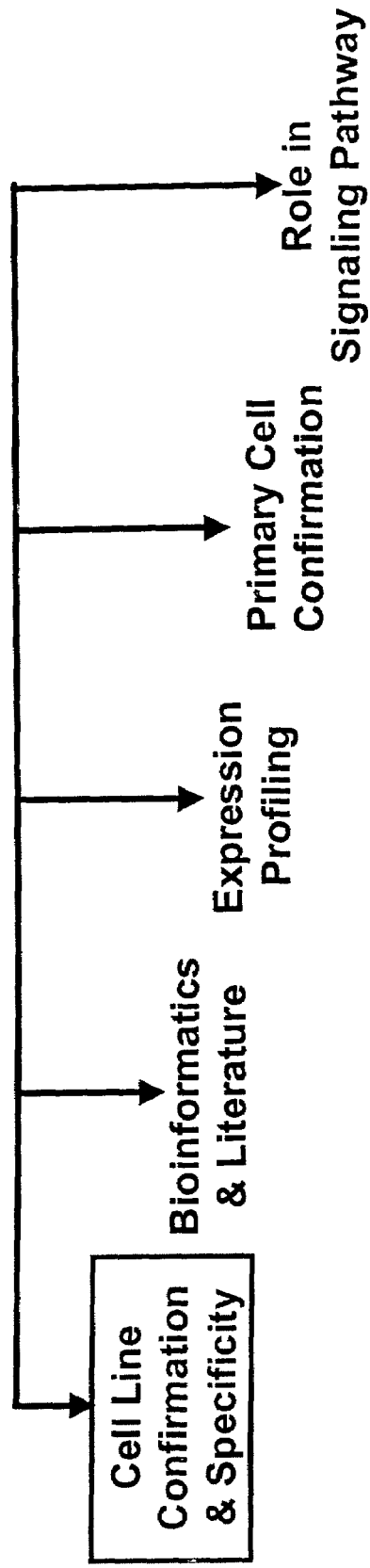
FIG. 5A shows a diagram of target validation.
Figure 5B:
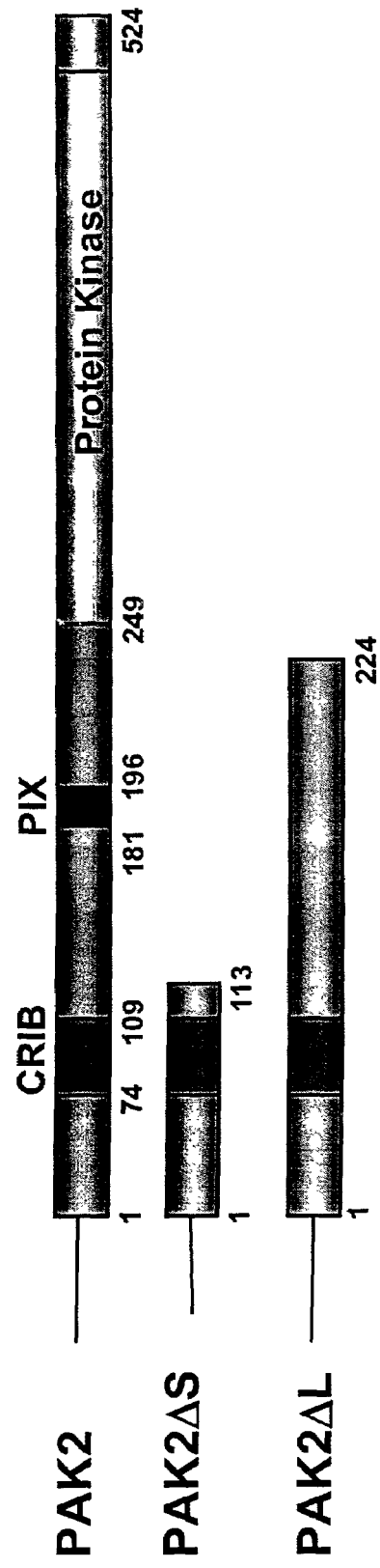
FIG. 5B shows PAK2 mutant proteins identified in a CD69 assay.
Figure 6B:
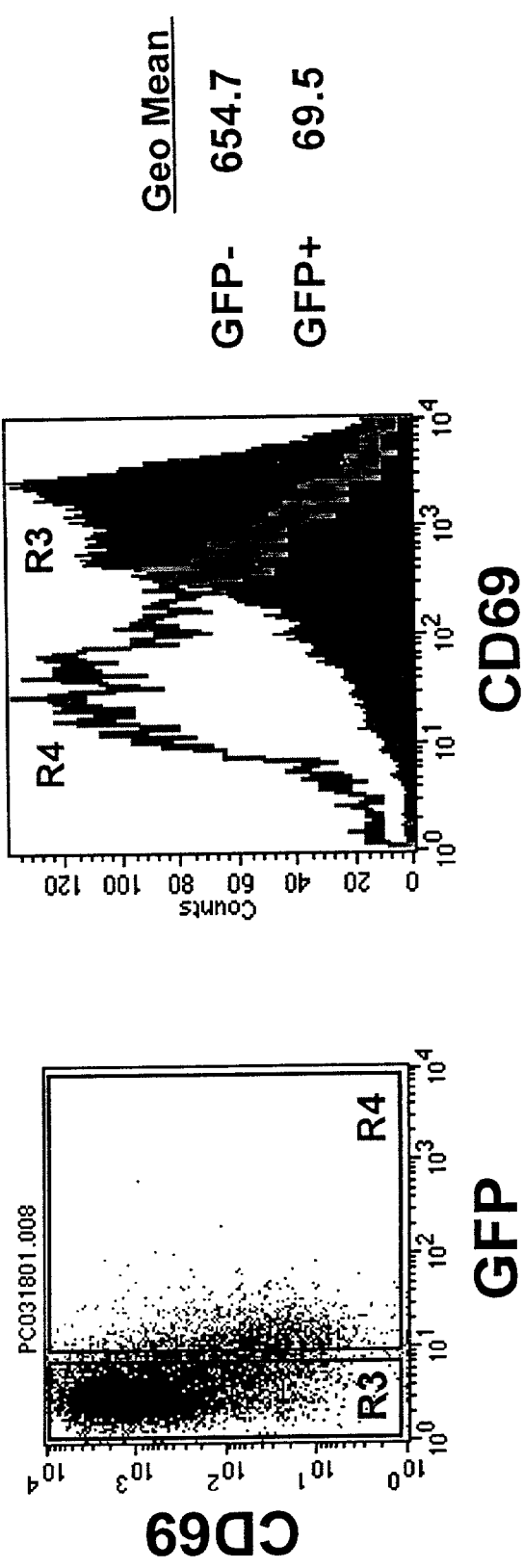
FIG. 6B shows successful phenotype transfer of PAK2ΔL.
Figure 7B:
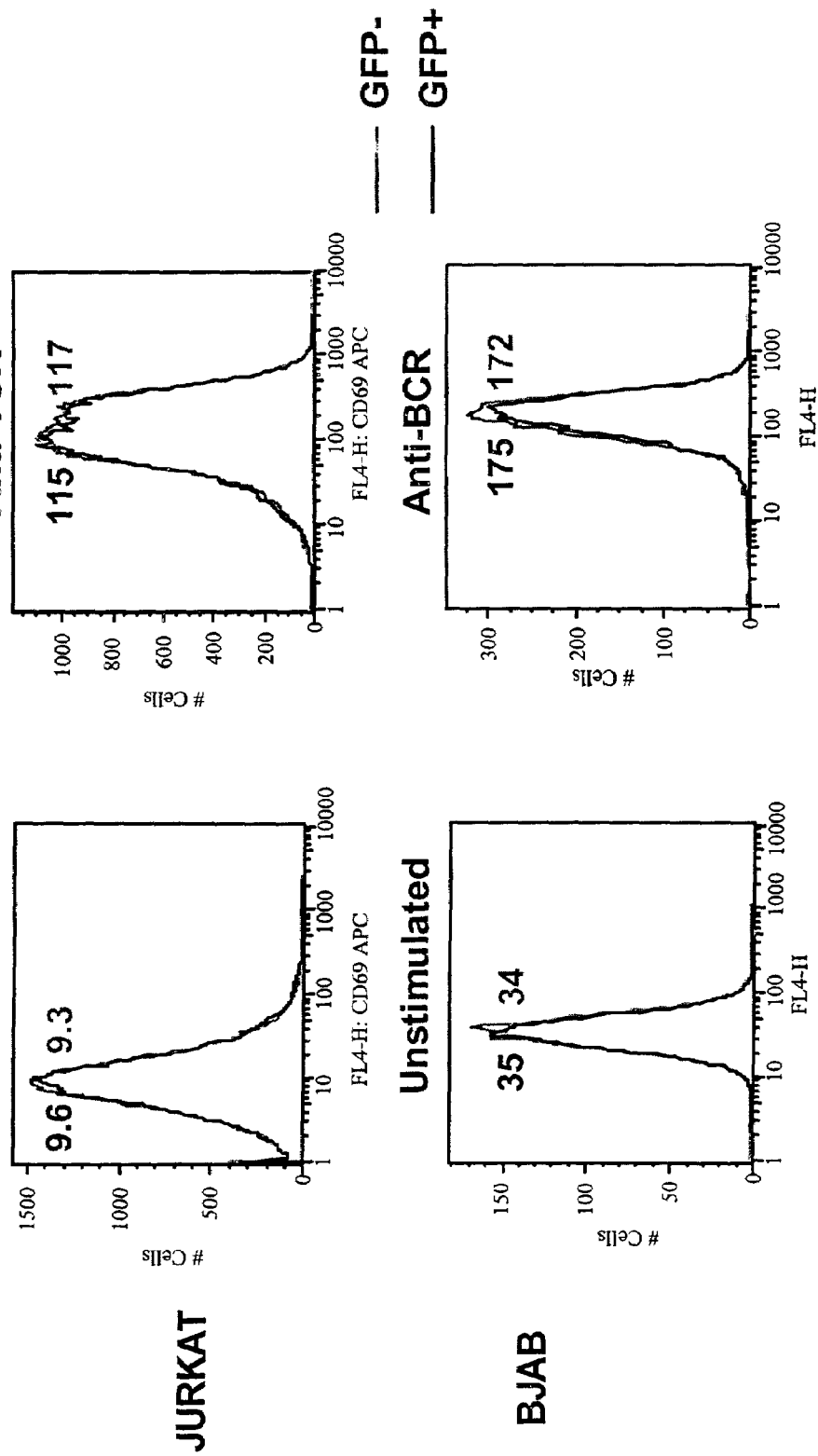
FIG. 7B shows TCR induced CD69 upregulation IRES-vector control.
Figure 8A:
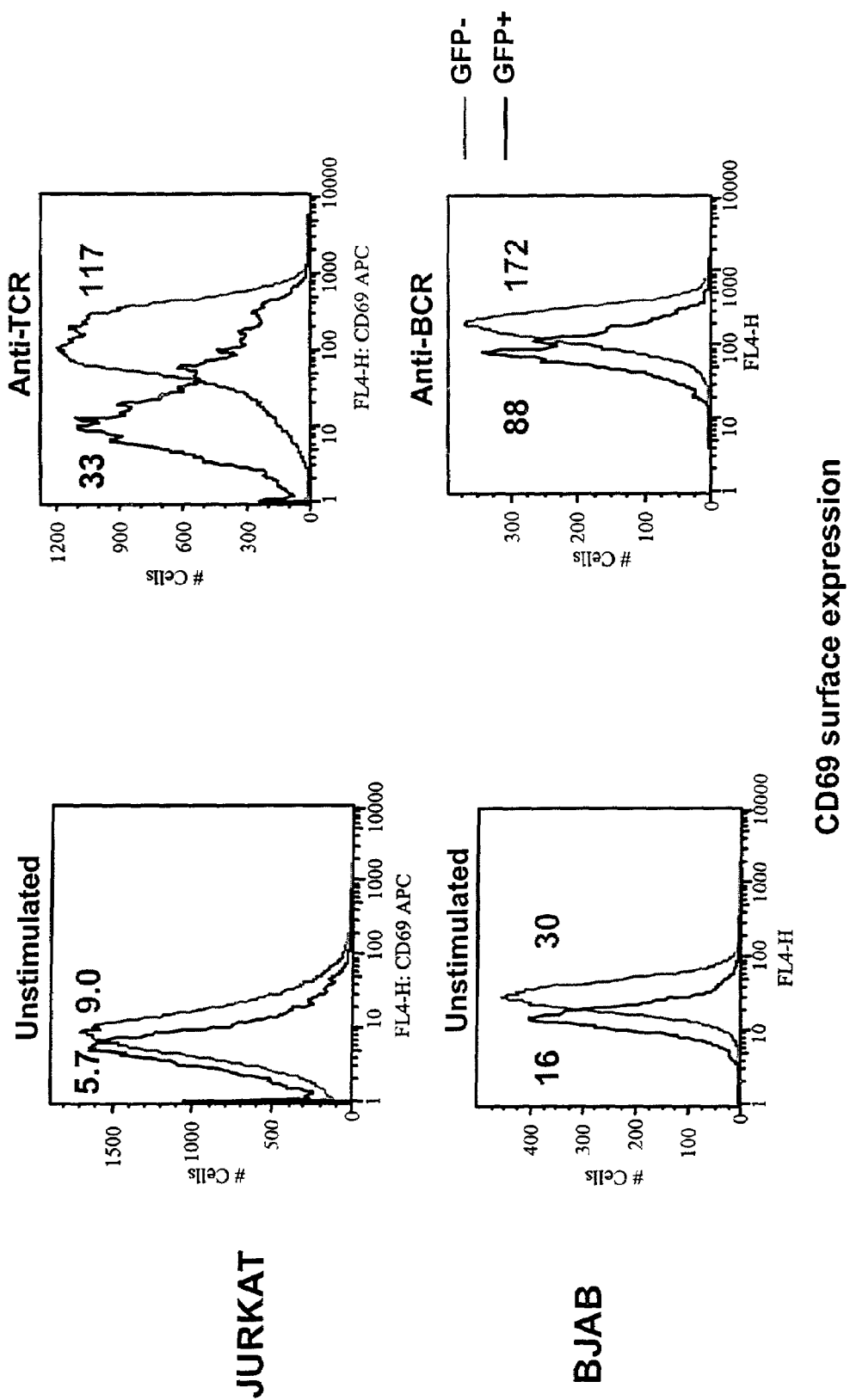
FIG. 8A shows DN-Syk inhibits both TCR and BCR signaling.
Figure 9A:
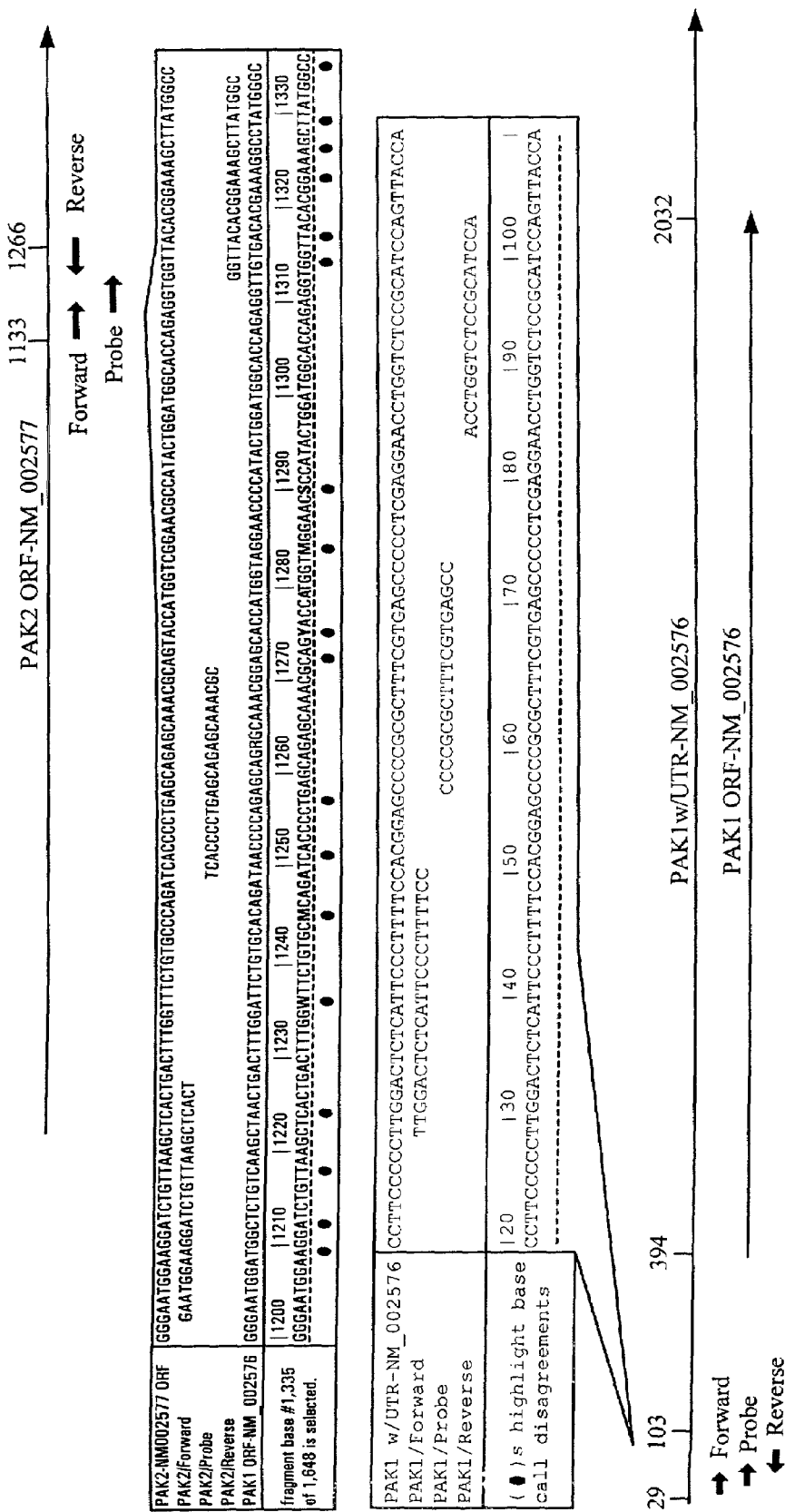
FIG. 9A shows TaqMan quantitative detection of PAK1 or PAK2 mRNA (PAK2-NM002577 ORF=SEQ ID NO:7; PAK2/Forward=SEQ ID NO:8; PAK2/Probe=SEQ ID NO:9; PAK2/Reverse=SEQ ID NO:10; PAK1 ORF-NM_002576=SEQ ID NO:11; Fragment base #1,335 of 1648=SEQ ID NO:12; PAK1 w/UTR-NM_002576=SEQ ID NO:13; PAK1/Forward=SEQ ID NO:14; PAK1/Probe=SEQ ID NO:15; PAK1/Reverse=SEQ ID NO:16).
Figure 10A:
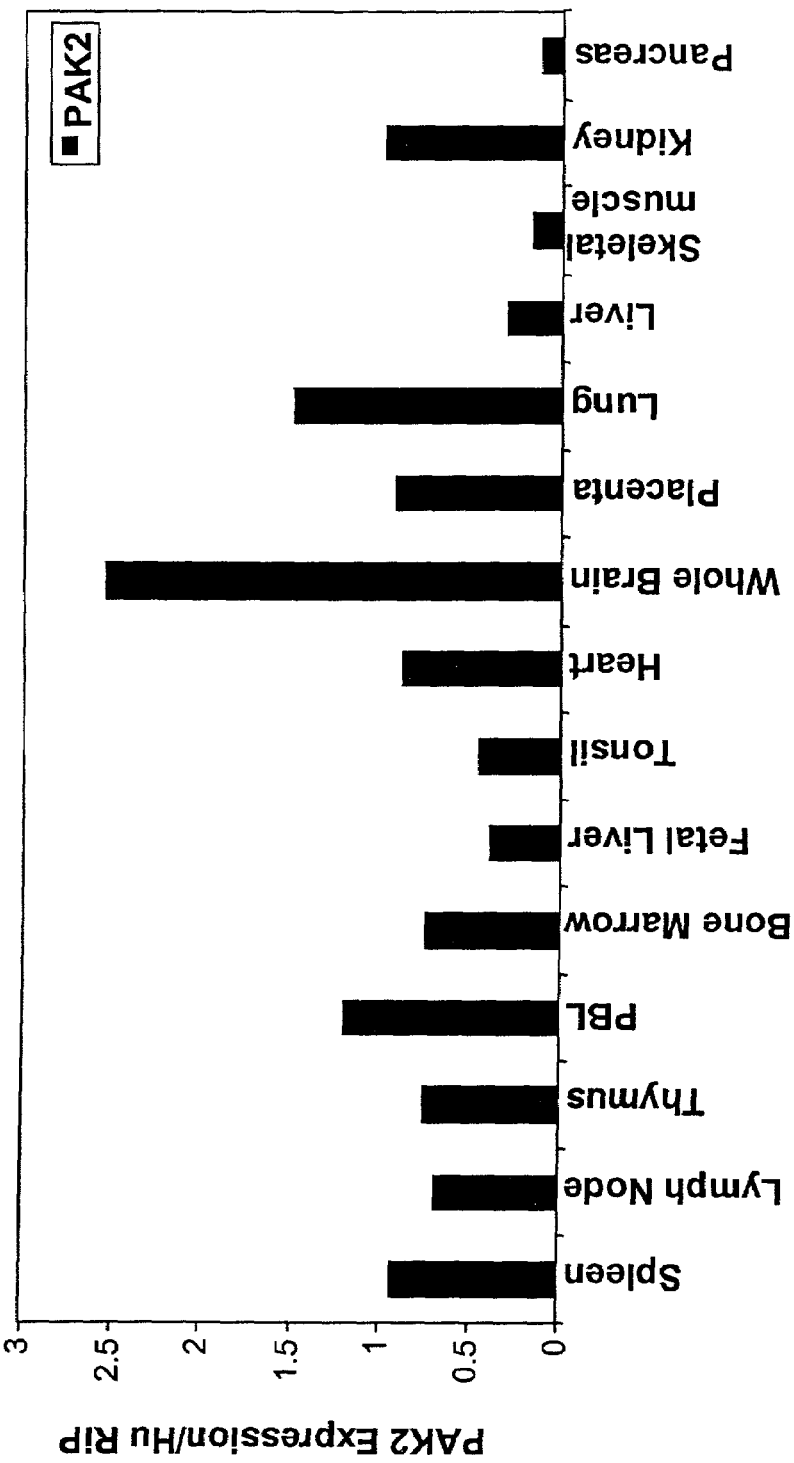
FIG. 10A shows the relative level of PAK2 mRNA in various human tissues.
Figure 10B:
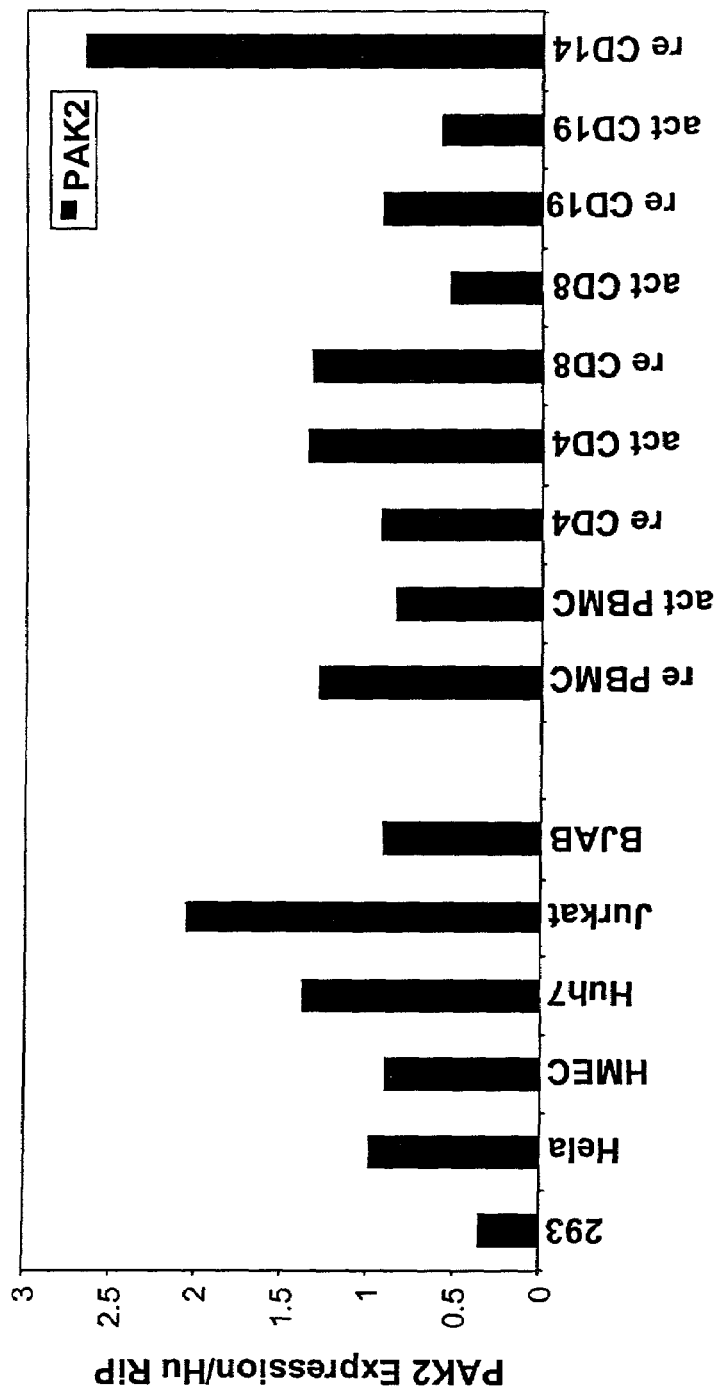
FIG. 10B shows the relative level of PAK2 mRNA in various human cell lines and cell populations.
Figure 11A:
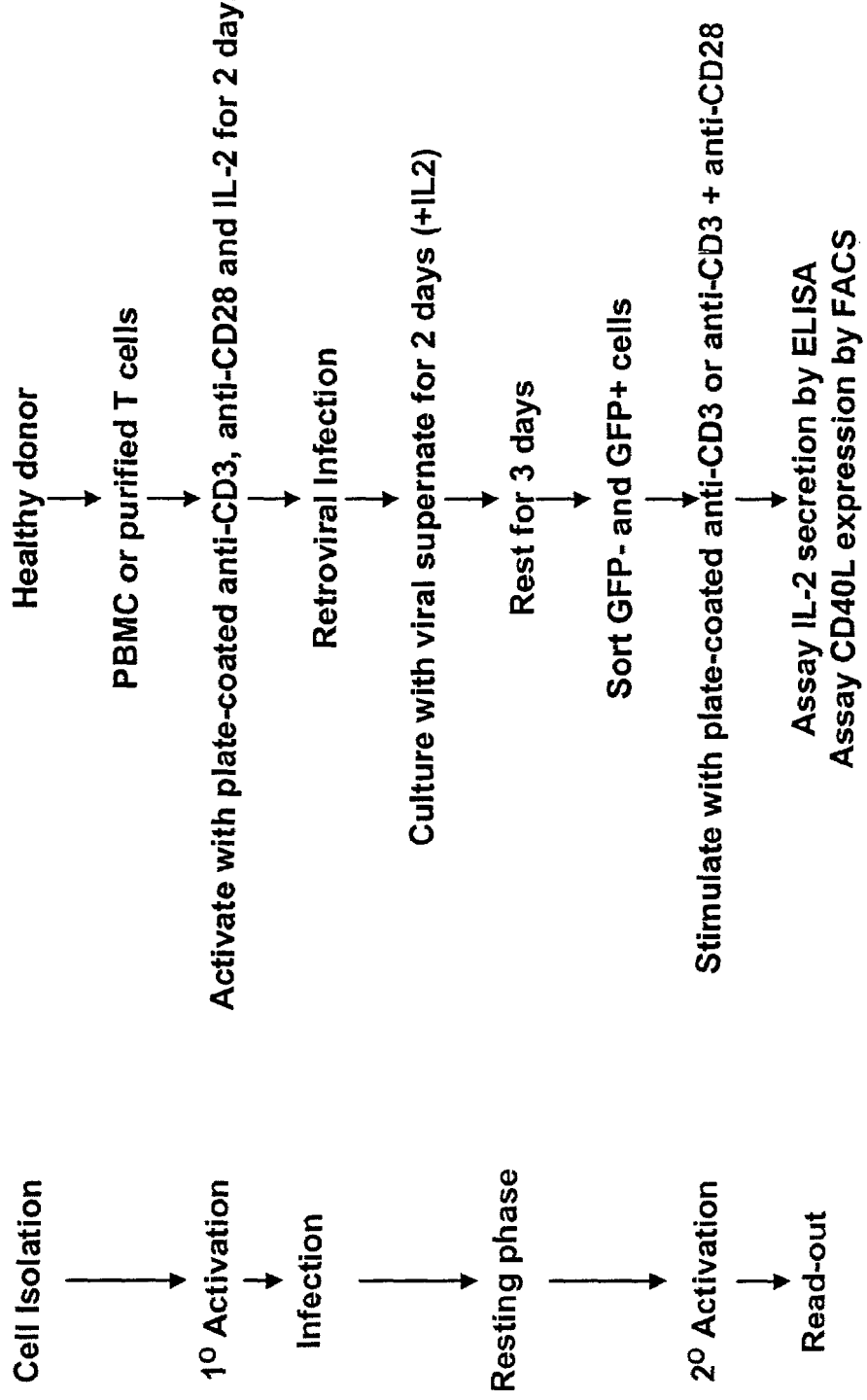
FIG. 11A shows retroviral infection of primary T lymphocytes.
Figure 11B:
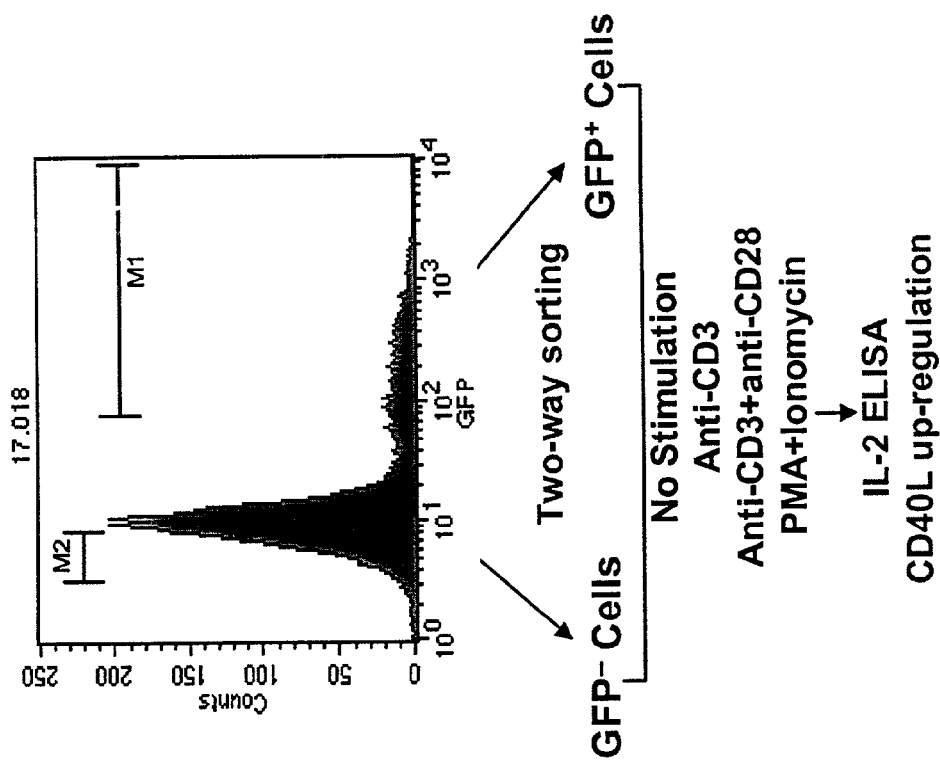
FIG. 11B shows primary T cell assays.
Figure 12A:
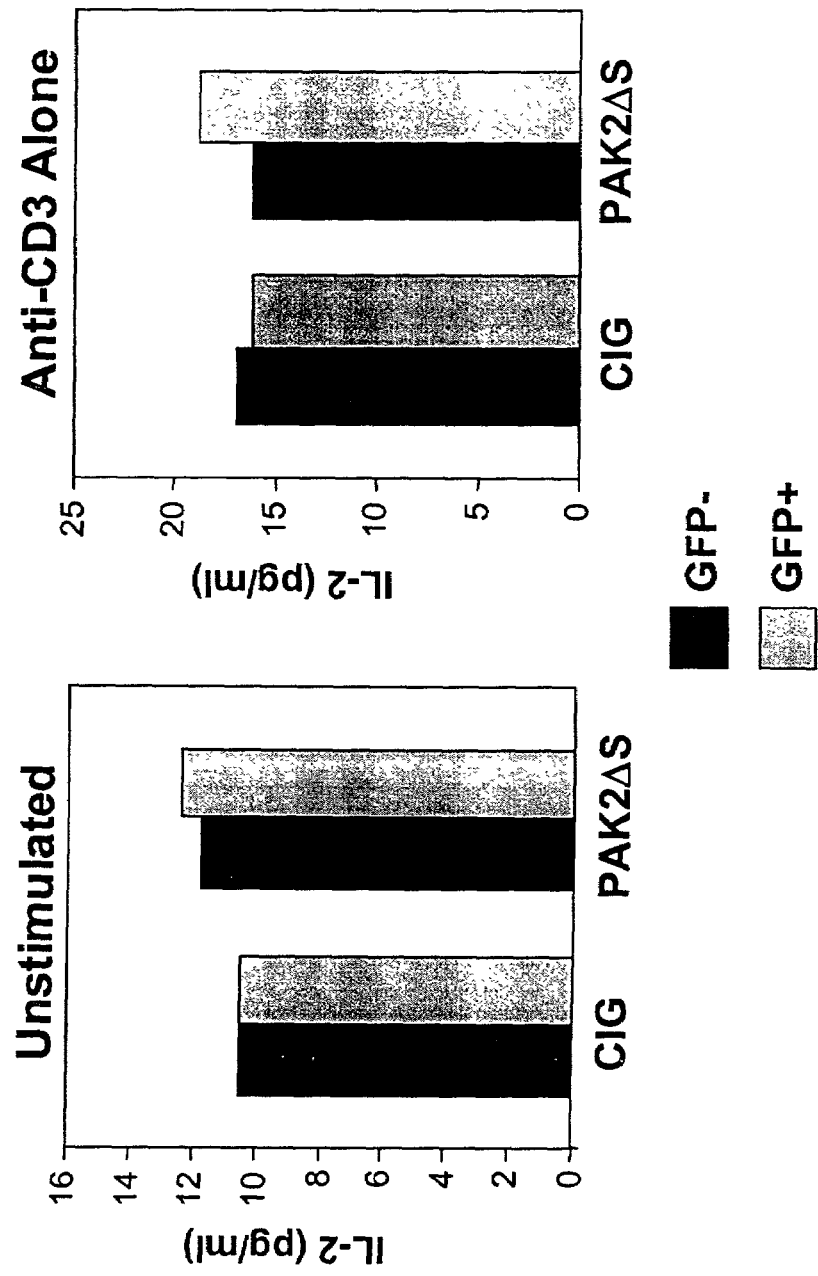
FIG. 12A shows that anti-CD3 alone was not sufficient to induce IL-2 secretion.
Figure 12B:
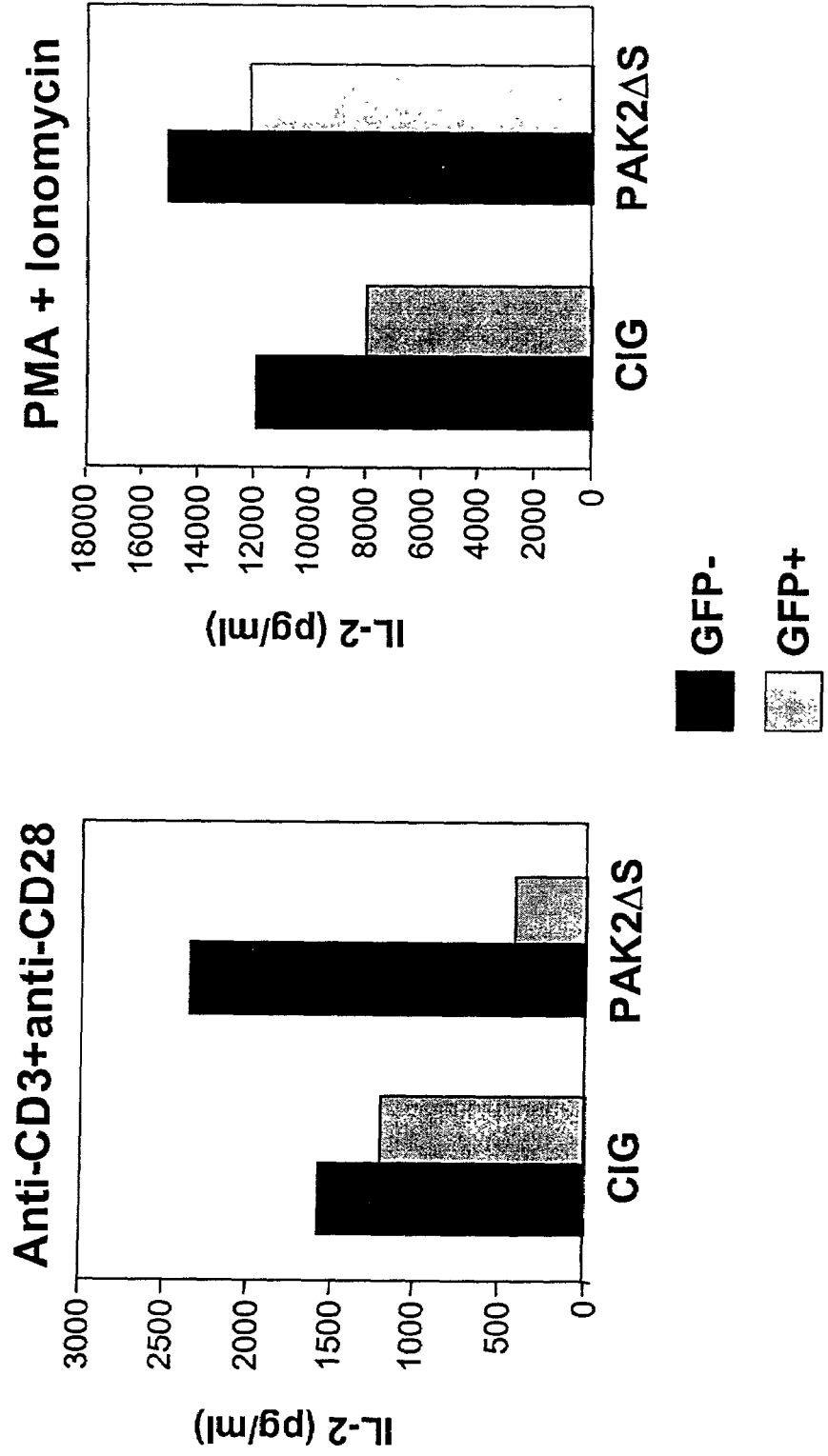
FIG. 12B shows that PAK2ΔS inhibits anti-CD3/anti-CD28 induced IL-2 secretion.
Figure 13A:
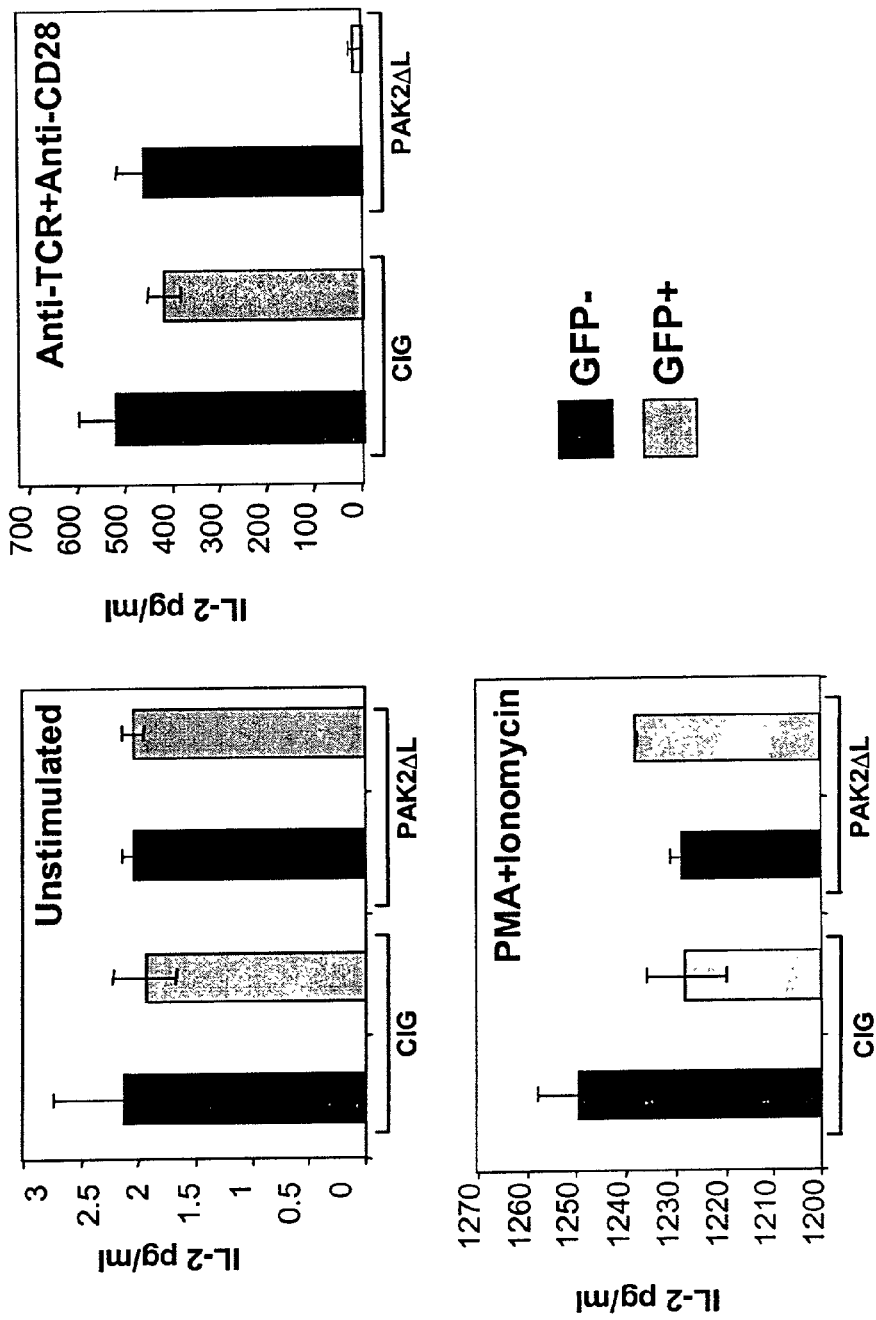
FIG. 13A shows that PAK2ΔL inhibits receptor-mediated IL-2 secretion in primary T cells.
Figure 13B:
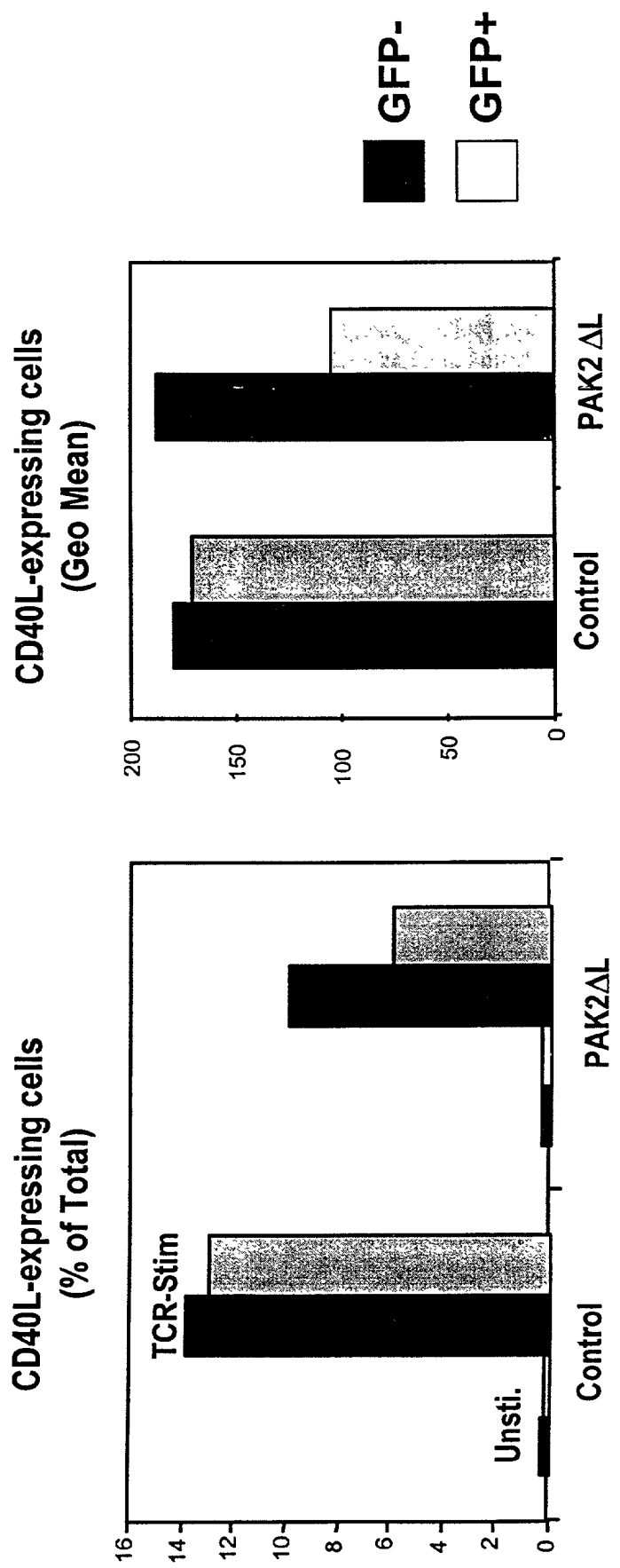
FIG. 13B shows that PAK2ΔL inhibits receptor-mediated CD40L up-regulation in primary T cells.
Figure 14A:
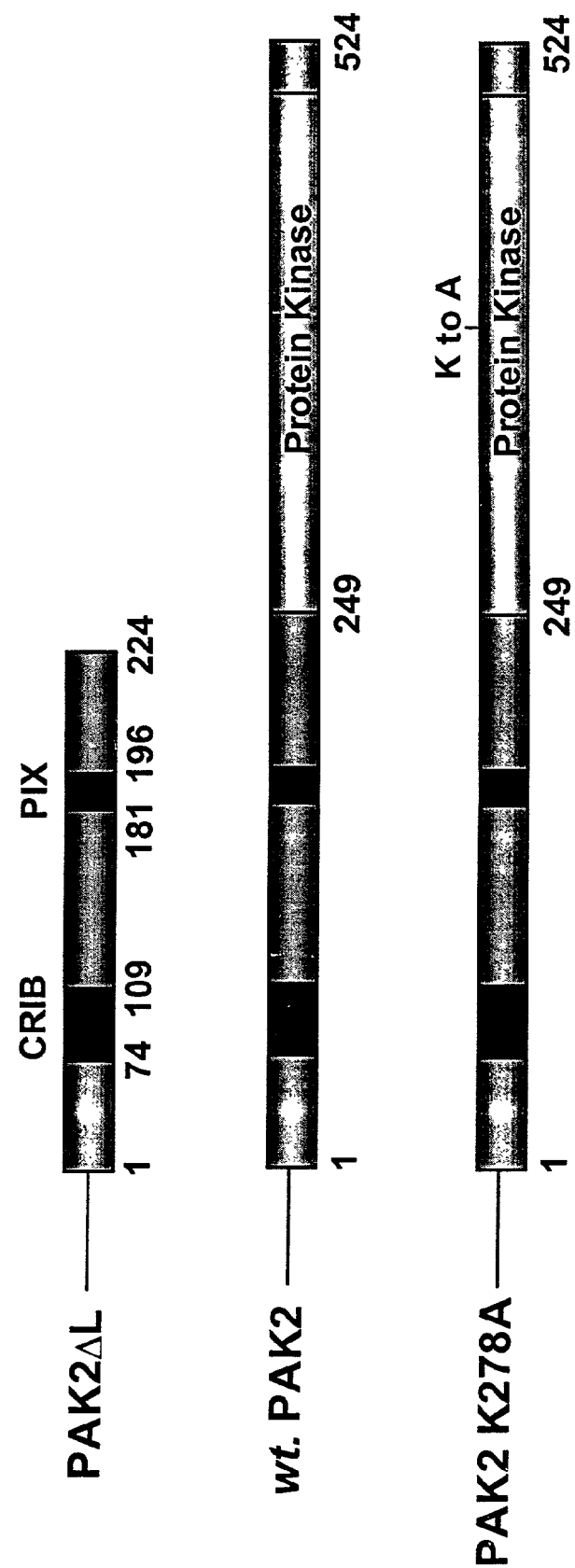
FIG. 14A shows wild type and kinase inactivated PAK2.
Figure 14B:
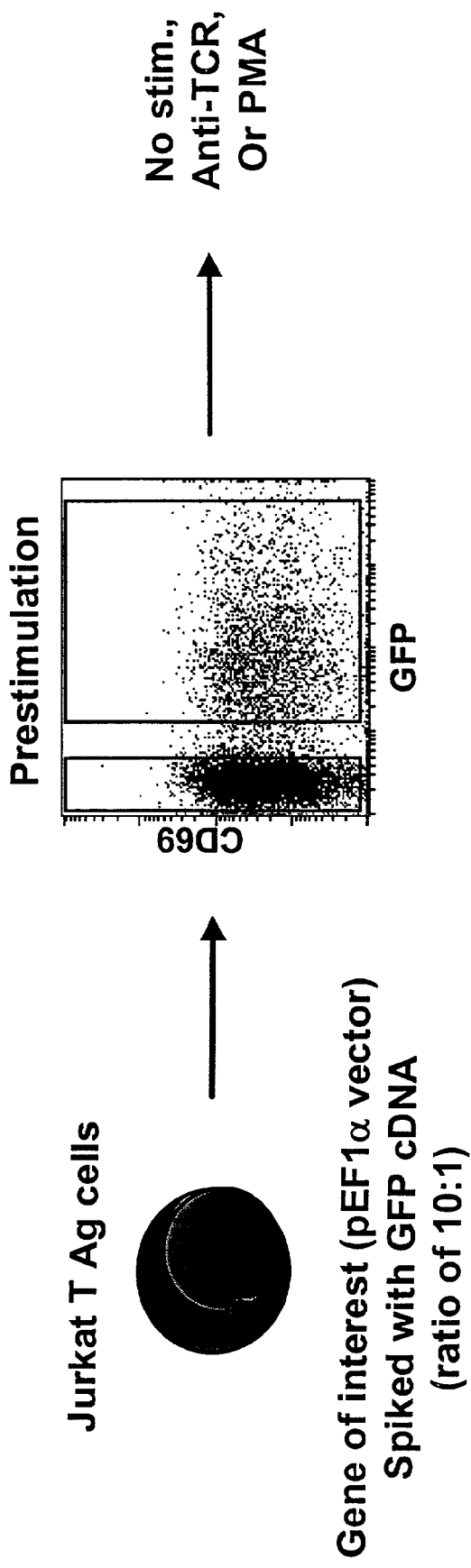
FIG. 14B shows a transient overexpression assay to examine the TCR induced CD69 upregulation.
Figure 15A:
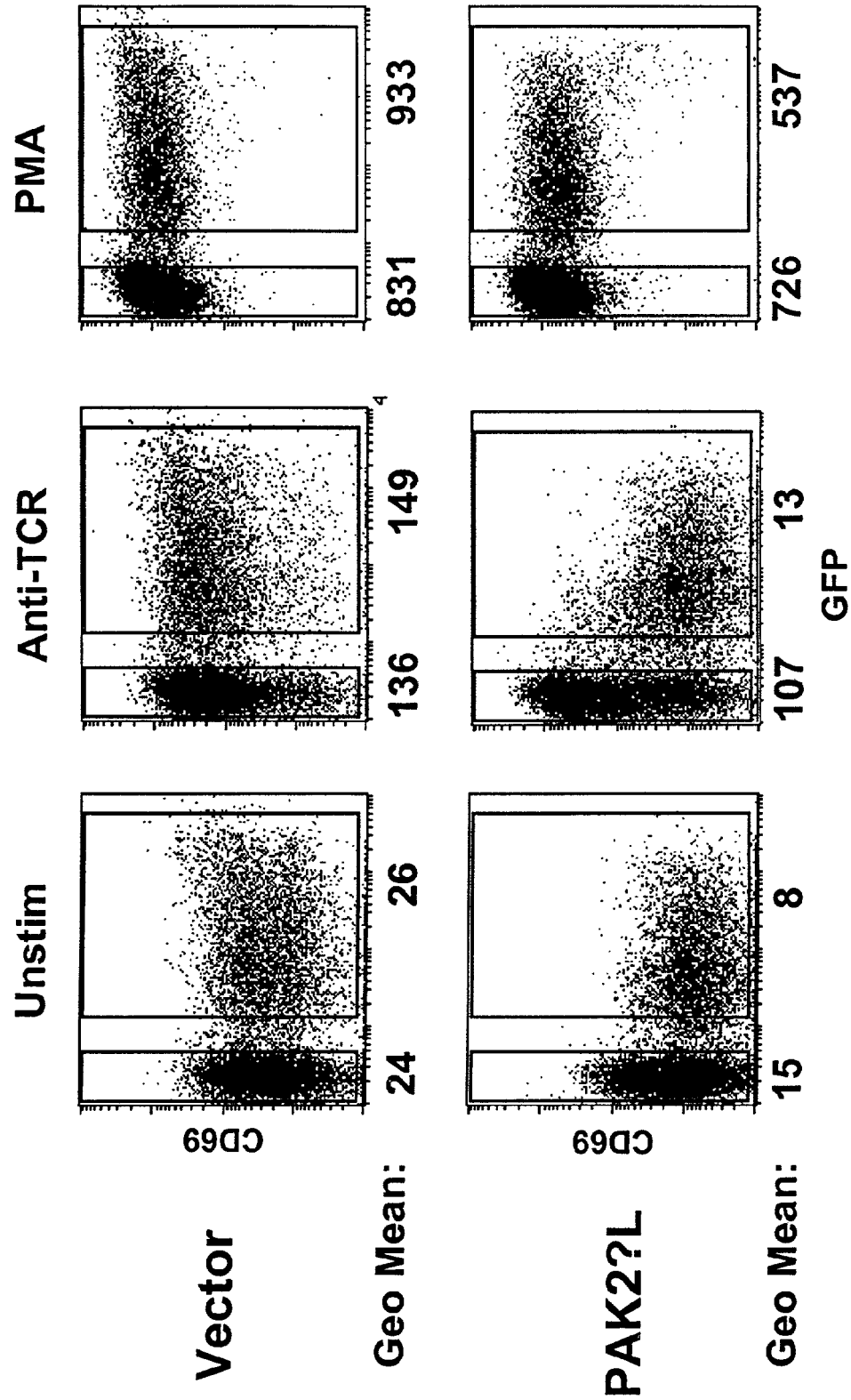
FIG. 15A shows that PAK2ΔL inhibits TCR signaling.
Figure 15B:
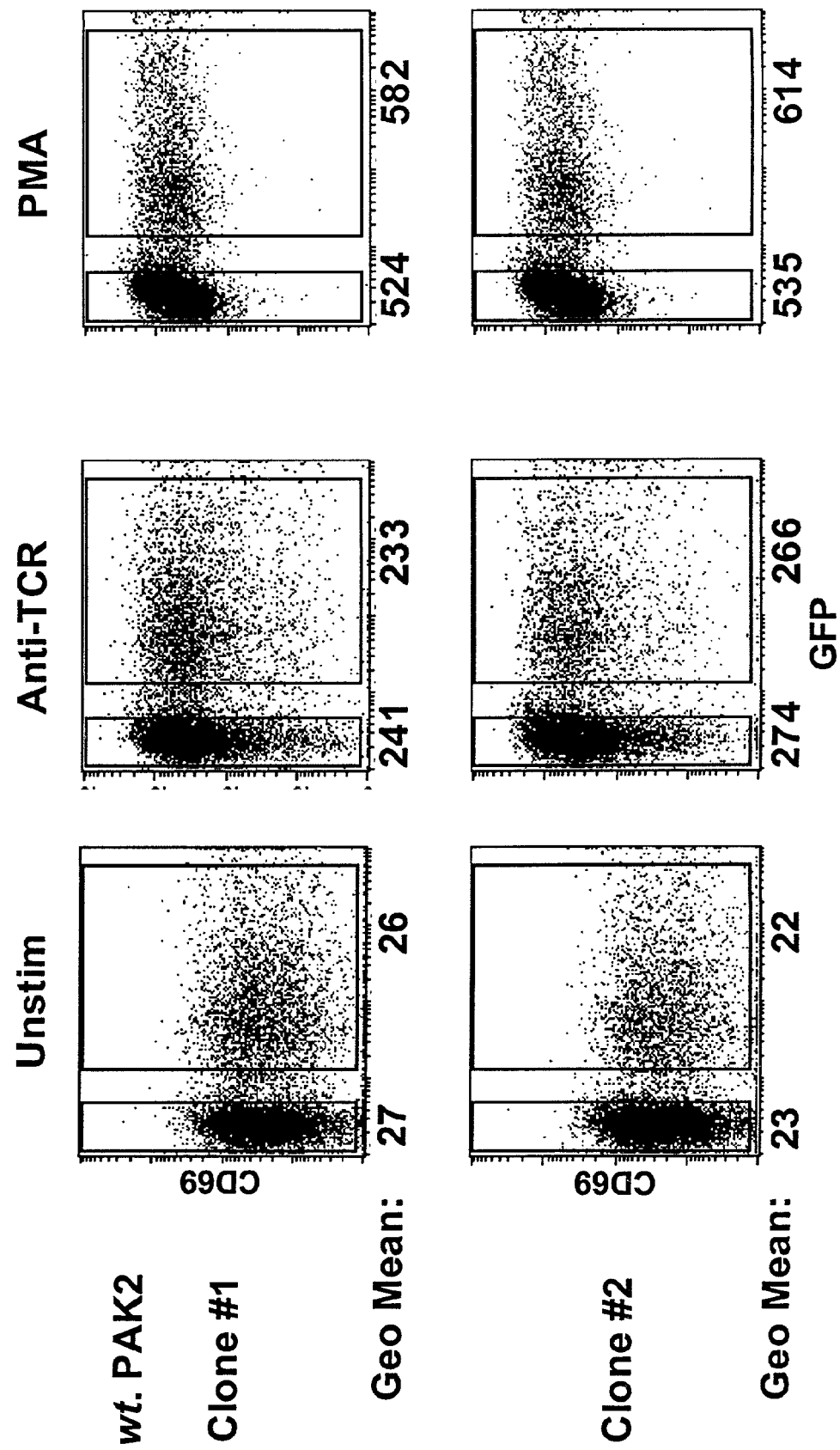
FIG. 15B shows that wild-type PAK2 does not inhibit CD69.
Figure 16A:
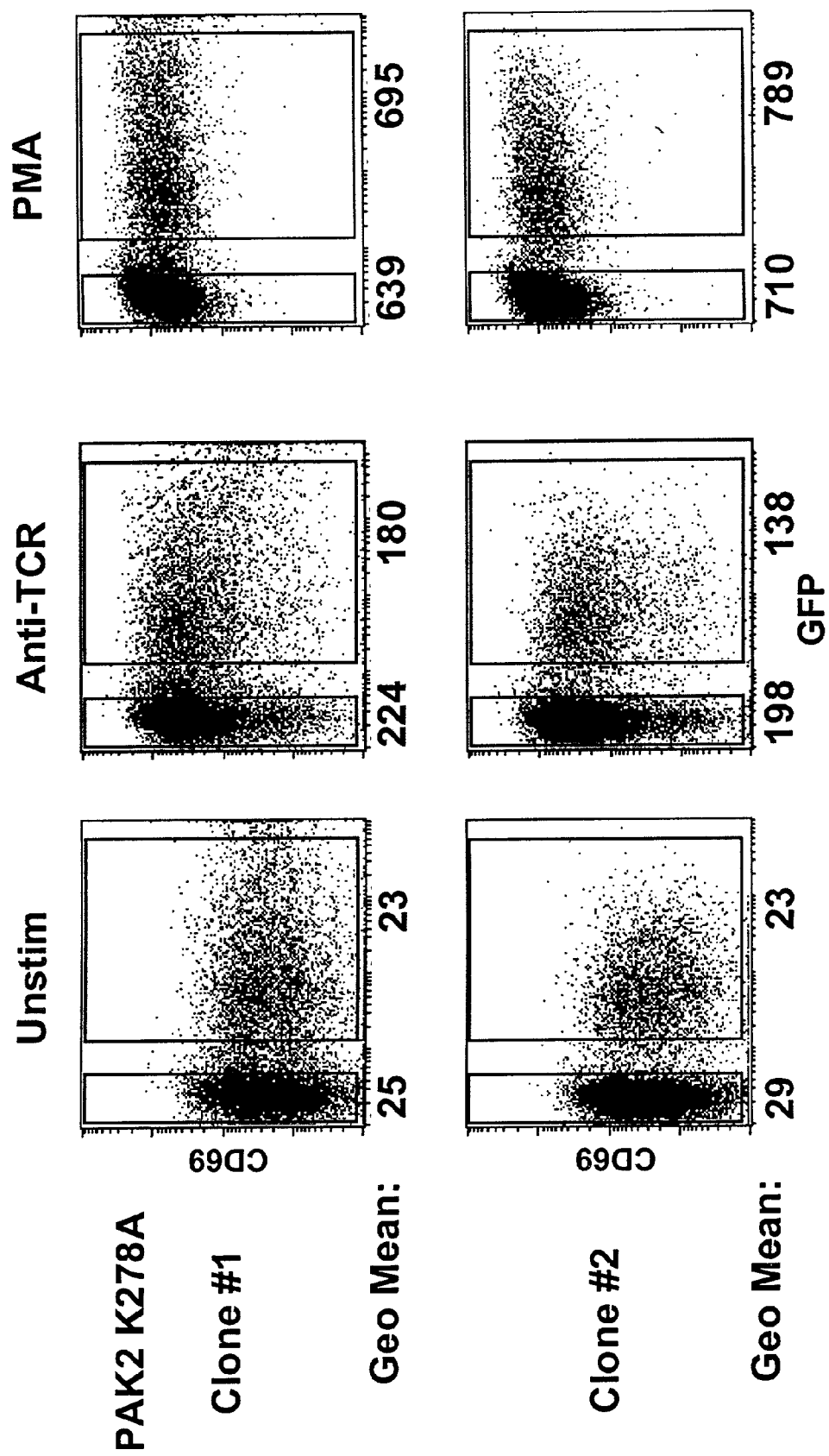
FIG. 16A shows that kinase inactive PAK2 partially inhibits CD69.
Figure 16B:
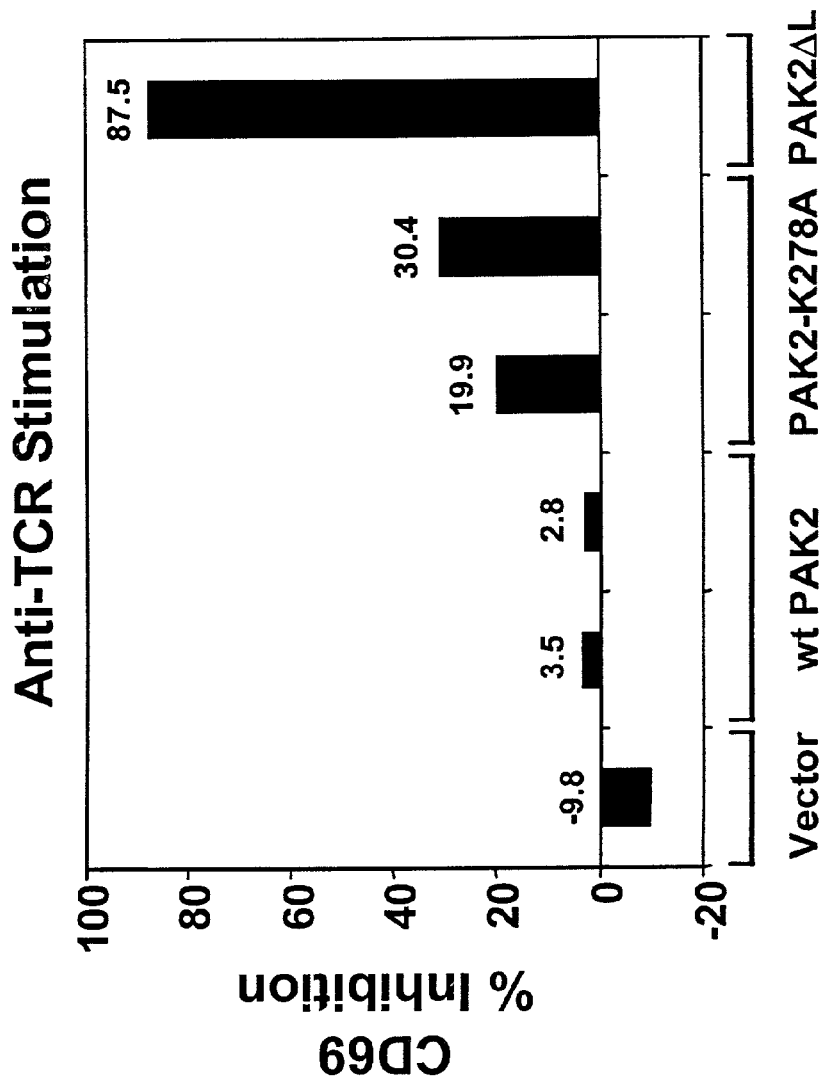
FIG. 16B shows a summary of PAK2 inhibition of CD69.
Figure 17B:
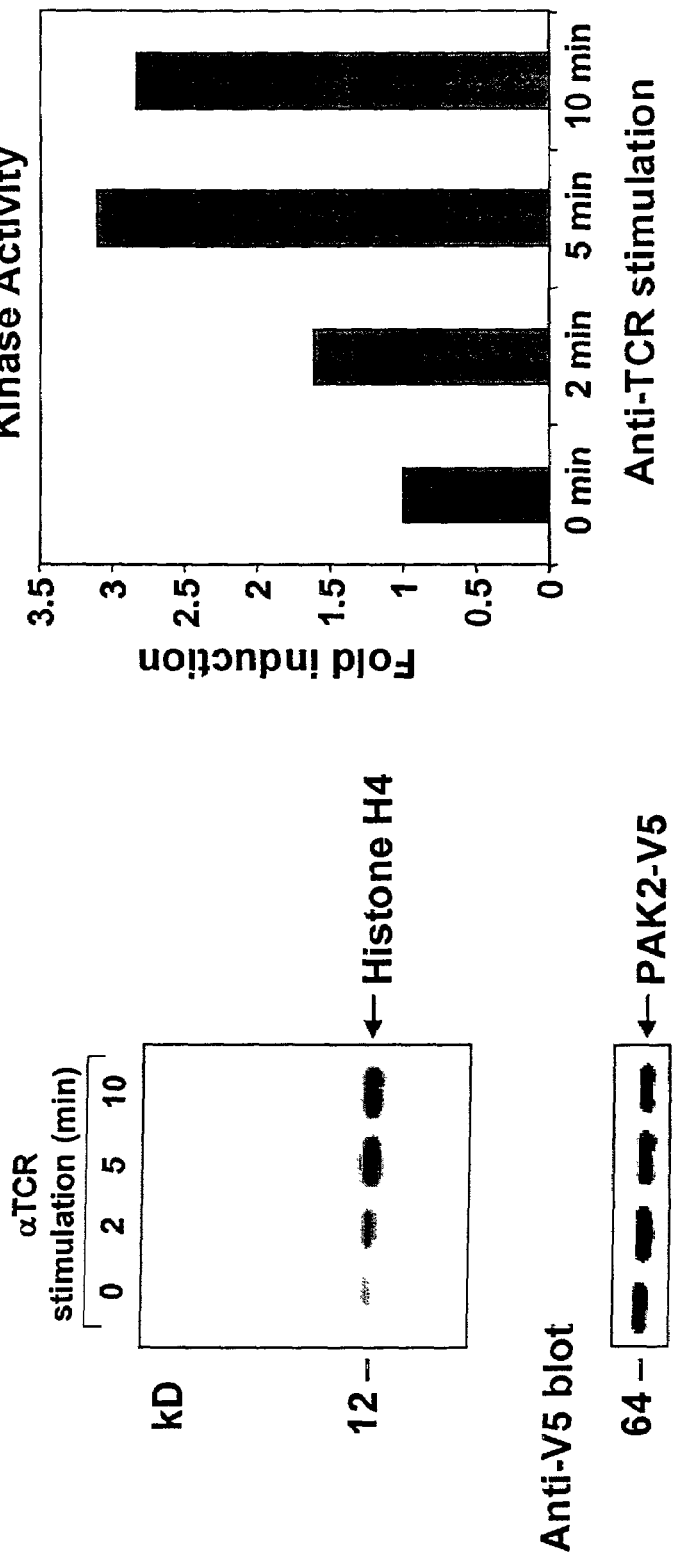
FIG. 17B shows that TCR stimulates PAK2 kinase activity.
Figure 19A:
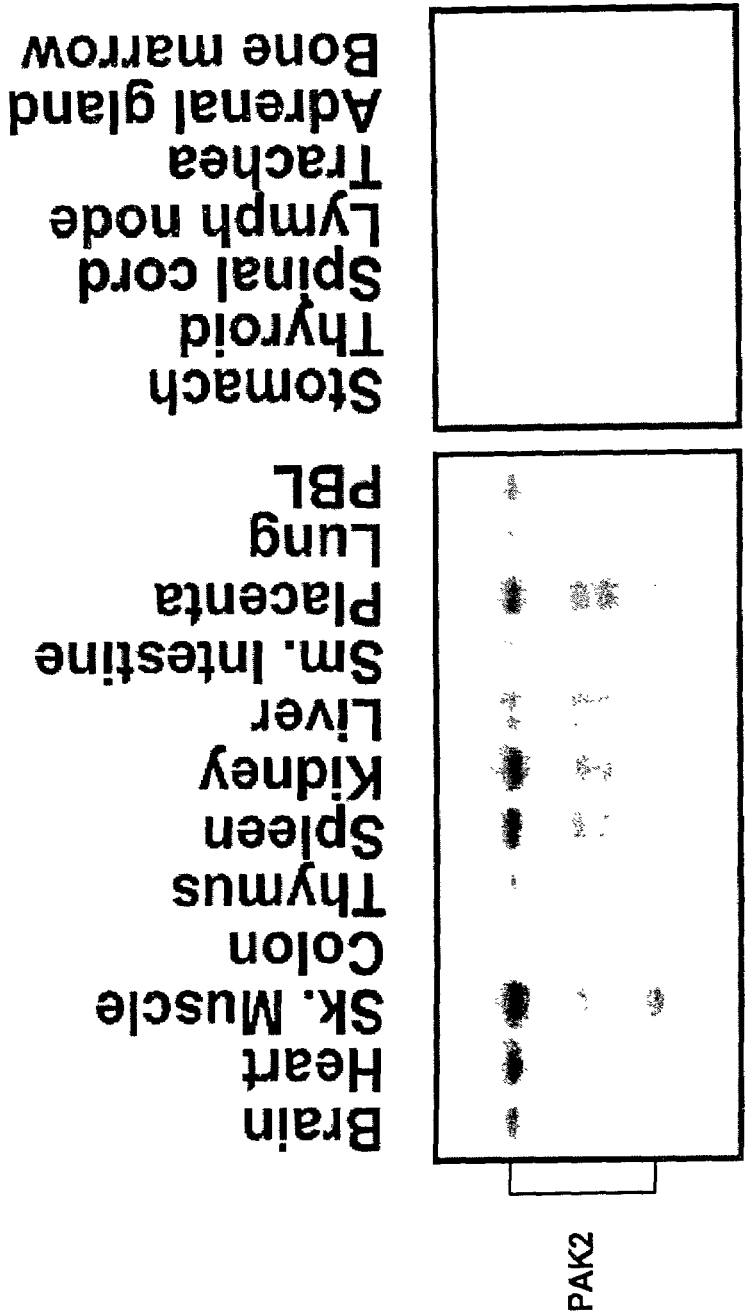
FIG. 19A shows PAK2 mRNA expression in tissues.
Figure 19:
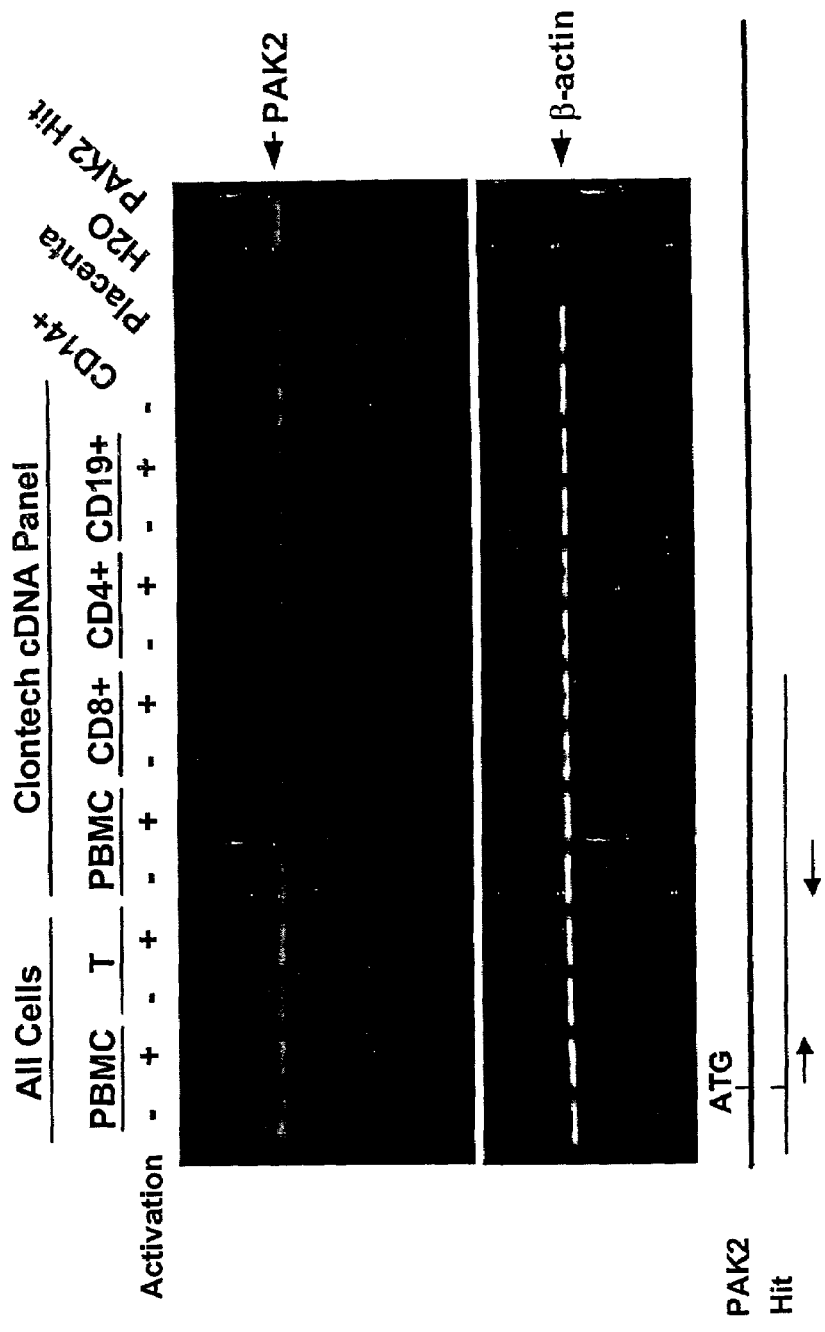
FIG. 19B shows PAK2 mRNA expression in primary lymphocytes.
Figure 20A:
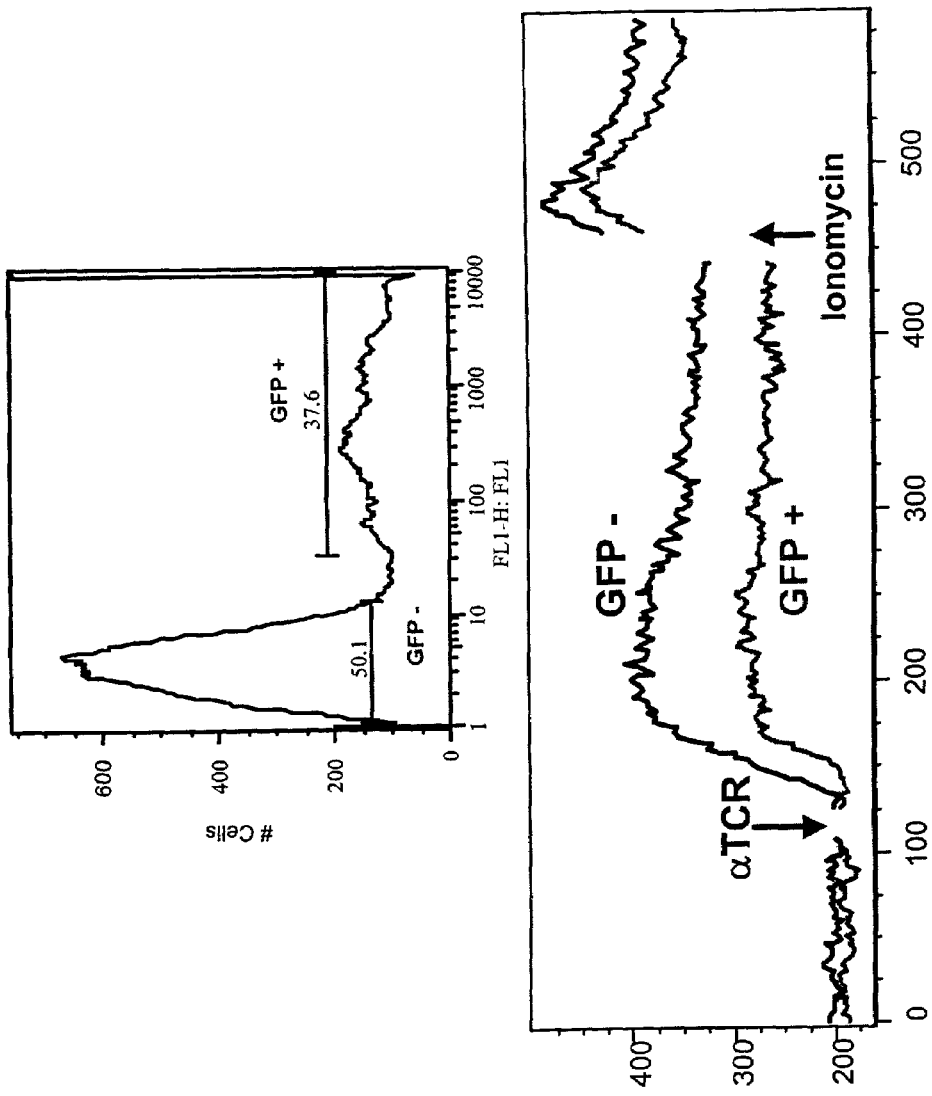
FIG. 20A shows that PAK2ΔL inhibits calcium influx.
Figure 20B:
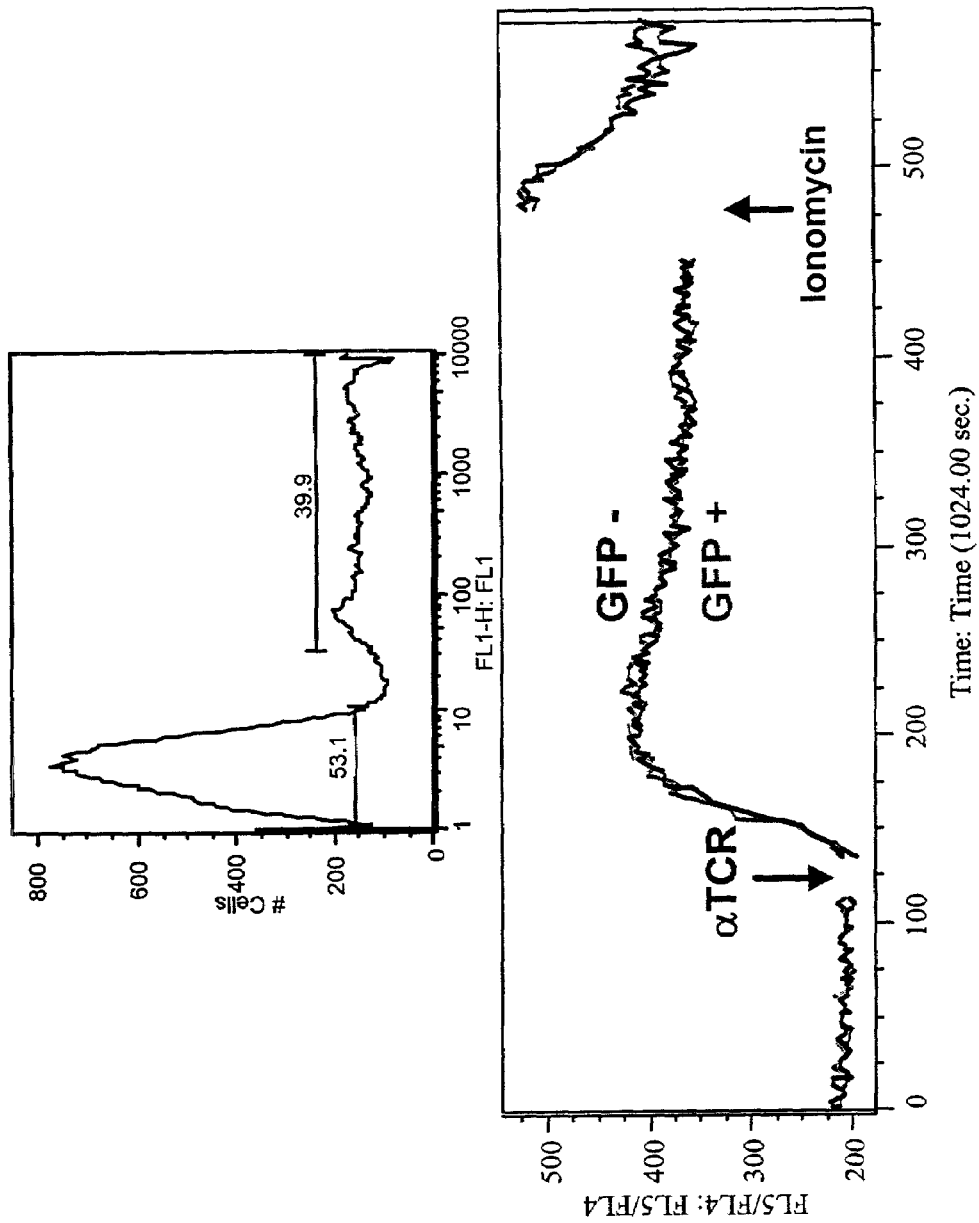
FIG. 20B shows the vector control for calcium influx.
Figure 21:
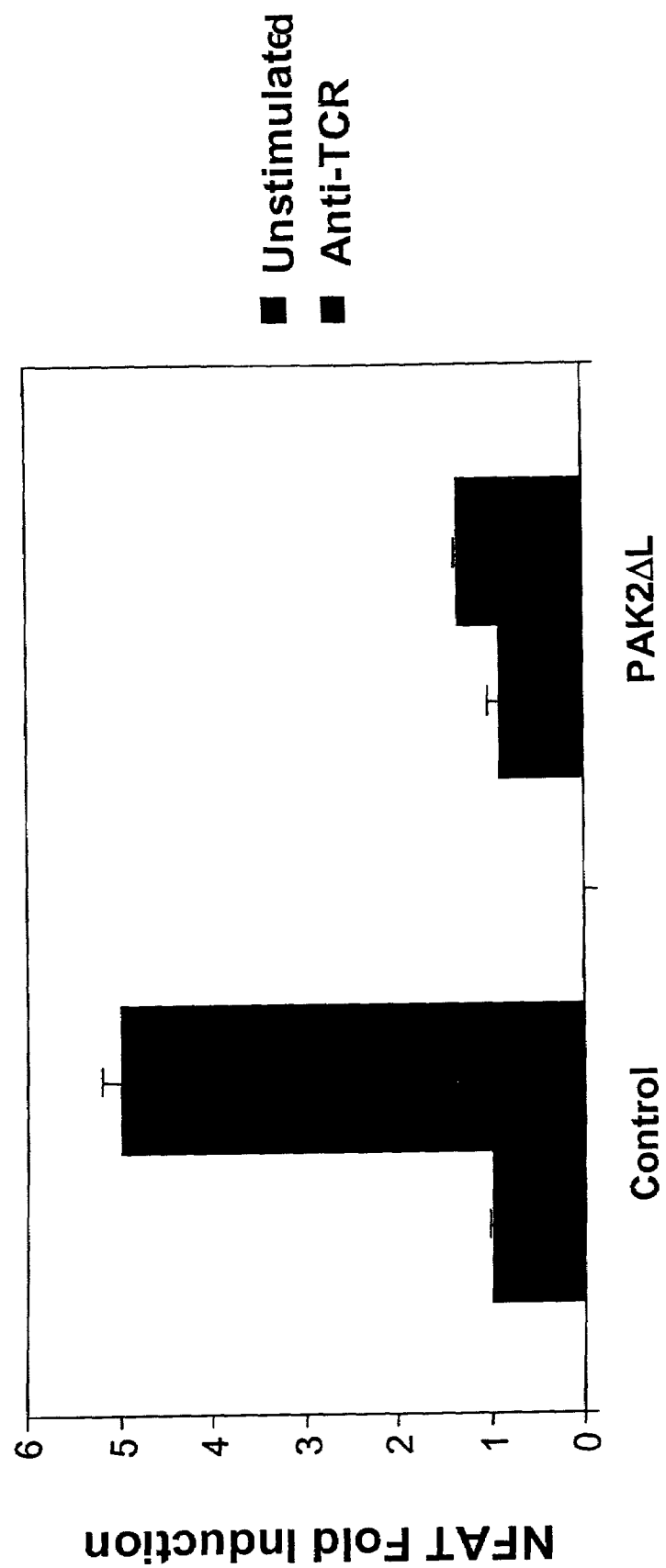
FIG. 21 shows that PAK2ΔL inhibits NFAT activation.
Figure 22:
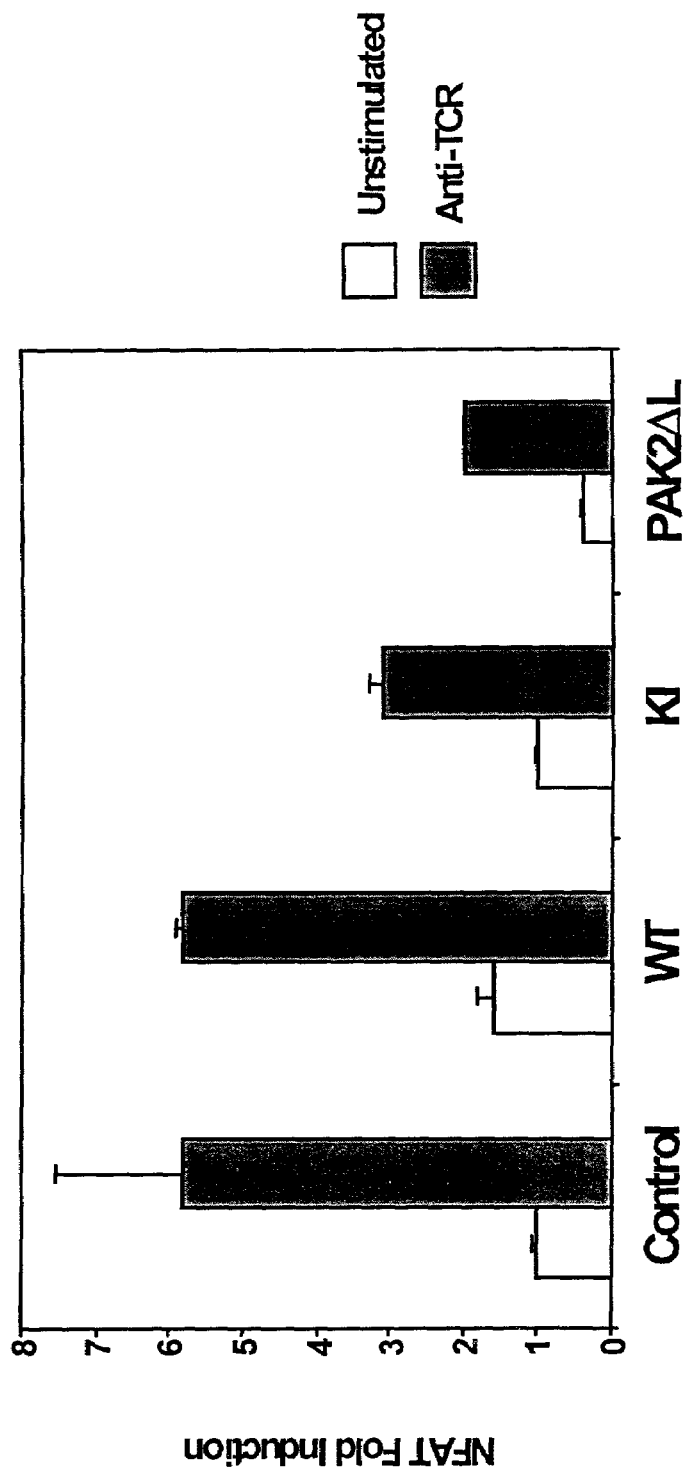
FIG. 22 shows that PAK2 kinase activity is required for TCR-induced NFAT activation.
Figure 23A:
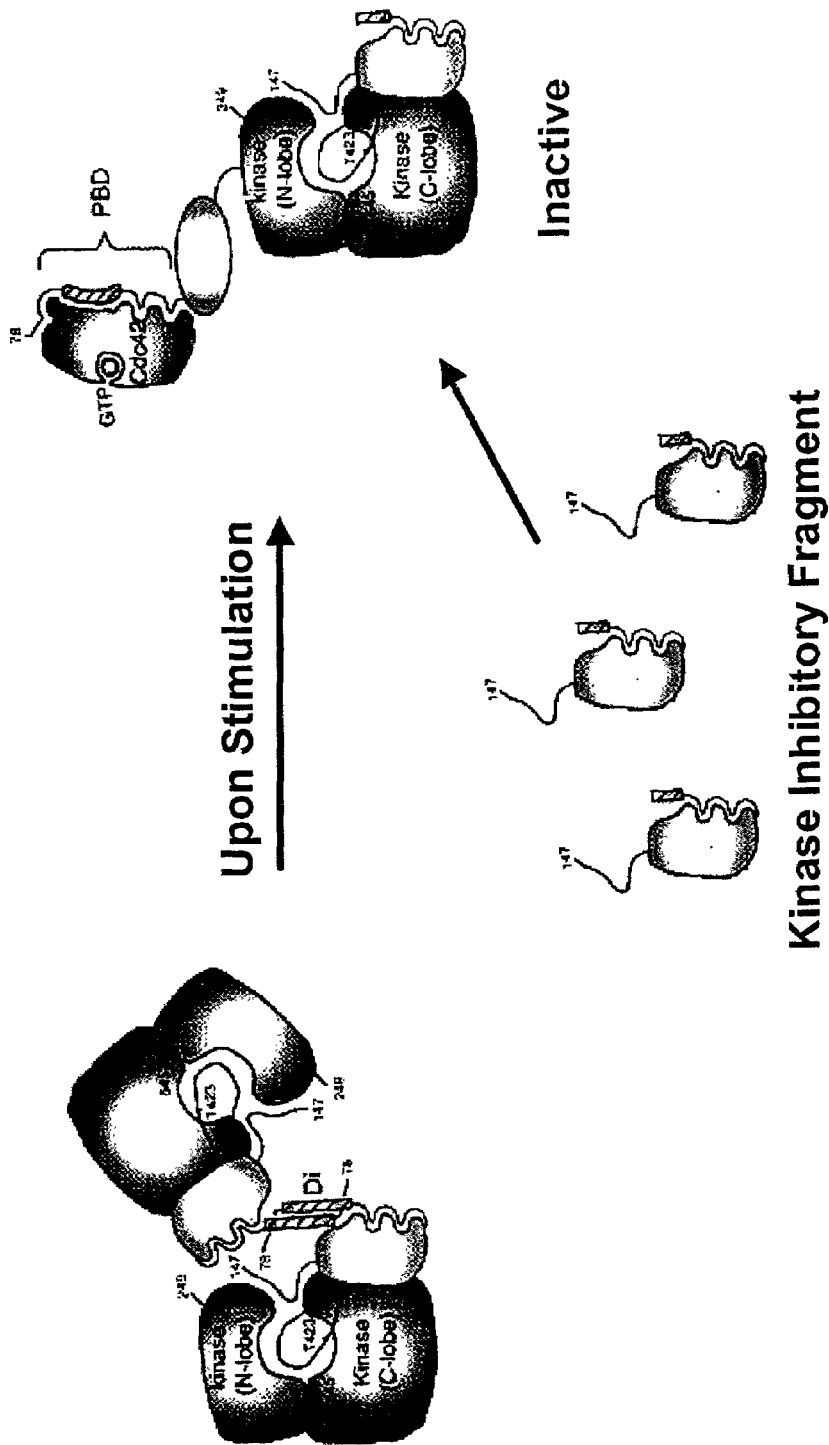
FIG. 23A shows a model for a trans-dominant fragment directly inhibiting the kinase domain.
Figure 23B:
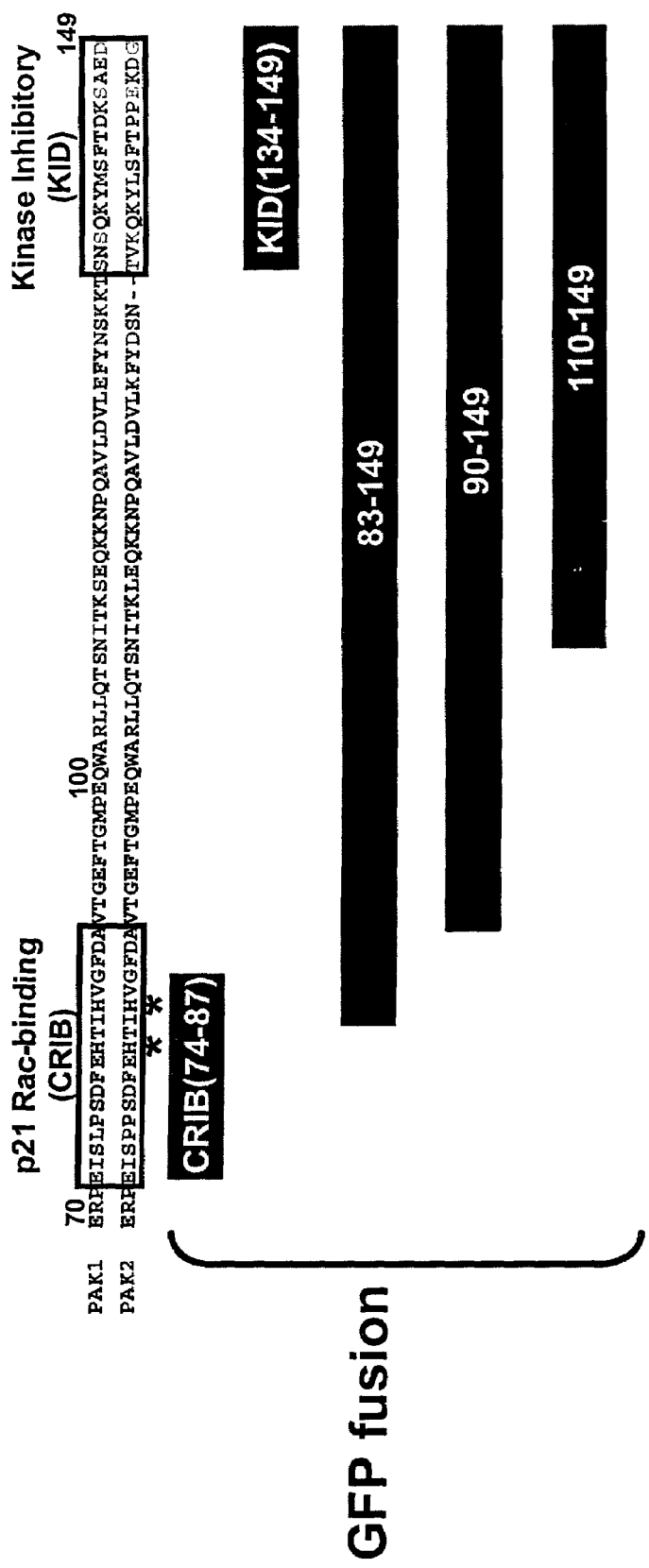
FIG. 23B shows generation of a kinase inhibitory segment (PAK1=SEQ ID NO:17; PAK2=SEQ ID NO:18).
Figure 24A:
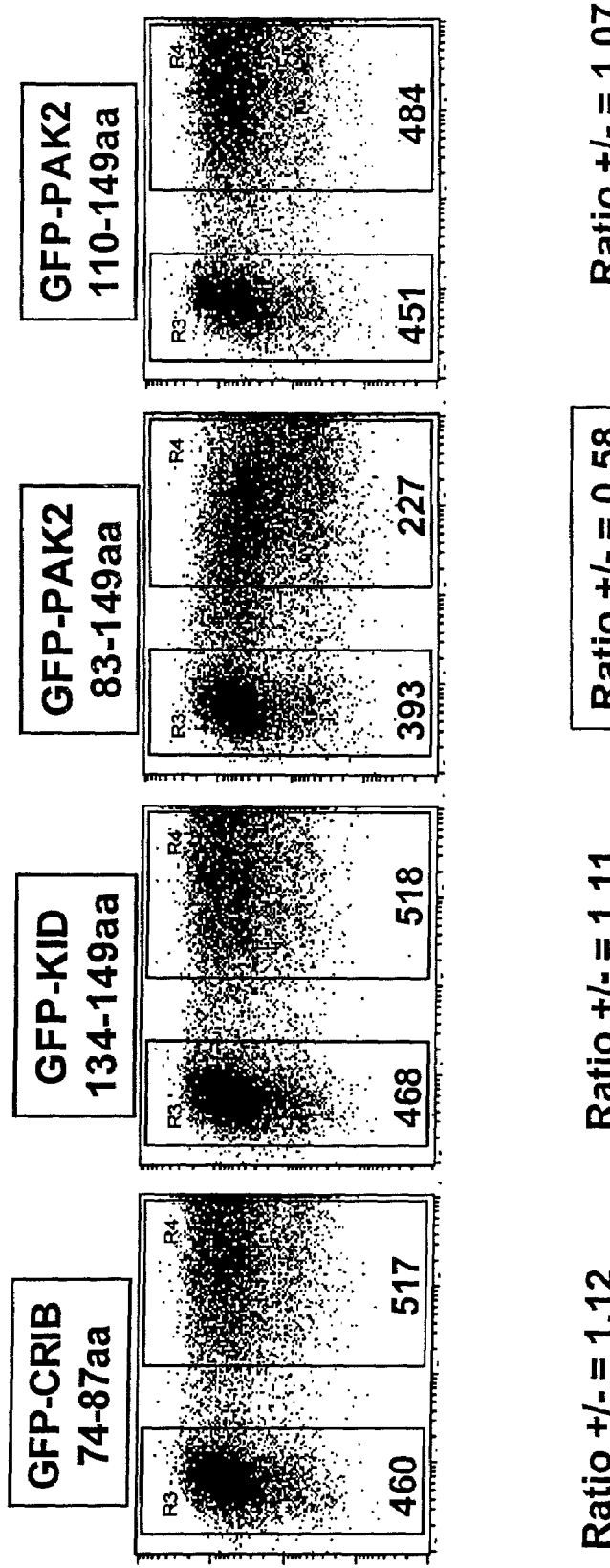
FIG. 24A shows the effect of GFP-PAK2 fragments on CD69.
Figure 24B:
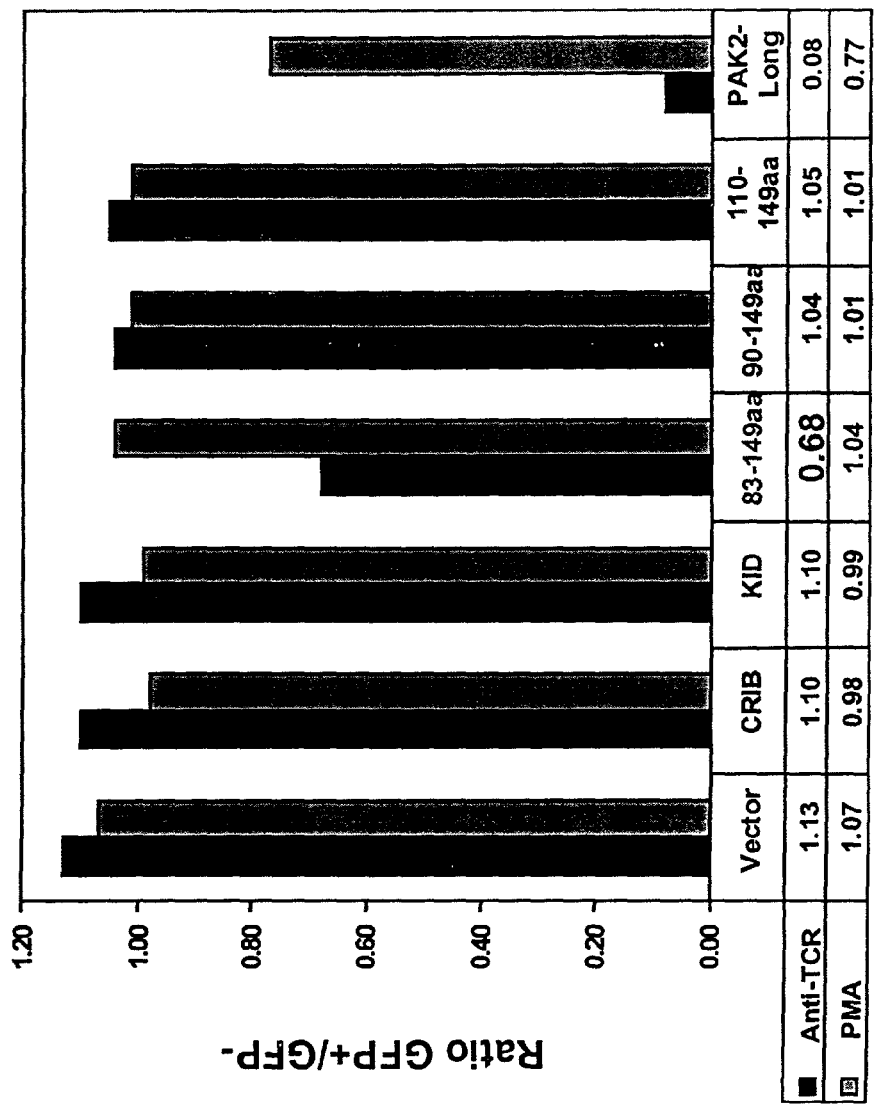
FIG. 24B shows the effect of GFP-PAK2 fragments on Jurkat TAg CD69 (ratio of GFP).
Figure 26:
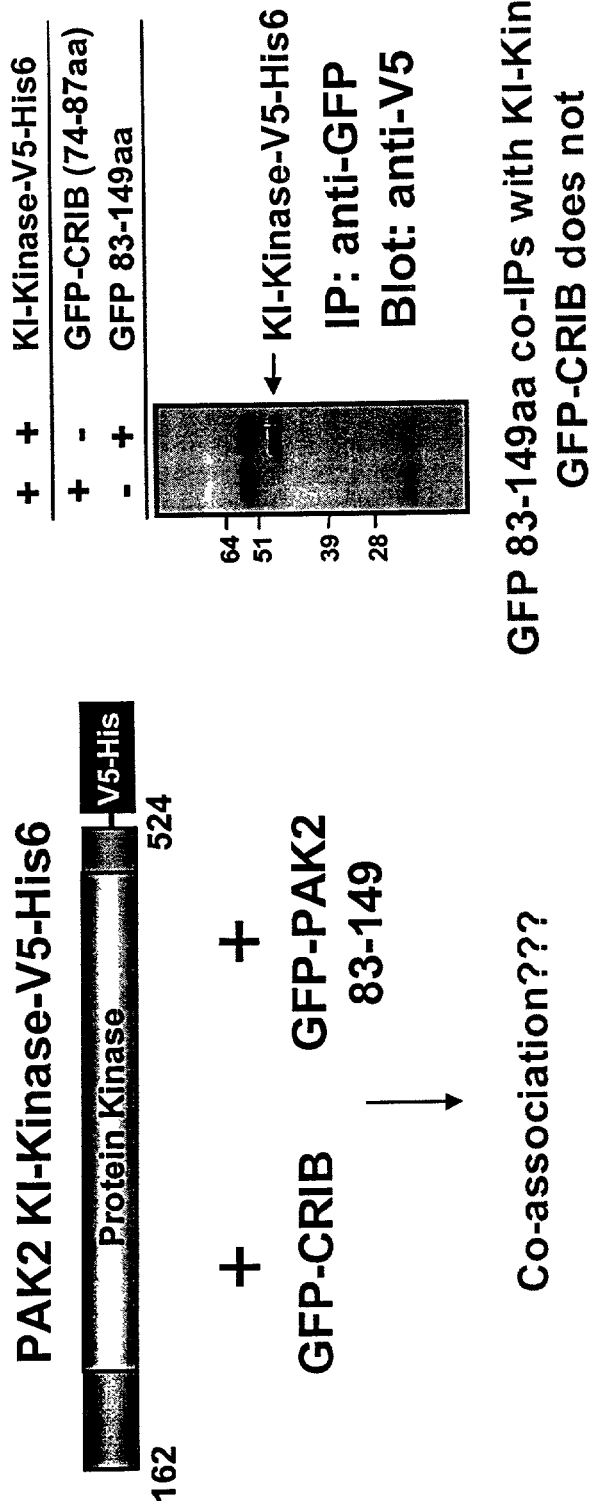
FIG. 26 shows that the tranx-dominant GFP-PAK2 fragment coimmunoprecipitates with the kinase domain.

A protein from the PAK ("p21 activated kinase") family has been functionally identified as a protein involved in regulating T lymphocyte activation and TCR signaling. PAK2 was identified in a functional genetic screen using CD69 as a readout of T cell activation. Nucleic acids encoding mutant variants of PAK2 (SEQ ID NOS:3–4) were recovered as inhibitors of T cell activation-induced CD69 expression. Mutant PAK2 expression in Jurkat cells results in inhibition of TCR induced CD69 upregulation, calcium influx, and NFAT activatiaon. Mutant PAK2 expression also inhibited receptor-mediated IL-2 production and CD40L upregulation in human primary lymphocytes. Peptides and fragments of the kinase domain can be used to bind to and inhibit the kinase domain. These fragments inhibit TCR-induced NFAT activation and CD69 activation. The present application also demonstrates that PAK2 is involved in the TCR signaling pathway. These results indicate that PAK2 modulators can be used for inhibition of TCR signaling and lymphocyte activation.

PAK family proteins ("p21-activating kinases") are serine/threonine kinases of the ste20 subfamily that act as GTPase effectors, serving as targets for small GTP-binding proteins such as Cdc42 and Rac. PAK family proteins also bind and/or phosphorylate histones H2B and H4, PIXs, MLCK, and paxillin. PAK family proteins have been implicated in a number of biological activities, including cytoskeletal reorganization and nuclear signaling following stimulation of various receptors (see, e.g., Bagrodia & Cerione, Trends Cell Biol. 9:350–355 (1999)). The family includes PAK1, PAK2, PAK3 and PAK4.

Human PAK2 protein has a molecular weight of approximately 58 kDa (525 amino acids) and is encoded by a gene located on chromosome 3 (see, e.g., Martin et al., EMBO J. 14:1970–1978 (1995); Martin et al., EMBO J. 14:4385 (1995); Manser et al., J. Biol. Chem. 270:25070–25078 (1995); and Knaus et al., Science 269:221–223 (1995)). PAK2 mRNA is ubiquitously expressed and appears to be alternatively spliced, 30 with transcripts of 7.5 kb, 5 kb, 4.4 kb, and 3 kb detected in most tissues. Jurkat cells express PAK2 protein, and in these cells, PAK2 protein is activated by proteolytic cleavage during caspase-mediated apoptosis (see, e.g., Rudel & Bokock, Science 276:1571–1574 (1997); Bokoch, Cell Death Differ. 5:637–645 (1998)). PAK11 was previously implicated in TCR signaling (Ku et al., EMBO J. 20:457–465 (2001)). A highly conserved HIV protein, NEF, is specifically associated with PAK2 but not PAK1, and NEF is known to interfere with CD3 signaling in T cells (Renkema et al., Curr. Biol. (2000), Renkema et al., J Virol. (2001); Luria et al., Proc. Nat'l Acad. Sci USA 88:5326–5330 (1991)). Despite these features, the biological function of PAK2 is not well understood.

The present invention identifies PAK2 as a member of the TCR signaling pathway. The present invention, therefore, has functionally identified PAK2 as drug targets for compounds that suppress or activate T lymphocyte activation, preferably T lymphocyte activation, e.g., for the treatment of diseases in which modulation of the immune response is desired, e.g., for treating diseases related to T lymphocyte activation, such as delayed type hypersensitivity reactions; asthma; allergies; autoimmune diseases such as scleroderma, pernicious anemia, multiple sclerosis, myasthenia gravis, IDDM, rheumatoid arthritis, systemic lupus erythematosus, and Crohn's disease; and conditions related to organ and tissue transplant, such as graft vs. host disease; and acute and chronic inflammation; as well as in diseases in which activation of the immune response is desired, e.g., in immunocompromised subjects, e.g., due to HIV infection or cancer; and in infectious disease caused by viral, fungal, protozoal, and bacterial infections. Preferably, modulators are compounds that inhibit PAK2 and thereby inhibit T cell activation.

Definitions

By "disorder associated with T lymphocyte activation" or "disease associated with lymphocyte activation" herein is meant a disease state which is marked by either an excess or a deficit of T cell activation, including TCR signaling. For example, lymphocyte activation disorders associated with increased activation include, but are not limited to, acute and chronic inflammation, asthma, allergies, autoimmune disease and transplant rejection. Pathological states for which it may be desirable to increase lymphocyte activation include HIV infection that results in immunocompromise, cancer, and infectious disease such as viral, fungal, protozoal, and bacterial infections.

The terms "PAK2" protein or fragment thereof, or a nucleic acid encoding "PAK2" or a fragment thereof refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99%. or greater amino acid sequence identity, preferably over a region of over a region of at least about 25, 50, 100, 200, 500, 1000, or more amino acids, to an amino acid sequence encoded by a PAK2 nucleic acid (SEQ ID NO:1) or amino acid sequence of a PAK2 protein (SEQ ID NO:2); (2) specifically bind to antibodies, e.g., polyclonal antibodies, raised against an immunogen comprising an amino acid sequence of a PAK2 protein (SEQ ID NO:2), immunogenic fragments thereof, and conservatively modified variants thereof; (3) specifically hybridize under stringent hybridization conditions to an anti-sense strand corresponding to a nucleic acid sequence encoding a PAK2 protein (SEQ ID NO:1), and conservatively modified variants thereof; (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides,to a PAK2 nucleic acid (SEQ ID NO:1).

A PAK2 polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Exemplary nucleic acid and protein sequences for human PAK2 are provided by GenBank Accession Nos. NM_002577, NP_002568.1, XM_039354, U25975.1, and AF092132 (see also FIGS. 2 and 18, which provide exemplary nucleotide and amino acid sequences for human PAK2). As described herein, PAK2 proteins have serine/threonine kinase activity, which can be assayed using standard methodology known to those of skill in the art (see, e.g., Manseretal., J. Biol. Chem. 270:25070–25078 (1995)).

The phrase "functional effects" in the context of assays for testing compounds that modulate activity of a PAK2 protein includes the determination of a parameter that is indirectly or directly under the influence of PAK2, e.g., an indirect, chemical or phenotypic effect such as inhibition of T lymphocyte activation represented by a change in expression of a cell surface marker or cytokine production upon TCR stimulation, or changes in cellular proliferation or apoptosis, serine/threonine kinase activity, or TCR signal transduction leading to increases in intracellular calcium or calcium influx; or, e.g., a direct, physical effect such as ligand binding or inhibition of ligand binding to PAK2 or a PAK2 domain such as the kinase or crib domain. A functional effect therefore includes ligand binding activity, the ability of cells to proliferate, apoptosis, gene expression in cells undergoing activation, serine/threonine kinase activity, expression of cell surface molecules such as CD69, CD40L and NFAT, TCR signal transduction, including downstream effectors such as second messengers, intracellular calcium release and calcium influx, production of cytokines such as IL-2, and other characteristics of activated lymphocytes. "Functional effects" include in vitro, in vivo, and ex vivo activities.

By "determining the functional effect" is meant assaying for a compound that increases or decreases a parameter that is indirectly or directly under the influence of PAK2 protein, e.g., measuring physical and chemical or phenotypic effects.

Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity, e.g., GTPase binding, e.g., Cdc42/Rac or analogs thereof, either naturally occurring or synthetic; measuring cellular proliferation; measuring apoptosis; measuring cell surface marker expression, e.g., CD69, CD40L and NFAT; measuring cytokine, e.g., IL-2, production; measurement of changes in protein levels for PAK2-associated sequences; measurement of RNA stability; phosphorylation or dephosphorylation; serine/threonine kinase activity; TCR signal transduction and downstream effectors, e.g., receptor-ligand interactions, second messenger concentrations (e.g., cAMP, IP3, or intracellular $Ca^{2+}$); calcium influx; identification of downstream or reporter gene expression (CAT, luciferase, β-gal, GFP and the like), e.g., via chemiluminescence, fluorescence, calorimetric reactions, antibody binding, inducible markers, and ligand binding assays.

"Inhibitors", "activators", and "modulators" of PAK2 polynucleotide and polypeptide sequences are used to refer to activating, inhibitory, or modulating molecules identified using in vitro and in vivo assays of PAK2 polynucleotide and polypeptide sequences. Inhibitors are compounds that, e.g., bind to, partially or totally block activity, decrease, prevent, delay activation, inactivate, desensitize, or down regulate the activity or expression of PAK2 proteins, e.g., antagonists. "Activators" are compounds that increase, open, activate, facilitate, enhance activation, sensitize, agonize, or up regulate PAK2 protein activity. Inhibitors, activators, or modulators also include genetically modified versions of PAK2 proteins, e.g., versions with altered activity, as well as naturally occurring and synthetic ligands, antagonists, agonists, peptides, cyclic peptides, nucleic acids, antibodies, antisense molecules, ribozymes, small organic molecules and the like. Such assays for inhibitors and activators include, e.g., expressing PAK2 protein in vitro, in cells, cell extracts, or cell membranes, applying putative modulator compounds, and then determining the functional effects on activity, as described above.

Samples or assays comprising PAK2 proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of PAK2 is achieved when the activity value relative to the control is about 80%, preferably 50%, more preferably 25–0%. Activation of PAK2 is achieved when the activity value relative to the control (untreated with activators) is 110%, more preferably 150%, more preferably 200–500% (i.e., two to five fold higher relative to the control), more preferably 1000–3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid (e.g., a sphingolipid), fatty acid, polynucleotide, oligonucleotide, etc., to be tested for the capacity to directly or indirectly modulation lymphocyte activation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., a nucleotide sequence of SEQ ID NO:1), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50–100 amino acids or nu For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.-2 min., and an extension phase of about 72° C. for 1–2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of antibodies, e.g., recombinant, monoclonal, or polyclonal antibodies, many technique known in the art can be used (see, e.g., Kohler & Milstein, *Nature* 256:495–497 (1975); Kozbor et al., *Immunology Today* 4: 72 (1983); Cole et al., pp.77–96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies. Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. Nos. 4,946, 778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., *Bio/Technology* 10:779–783 (1992); Lonberg et al., *Nature* 368:856–859 (1994); Morrison, *Nature* 368:812–13 (1994); Fishwild et al., *Nature Biotechnology* 14:845–51 (1996); Neuberger, *Nature Biotechnology* 14:826 (1996); and Lonberg & Huszar, *Intern.*

*Rev. Immunol.* 13:65–93 (1995)). Alternatively, phage display technology can be used to identify antibodies and heteromeric Fab fragments that specifically bind to selected antigens (see, e.g., McCafferty et al, *Nature* 348:552–554 (1990); Marks et al., *Biotechnology* 10:779–783 (1992)). Antibodies can also be made bispecific, i.e., able to recognize two different antigens (see, e.g., WO 93/08829, Traunecker et al., *EMBO J.* 10:3655–3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522–525 (1986); Riechmann et al., *Nature* 332: 323–327 (1988); Verhoeyen et al., *Science* 239:1534–1536 (1988) and Presta, *Curr. Op. Struct. Biol.* 2:593–596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to PAK2 protein as encoded by SEQ ID NOS:1, 3 and 4, polymorphic variants, alleles, orthologs, and conservatively modified variants, or splice variants, or portions thereof, can be selected to obtain only those polyclonal antibodies that are specifically immunoreactive with PAK2 proteins and not with other proteins.

This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). that is selected for its specificity for a particular protein. For example, polyclonal antibodies raised to PAK2 protein as encoded by SEQ ID NO:1–4, polymorphic variants, alleles, orthologs, and conservatively modified variants, or splice variants, or portions thereof, can be selected to obtain only those polyclonal antibodies that are specifically immunoreactive with PAK2 proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1–3, 1992); Lloyd, *The Art, Science and Technology of Pharmaceutical Compounding* (1999); and Pickar, *Dosage Calculations* (1999)).

Assays for Proteins that Modulation T Lymphocyte Activation

High throughput functional genomics assays can be used to identify modulators of T lymphocyte activation. Such assays can monitor changes in cell surface marker expression, cytokine production, antibody production, proliferation and differentiation, and apoptosis, using either cell lines or primary cells. Typically, the lymphocytes are contacted with a cDNA, a random peptide library (encoded by nucleic acids), or a cyclic peptide library (see, e.g., U.S. Pat. No. 6,153,380). The cDNA library can comprise sense, antisense, full length, and truncated cDNAs. The peptide library (optionally cyclic peptides) is encoded by nucleic acids. The lymphocytes are then activated, e.g., by activating the T cell receptor (TCR, also known as CD3), e.g., using antibodies to the receptor. The effect of the cDNA or peptide library on the phenotype of lymphocyte activation is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the peptide or with the protein encoded by the cDNA (e.g., PAK2) can be isolated using a yeast two-hybrid system, mammalian two hybrid system, or phage display screen, etc. Targets so identified can be further used as bait in these assays to identify additional members of the lymphocyte activation pathway, which members are also targets for drug development (see, e.g., Fields et al., *Nature* 340:245 (1989); Vasavada et al., *Proc. Nat'l. Acad. Sci. USA* 88:10686 (1991); Fearon et al., *Proc. Nat'l. Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637,463).

Suitable T cell lines include Jurkat, HPB-ALL, HSB-2, and PEER, as well as other mature and immature T cell lines and primary T cells known to those of skill in the art. Suitable T cell surface markers include MHC class II, CD2, CD3, CD4, CD5, CD8, CD25, CD28, CD69, CD40L, LFA-1, and ICAM-1 as well as other cell surface markers known to those of skill in the art (see, e.g., Yablonski et al., *Science* 281:413–416 (1998)). Suitable cytokines, for measuring either production or response, include IL-2, IL-4, IL-5, IL-6, IL-10, INF-γ, and TGF-β, as well as their corresponding receptors.

Cell surface markers can be assayed using fluorescently labeled antibodies and FACS. Cell proliferation can be measured using $^3$H-thymidine or dye inclusion. Apoptosis can be measured using dye inclusion, or by assaying for DNA laddering or increases in intracellular calcium. Cytokine production can be measured using an immunoassay such as ELISA.

cDNA libraries are made from any suitable source, preferably from primary human lymphoid organs such as thymus, spleen, lymph node, and bone marrow. Libraries encoding random peptides are made according to techniques well known to those of skill in the art (see, e.g., U.S. Pat. No. 6,153,380, 6,114,111, and 6,180,343). Any suitable vector can be used for the cDNA and peptide libraries, including, e.g., retroviral vectors.

In a preferred embodiment, target proteins that modulate T cell activation are identified using a high throughput cell based assay (using a microtiter plate format) and FACS screening for CD69 cell surface expression (see Example I). cDNA libraries are made from primary lymphocyte organs. These cDNA libraries include, e.g., sense, antisense, full length, and truncated cDNAs. The cDNAs are cloned into a retroviral vector with a tet-regulatable promoter. Jurkat cells are infected with the library, the cells are stimulated with anti-TCR antibodies, and then the cells are sorted using fluorescent antibodies and FACS for CD69 low/CD3+ cells. Cells with the desired phenotype are recovered, expanded, and cloned. A Tet-regulatable phenotype is established to distinguish somatic mutations. The cDNA is rescued. Optionally, the phenotype is validated by assaying for IL-2 production using primary lymphocytes. Optionally, a marker such as GFP can be used to select for retrovirally infected cells. Using this system, cDNAs encoding PAK2 were identified as inhibitors of T cell activation.

Isolation of Nucleic Acids Encoding PAK2 Family Members

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al, eds., 1994)).

PAK2 nucleic acids, polymorphic variants, orthologs, and alleles that are substantially identical to an amino acid sequence encoded by SEQ ID NO:1, as well as other PAK2 family members, can be isolated using PAK2 nucleic acid probes and oligonucleotides under stringent hybridization conditions, by screening libraries. Alternatively, expression libraries can be used to clone PAK2 protein, polymorphic variants, orthologs, and alleles by detecting expressed homologs immunologically with antisera or purified antibodies made against human PAK2 or portions thereof.

To make a cDNA library, one should choose a source that is rich in PAK2 RNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating PAK2 nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of human PAK2 directly from mRNA, from cDNA, from genomic libraries or cDNA libraries. Degenerate oligonucleotides can be designed to amplify PAK2 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of PAK2 encoding mRNA in physiological samples, for nucleic acid sequencing, or for other purposes. Genes amplified by the PCR reaction can be purified from agarose gels and cloned into an appropriate vector.

Gene expression of PAK2 can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology, e.g., and the like.

Nucleic acids encoding PAK2 protein can be used with high density oligonucleotide array technology (e.g., GeneChip™) to identify PAK2 protein, orthologs, alleles, conservatively modified variants, and polymorphic variants in this invention. In the case where the homologs being identified are linked to modulation of T cell activation, they can be used with GeneChip™ as a diagnostic tool in detecting the disease in a biological sample, see, e.g., Gunthand et al, *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

The gene for PAK2 is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding PAK2, one typically subclones PAK2 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the PAK2 protein are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the PAK2 encoding nucleic acid in host cells. A typical expression cassette thus contains a promoter operably linked to the nucleic acid sequence encoding PAK2 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMT010/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *Proc. Nat'l Acad. Sci. USA* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 16:757–761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a PAK2 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of PAK2 protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing PAK2.

After the expression vector is introduced into the cells, the transfected cells are cultured under conditions favoring expression of PAK2, which is recovered from the culture using standard techniques identified below.

Purification of PAK2 Polypeptides

Either naturally occurring or recombinant PAK2 can be purified for use in functional assays. Naturally occurring PAK2 can be purified, e.g., from human tissue. Recombinant PAK2 can be purified from any suitable expression system.

The PAK2 protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant PAK2 protein is being purified. For example, proteins having established molecular adhesion properties can be reversible fused to the PAK2 protein. With the appropriate ligand, PAK2 protein can be selectively adsorbed to a purification column and then freed from the column in a relatively pure form. The fused protein is then removed by enzymatic activity. Finally, PAK2 protein could be purified using immunoaffinity columns.

A. Purification of PAK2 from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of PAK2 protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human PAK2 proteins are separated from other bacterial proteins by standard separation techniques, e.g., with Ni-NTA agarose resin.

Alternatively, it is possible to purify PAK2 protein from bacteria periplasm. After lysis of the bacteria, when the PAK2 protein exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying PAK2 Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the PAK2 proteins can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The PAK2 proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of PAK2 Protein

A. Assays

Modulation of a PAK2 protein, and corresponding modulation of T lymphocyte activation and TCR signaling, can be assessed using a variety of in vitro and in vivo assays, including cell-based models as described above. Such assays can be used to test for inhibitors and activators of PAK2 protein, and, consequently, inhibitors and activators of lymphocyte activation. Such modulators of PAK2 protein, which is involved in T lymphocyte activation and TCR signaling, are useful for treating disorders related to T cell activation. Modulators of PAK2 protein are tested using either recombinant or naturally occurring PAK2, preferably human PAK2.

Preferably, the PAK2 protein will have the sequence as encoded by SEQ ID NO:2 or a conservatively modified variant thereof. Alternatively, the PAK2 protein of the assay will be derived from a eukaryote and include an amino acid subsequence having substantial amino acid sequence identity to SEQ ID NO:2. Generally, the amino acid sequence identity will be at least 60%, preferably at least 65%, 70%, 75%, 80%, 85%, or 90%, most preferably at least 95%.

Measurement of lymphocyte activation or loss-of-T lymphocyte activation phenotype on PAK2 protein or cell expressing PAK2 protein, either recombinant or naturally occurring, can be performed using a variety of assays, in vitro, in vivo, and ex vivo, as described herein. A suitable physical, chemical or phenotypic change that affects activity or binding can be used to assess the influence of a test compound on the polypeptide of this invention. When the functional effects are determined using intact cells or animals, one can also measure a variety of effects such as, in the case of signal transduction, e.g., ligand binding, hormone release, transcriptional changes to both known and uncharacterized genetic markers (e.g., northern blots), changes in cell metabolism such as pH changes, serine/threonine kinase activity, and changes signal transduction such as changes in intracellular second messengers such as $Ca^{2+}$, IP3, cGMP, or cAMP; as well as changes related to lymphocyte activation, e.g., cellular proliferation, cell surface marker expression, e.g., CD69, CD40L and NFAT, cytokine production, e.g., IL2, and apoptosis.

In one preferred embodiment, described herein in Example I, measurement of CD69 activation and FACS sorting is used to identify modulators of T cell activation.

In vitro Assays

Assays to identify compounds with PAK2 modulating activity can be performed in vitro. Such assays can used full length PAK2 protein or a variant thereof (see, e.g., SEQ ID NOS:1–4), or a fragment of a PAK2 protein, such as the kinase or crib domain. Purified recombinant or naturally occurring PAK2 protein or fragments thereof can be used in the in vitro methods of the invention. In addition to purified PAK2 protein, the recombinant or naturally occurring PAK2 protein can be part of a cellular lysate. As described below, the assay can be either solid state or soluble. Preferably, the protein is bound to a solid support, either covalently or non-covalently. Often, the in vitro assays of the invention are ligand binding or ligand affinity assays, either non-competitive or competitive (with known ligands such as Cdc42/Rac). Other in vitro assays include measuring changes in spectroscopic (e.g., fluorescence, absorbance, refractive index), hydrodynamic (e.g., shape), chromatographic, or solubility properties for the protein. In one embodiment, the in vitro assay measures PAK2 serine/threonine kinase activity.

In one embodiment, a high throughput binding assay is performed in which the PAK2 protein or a fragment thereof such as a crib or kinase domain is contacted with a potential modulator and incubated for a suitable amount of time. In one embodiment, the potential modulator is bound to a solid support, and the PAK2 protein is added. In another embodiment, the PAK2 protein is bound to a solid support. A wide variety of modulators can be used, as described below, including small organic molecules, peptides, antibodies, and PAK2 ligand analogs. A wide variety of assays can be used to identify PAK2-modulator binding, including labeled protein-protein binding assays, electrophoretic mobility shifts, immunoassays, enzymatic assays such as phosphorylation assays, and the like. In some cases, the binding of the candidate modulator is determined through the use of competitive binding assays, where interference with binding of a known ligand is measured in the presence of a potential modulator. Ligands for PAK2 family are known (e.g., Cdc42/Rac). Either the modulator or the known ligand is bound first, and then the competitor is added. After the PAK2 protein is washed, interference with binding, either of the potential modulator or of the known ligand, is determined. Often, either the potential modulator or the known ligand is labeled.

Cell-Based in vivo Assays

In another embodiment, PAK2 protein is expressed in a cell, and functional, e.g., physical and chemical or phenotypic, changes are assayed to identify PAK2 and lymphocyte activation modulators. Cells expressing PAK2 proteins can also be used in binding assays. Any suitable functional effect can be measured, as described herein. For example, ligand binding, cell surface marker expression, cellular proliferation, apoptosis, cytokine production, serine/threonine kinase activity, and GTPase binding, are all suitable assays to identify potential modulators using a cell based system. Suitable cells for such cell based assays include both primary lymphocytes and cell lines, as described herein. The PAK2 protein can be naturally occurring or recombinant.

As described above, in one embodiment, lymphocyte activation is measured by contacting T cells comprising a PAK2 target with a potential modulator and activating the cells with an anti-TCR antibody. Modulation of T cell activation is identified by screening for cell surface marker expression, e.g., CD69 expression levels, using fluorescent antibodies and FACS sorting.

In another embodiment, cellular proliferation or apoptosis can be measured using $^3$H-thymidine incorporation or dye inclusion. Cytokine production can be measured using an immunoassay such as an ELISA.

In another embodiment, cellular PAK2 polypeptide levels are determined by measuring the level of protein or mRNA. The level of PAK2 protein or proteins related to PAK2 signal transduction are measured using immunoassays such as western blotting, ELISA and the like with an antibody that selectively binds to the PAK2 polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Signal transduction related to TCR signaling can also be measured. Activated or inhibited TCR signaling will alter the properties of target enzymes, second messengers, channels, and other effector proteins. The examples include the activation of cGMP phosphodiesterase, adenylate cyclase, phospholipase C, IP3, and modulation of diverse channels. Downstream consequences can also be examined such as generation of diacyl glycerol and IP3 by phospholipase C, and in turn, for calcium mobilization by IP3. For example, changes in $Ca^{2+}$ levels are optionally measured using fluorescent $Ca^{2+}$ indicator dyes and fluorometric imaging.

Alternatively, PAK2 expression can be measured using a reporter gene system. Such a system can be devised using a PAK2 protein promoter operably linked to a reporter gene such as chloramphenicol acetyltransferase, firefly luciferase, bacterial luciferase, O-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961–964 (1997)). The reporter construct is typically transfected into a cell. After treatment with a potential modulator, the amount of reporter gene transcription, translation, or activity is measured according to standard techniques known to those of skill in the art.

Animal Models

Animal models of lymphocyte activation also find use in screening for modulators of lymphocyte activation. Similarly, transgenic animal technology including gene knockout technology, for example as a result of homologous recombination with an appropriate gene targeting vector, or gene overexpression, will result in the absence or increased expression of the PAK2 protein. When desired, tissue-specific expression or knockout of the PAK2 protein may be necessary. Transgenic animals generated by such methods find use as animal models of lymphocyte activation and are additionally useful in screening for modulators of lymphocyte activation.

Knock-out cells and transgenic mice can be made by insertion of a marker gene or other heterologous gene into the endogenous PAK2 gene site in the mouse genome via homologous recombination. Such mice can also be made by substituting the endogenous PAK2 with a mutated version of PAK2, or by mutating the endogenous PAK2, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators

The compounds tested as modulators of PAK2 protein can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of a PAK2 protein. Typically, test compounds will be small organic molecules, peptides, lipids, and lipid analogs. In one embodiment, a modulator is a trans-dominant peptide fragment of the PAK2 kinase domain, which binds to and inactivates the PAK2 kinase domain.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al, *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309–314 (1996) and PCT/US96/10287), carbohydrate libraries (see, e.g., Liang et al., *Science,* 274: 1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a PAK2 protein or a fragment thereof such as the kinase or crib domain, or a cell or tissue expressing a PAK2 protein, either naturally occurring or recombinant. In another embodiment, the invention provides solid phase based in vitro assays in a high throughput format, where the PAK2 protein or fragment thereof, such as the kinase or crib domain, is attached to a solid phase substrate. Any one of the assays described herein can be adapted for high throughput screening, e.g., ligand binding, cellular proliferation, cell surface marker flux, e.g., CD-69 screening, kinase activity, second messenger flux, e.g., $Ca^{2+}$, IP3, cGMP, or cAMP, cytokine production, etc. In one preferred embodiment, the cell-based system using CD-69 modulation and FACS assays is used in a high throughput format for identifying modulators of PAK2 proteins, and therefore modulators of T cell activation. In another preferred embodiment, the kinase domain or the crib domain of PAK2 is used in high throughput in vitro binding assays for modulators.

In the high throughput assays of the invention, either soluble or solid state, it is possible to screen up to several thousand different modulators or ligands in a single day. This methodology can be used for PAK2 proteins in vitro, or for cell-based or membrane-based assays comprising a PAK2 protein. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids (SEQ ID NO:19). Such flexible linkers are known to persons of skill in the art. For example, poly (ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Immunological Detection of PAK2 Polypeptides

In addition to the detection of PAK2 gene and gene expression using nucleic acid hybridization technology, one can also use immunoassays to detect PAK2 proteins of the invention. Such assays are useful for screening for modulators of PAK2 and lymphocyte activation, as well as for therapeutic and diagnostic applications. Immunoassays can be used to qualitatively or quantitatively analyze PAK2 protein. A general overview of the applicable technology can be found in Harlow & Lane, *Antibodies: A Laboratory Manual* (1988).

A. Production of Antibodies

Methods of producing polyclonal and monoclonal antibodies that react specifically with the PAK2 proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al, *Science* 246:1275–1281 (1989); Ward et al., *Nature* 341:544–546 (1989)).

A number of immunogens comprising portions of PAK2 protein may be used to produce antibodies specifically reactive with PAK2 protein. For example, recombinant PAK2 protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., Science 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-PAK2 proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular PAK family member, such as PAK2, or a particular PAK2 ortholog, such as human PAK2, can also be made, by subtracting out other cross-reacting PAK family members or orthologs from a species such as a non-human mammal. In this manner, antibodies that bind only to a particular PAK protein or ortholog may be obtained.

Once the specific antibodies against PAK2 protein are available, the protein can be detected by a variety of immunoassay methods. In addition, the antibody can be used therapeutically as a PAK2 modulators. For a review of immunological and immunoassay procedures, see Basic and Clinical Immunology (Stites & Terr eds., $7^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

PAK2 protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the PAK2 protein or antigenic subsequence thereof). The antibody (e.g., anti-PAK2) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled PAK2 or a labeled anti-PAK2 antibody. Alternatively, the labeling agent may be a third moiety, such a secondary antibody, that specifically binds to the antibody/PAK2 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111: 1401–1406 (1973); Akerstrom et al., *J. Immunol.* 135: 2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting PAK2 in samples may be either competitive or noncompetitive. Noncompetitive immunoassays are assays in which the amount of antigen is directly measured. In one preferred "sandwich" assay, for example, the anti-PAK2 antibodies can be bound directly to a solid substrate on which they are immobilized. These immobilized antibodies then capture PAK2 present in the test sample. PAK2 proteins thus immobilized are then bound by a labeling agent, such as a second PAK2 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of PAK2 protein present in the sample is measured indirectly by measuring the amount of a known, added (exogenous) PAK2 protein displaced (competed away) from an anti-PAK2 antibody by the unknown PAK2 protein present in a sample. In one competitive assay, a known amount of PAK2 protein is added to a sample and the sample is then contacted with an antibody that specifically binds to PAK2 protein. The amount of exogenous PAK2 protein bound to the antibody is inversely proportional to the concentration of PAK2 protein present in the sample. In a particularly preferred embodiment, the antibody is immobilized on a solid substrate. The amount of PAK2 protein bound to the antibody may be determined either by measuring the amount of PAK2 present in PAK2 protein/antibody complex, or alternatively by measuring the amount of remaining uncomplexed protein. The amount of PAK2 protein may be detected by providing a labeled PAK2 molecule.

A hapten inhibition assay is another preferred competitive assay. In this assay the known PAK2 protein is immobilized on a solid substrate. A known amount of anti-PAK2 antibody is added to the sample, and the sample is then contacted with the immobilized PAK2. The amount of anti-PAK2 antibody bound to the known immobilized PAK2 is inversely proportional to the amount of PAK2 protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a PAK2 protein can be immobilized to a solid support. Proteins (e.g., PAK2 and homologs) are added to the assay that compete for binding of the antisera to the immobilized antigen. The ability of the added proteins to compete for binding of the antisera to the immobilized protein is compared to the ability of the PAK2 protein to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a PAK2 protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the PAK2 protein that is required to inhibit 50% of binding, then the second protein is said to specifically bind to the polyclonal antibodies generated to PAK2 immunogen.

Other Assay Formats

Western blot (immunoblot) analysis is used to detect and quantify the presence of PAK2 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind PAK2. The anti-PAK2 antibodies specifically bind to the PAK2 on the solid support. These antibodies may be directly labeled or alternatively may be subsequently detected using labeled antibodies (e.g., labeled sheep anti-mouse antibodies) that specifically bind to the anti-PAK2 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., Amer. Clin. Prod. Rev. 5:34–41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize PAK2 protein, or secondary antibodies that recognize anti-PAK2.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cellular Transfection and Gene Therapy

The present invention provides the nucleic acids of PAK2 protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a PAK2 protein of the present invention, thereby mitigating the effects of absent, partial inactivation, or abnormal expression of a PAK2 gene, particularly as it relates to T cell activation. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175 (1993); Miller, *Nature* 357: 455–460 (1992); Van Brunt, *Biotechnology* 6(10): 1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1:13–26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the PAK2 protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Identification of Genes Involved in Modulation of T Cell Activation

A. Introduction

In this study, an approach to identify new targets for immune suppressive drugs is provided. It is known that following T cell activation, expression of numerous cell surface markers such as CD25, CD69, and CD40L are upregulated. CD69 has been shown to be an early activation marker in T, B, and NK cells. CD69 is a disulfide-linked dimer. It is not expressed in resting lymphocytes but appears on T, B and NK cells after activation in vitro. Its relevance as a TCR signaling outcome has been validated using T cell deficient in certain key signaling molecules such as LAT and SLP76 (Yablonski, supra). Furthermore, re-introducing SLP76 to the deficient cells results in restoration of CD69 expression. CD69 upregulation was therefore to be used to monitor TCR signal transduction. The rationale of the functional genomics screen was then to identify cell clones whose CD69 upregulation was repressed following introduction of a retroviral cDNA library. The library members conferring such repression would then represent immune modulators that function to block TCR signal transduction.

B. Results

Several T cell lines, including Jurkat, HPB-ALL, HSB-2 and PEER were tested for the presence of surface CD3, CD25, CD28, CD40L, CD69, CD95, and CD95L. Those that express CD3 were cultured with anti-CD3 or anti-TCR to crosslink the TCR and examined for the upregulation of CD69. Jurkat T cell line was selected for its ability to upregulate CD69 in response to crosslinking of their TCR with a kinetics mimicking that of primary T lymphocytes (data not shown). The population of Jurkat cells was sorted for low basal and highly inducible CD69 expression following anti-TCR stimulation. Clone 4D9 was selected because CD69 in this clone was uniformly and strongly induced following TCR stimulation in 24 hours.

In order to regulate the expression of the retroviral library, the Tet-Off system was used. Basically, cDNA inserts in the retroviral library were cloned behind the tetracycline regulatory element (TRE) and the minimal promoter of TK. Transcription of the cDNA inserts were then dependent on the presence of tetracycline-controlled transactivator (tTA), a fusion of Tet repression protein and the VP16 activation domain, and the absence of tetracyaline or its derivatives such as doxycycline (Dox). To shut off the cDNA expression, one can simply add doxycycline in the medium. To obtain a Jurkat clone stably expresses tTA, retroviral LTR-driven tTA was introduced in conjunction with a TRE-dependent reporter construct, namely TRA-Lyt2. Through sorting of Lyt2 positive cells in the absence of Dox and Lyt2 negative cells in the presence of Dox, coupled with clonal evaluation, a derivative of Jurkat clone 4D9 was obtained, called 4D9#32, that showed the best Dox regulation of Lyt2 expression.

Positive Controls: ZAP70 is a positive regulator of T cell activation. A kinase-inactivated (KI) ZAP70 and a truncated ZAP70 (SH2 N+C) were subcloned into the retroviral vector under TRE control. ZAP70 SH2 (N+C) and ZAP70 KI both inhibited TCR-induced CD69 expression. Consistent with the published report on dominant negative forms of ZAP70 on NFAT activity, the truncated protein is also a more potent inhibitor of CD69 induction. In addition, the higher protein expression, as shown by adjusting GFP-gating, the stronger the inhibition was. When one puts the marker M1 at bottom 1% of the uninfected cells, one has a 40% likelihood of obtaining cells whose phenotype resembled that of ZAP70 SH2 (N+C). This translates into a 40:1 enrichment of the desired phenotype.

The CD69 inhibitory phenotype is dependent on expression of dominant negative forms of ZAP70. When Dox was added for 7 days before TCR was stimulated, there was no inhibition of CD69 expression. Analysis of cellular phenotype by FACS of GFP, which was produced from the bi-cistronic mRNA ZAP70 SH2 (N+C)-IRES-GFP, revealed a lack of GFP+ cells. The lack of ZAP70 SH2 (N+C) expression in the presence of Dox was confirmed by Western.

Screening for Cells Lacking CD69 Upregulation: Jurkat 4D9#32 cells were infected with cDNA libraries made form primary human lymphoid organs such as thymus, spleen, lymph node and bone marrow. The library complexity was $5 \times 10^7$ and was built on the TRE vector. A total of $7.1 \times 10^8$ cells were screened with an infection rate of 52%, as judged by parallel infection of the same cells with TRA-dsGFP (data not shown). After infection, the cells will be stimulated with the anti-TCR antibody C305 for overnight and sorted for CD69 low and CD3+phenotype by FACS. If the sorting gate was set to include the bottom 3% cells based on the single parameter of CD69 level, 2/3 cells in the sorting gate lacked TCR/CD3 complex, which explained their refractory to stimulation. The second parameter of CD3 expression was then incorporated. Even though there was a significant reduction of CD3/TCR complex on the surface following receptor-mediated internalization, the CD3– population was still distinguishable from the CD3+ population. The resulting sort gate contained 1% of the total cells, which translated into a 100-fold enrichment based on cell numbers. The recovered cells with CD69 low CD3+ phenotype were allowed to rest in complete medium for 5 days before being stimulated again for a new round of sorting. In subsequent round of sortings, the sort gate was always maintained to contain the equivalent of 1% of the unsorted control population. Obvious enrichment was achieved after 3 rounds of reiterative sorting. Cells with the desired phenotype increased from 1% to 22.3%. In addition, the overall population's geometric mean for CD69 was also reduced.

In order to ascertain that the phenotype was due to expression of the cDNA library rather than entirely due to spontaneous or retroviral insertion-mediated somatic mutation, the cells recovered after the third round of sorting were split into two halves. One half of the cells were grown in the absence of Dox while the other half in the presence of Dox. A week later, CD69 expression was compared following anti-TCR stimulation. There was a significant numbers of cells (11%) whose CD69 repression was lost in the presence of Dox, suggesting that the CD69 inhibition phenotype was indeed caused by the expression of library members. Single cell clones in conjunction with the fourth round of CD69 low CD3+ sorting (LLLL) were deposited.

In order to reduce the number of cells whose phenotype was not Dox-regulatable, the half of the cells grown in the presence of Dox were subjected to a fourth round of sorting for enrichment of CD69 high phenotype (LLLH). The cells recovered from LLLH sort were cultured in the absence of Dox for subsequence sorting and single cell cloning of CD69 low CD3+ phenotypes.

Dox regulation of CD69 expression was expressed as the ratio of geometric mean fluorescent intensity (GMFI) in the presence of Dox over that in the absence of Dox. In uninfected cells, Dox had limited effect on the induction of CD69 expression so that the ratio of GMFI (+Dox)/GMFI (–Dox) remained to be 1.00+/–0.25. The 2× standard deviation was therefore used as a cut-off criterion and clones with a ratio above 1.5 were regarded as Dox-regulated clones.

RNA samples were prepared from clones with Dox-regulatable phenotypes. Using primers specific for the vector sequence flanking the cDNA library insert, the cDNA insert of selected clones were captured by RT-PCR. Most clones generated only on DNA band, whereas a few clones generated two or more bands. Sequencing analysis revealed that the additional bands were caused by double or multiple insertions.

Characterization of Proteins Involved in T Cell Activation: Known TCR regulators such as Lck, ZAP70, PLCγ1 and Raf were obtained. In addition, the BCR regulator SYK was also uncovered. Molecules previously not associated with TCR activation, such as PAK2, were also identified using this screen.

Lck is a non-receptor protein tyrosine kinase. Its role in T cell development and activation has been widely documented. So far, dominant negative form of Lck has no been reported. Our discovery that over expression of the kinase-truncated form of Lck caused inhibition of CD69, similar to the phenotype of Jurkat somatic mutant lacking Lck, suggests that kinase deletion of Lck could also work as a dominant negative form of Lck.

The two ZAP70 hits ended at aa 262 and 269, respectively. They both missed the catalytic domain. The deletions are very close to the positive control for the screen, ZAP70 SH2 (N+C), which ended at aa 276. Since ZAP70 SH2 (N+C) was shown to be a dominant negative protein, it appears that the two ZAP70 hits also behaved as dominant negative proteins of ZAP70.

SYK is a non-receptor tyrosine kinase belonging to the SYK/ZAP70 family of kinases. Since it has also been shown that the lack of SYK expression in Jurkat cells did not appear to significantly alter the TCR-mediated responses compared with Jurkat clones expressing SYK, it appears that the SYK hit obtained from our screen worked mainly to block ZAP70 function. SYK's similarity to ZAP70 and its ability to associate with phosphorylated TCR zeta chains also support this notion.

PLCγ1 plays a crucial role in coupling T cell receptor ligation to IL-2 gene expression in activated T lymphocytes. TCR engagement leads to rapid tyrosine phosphorylation and activation of PLCγ1. The activated enzyme converts phosphatidylinositol-4,5-bisphosphate (PIP2) to inositol-1,3,5-trisphosphate ((IP3) and diacylglycerol (DAG). IP3 triggers intracellular Ca2+ increase and DAG is a potent activator of protein kinase C (PKC). PLCγ1 has a split catalytic domain comprised of conserved X and Y subdomains. Single point mutation in the catalytic X box completely abolished the enzyme activity and also blocked IL-2 reporter gene expression when introduced into PLCγ-deficient Jurkat cells. Our hit contained the PH domain and the N and C terminal SH2 domains of PLCγ1. Significantly this hit also deleted the crucial tyrosine Y783 between the SH2 and SH3 domains. It was reported that Y783 was essential for coupling of TCR stimulation to IL-2 promoter activation and that mutation of Y783 to F (phenylalanine) generated a very potent dominant negative form of PLCγ1. Indeed, the original clone encoding the PLCγ1hit had the highest Dox +/− ratio for CD69 expression among all clones from the cDNA screen, indicating the strong repression of CD69 induction by the hit as well as the total de-repression in the absence of the hit. When introduced to naive Jurkat cells, this fragment caused severe block of TCR-induced CD69 expression.

Raf is a MAP kinase kinase kinase. It interacts with Ras and leads to activation of the MAP kinase pathway. The Raf hit obtained also had a truncation of the kinase domain, creating a dominant negative form of the kinase. Other signaling molecules known to involve in TCR pathway were also discovered in our screen. They included PAG, CSK, SHP-1 and nucleolin.

PAK2 is a serine/threonine kinase and a member of the PAK family of proteins. A cDNA encoding the Cdc24-binding domain of PAK2, but lacking the kinase domain was isolated as a functional hit using the T cell CD69 assay described herein. Another truncated form was also isolated using the same assay. Overexpression of this kinase domain-truncated form of PAK2 (DN-PAK2), as well as the second mutant, in Jurkat T cells resulted in marked inhibition of TCR mediated CD69 upregulation. The inhibitory effect by overexpressing the DN-PAK2 was specific to T cells, since it failed to affect the PCR-induced CD69 activation in BJAB cells. Introduction of the DN-PAK2 in primary T cells lead to inhibition of IL-2 secretion following TCR and CD28 stimulation. In primary T cells expressing the DN-PAK2, the TCR-induced upregulation of CD40L was compromised. Although PAK1 has been previously implicated in TCR-mediated signal transduction (see, e.g., Ku et al., *EMBO J.* 20:457–465 (1998)), the data described herein show that the anti-PAK1 antibody used in those studies cross-reacts with PAK2. Using TaqMan, the data provided herein shows that PAK2 mRNA is much more abundant than PAK1 in lymphoid cells and is abundantly expressed in human hematopoietic cells. PAK2 is also involved in the TCR signaling pathway, as stimulation of TCR enhances PAK2 kinase activity, which peaked around 5 minutes following the receptor ligation.

Function in Primary T Lymphocytes: The relevance of the CD69 screen hits to physiological function of T cells was investigated in primary T lymphocytes. The hit was subcloned into a retroviral vector under a constitutively active promoter, followed by IRES-GFP. A protocol was also developed to couple successful retroviral infection to subsequence T cell activation. Primary T lymphocytes are at the quiescent stage when isolated from healthy donors. In order to be infected by retrovirus, primary lymphocytes need to be activated to progress in cell cycle. Fresh peripheral blood lymphocytes (PBL) contained typically T cells and B cells. The combined CD4+ and CD8+ cells represented total T cell percentage, which was 81% in this particular donor. The remaining 19% CD4–CD8-cells were B cells as stained by CD19 (data not shown). Upon culturing on anti-CD3 and anti-CD28 coated dishes, primary T lymphocytes were expanded and primary B cells and other cell types gradually died off in the culture. After infection, the culture contained virtually all T cells. Furthermore, primary T lymphocytes were successfully infected by retroviruses. As seen with Jurkat cells (data not shown), GFP translated by way of IRES was not as abundant as GFP translated using the conventional Kozak sequence (comparing GFP geometric mean from CRU5-IRES-GFP and CRU5-GFP). Nevertheless the percentage infection remained similar. Insertion of a gene in front of IRES-GFP further reduced the expression level of GFP, which was observed with cell lines (data not shown) and here primary T lymphocytes. After allowing cells to rest following infection, FACS sorted cells were divided into two populations: GFP− and GFP+. The sorted cells were immediately put into culture. Anti-CD3 alone did not induce IL-2 production. This observation was consistent with previous report on freshly isolated primary T lymphocytes and confirmed the notion that prior culture and retroviral infection did not damage the physiological properties of these primary T lymphocytes. Addition of anti-CD28 in conjunction with anti-CD3 led to robust IL-2 production with vector-infected cells and the GFP− population of LckDN and PLCγ1DN-infected cells. The GFP+cell population from LckDN and PLCγ1DN-infected cells, however, were severed impaired in IL-2 production. As expect, the defect caused by LckDN and PLCγ1DN can be completely rescued by stimulation using PMA and ionomycin. Taken together, these results showed that Lck and PLCγ1 plays a role in IL-2 production from primary T lymphocytes, consistently with their involvement membrane proximal signaling events of T cell activation. These results also demonstrated a successful system to quickly validate hits from our functional genetic screens in primary cells.

Use of CD69 upregulation in drug screening: The discovery of important immune regulatory molecules from the T cell activation-induced CD69 upregulation validated the relevance of this cell-based assay. Essentially such a cell-based assay offers the opportunity to discover inhibitors of multiple targets such as Lck, ZAP70, PLCγ1 and PAK2. It is the equivalent of multiplexing enzymatic assays with the additional advantage of cell permeability of compounds. It may even be possible to identify novel compounds that block adaptor protein functions. Towards this end, the FACS assay of cell surface CD69 expression was converted to a micro-titer plate based assay.

In conclusion, the strategy presented in this study demonstrates a successful approach to discover and validate important immune regulators on a genome-wide scale. This approach, which requires no prior sequence information, provides a tool for functional cloning of regulators in numerous signal transduction pathways. For example, B cell activation-induced CD69 expression, IL-4-induced IgE class switch and TNF-induced NF-KB reporter gene expression are all amendable to the genetic perturbation following introduction of retroviral cDNA libraries. The outlined strategy is less biased compared to forced introduction of a handful of signaling molecules discovered in other context such as growth factor signal transduction. It also opens the door for discovering peptide inhibitors of immune modulatory proteins by screening random peptide libraries expressed from the retroviral vector.

C. Methods

Cell Culture: Human Jurkat T cells (clone N) were routinely cultured in RPMI 1640 medium supplemented with 10% fetal calf serum (Hyclone), penicillin and streptamycin. Phoenix A cells were grown in DMEM supplemented with 10% fetal calf serum, penicillin and streptamycin. To produce the tTA-Jurkat cell line, Jurkat cells were infected with a retroviral construct which constitutively expresses the tetracycline transactivator protein and a reporter construct which expresses LyT2 driven by a tetracycline responsive element (TRE). The tTA-Jurkat cell population was optimized by sorting multiple sounds for high TRE-dependent expression of LyT2 in the absence of Dox and strong repression of LyT2 expression in the presence Dox. The cells were also sorted for maximal anti-TCR induced expression of CD69. Doxycycline was used at a final concentration of 10 ng/ml for at least 6 days to downregulate expression of cDNAs from the TRE promoter.

Transfection and Infection: Phoenix A packaging cells were transfected with retroviral vectors using calcium phosphate for 6 hours as standard protocols. After 24 hours, supernatant was replaced with complete RPMI medium and virus was allowed to accumulate for an additional 24 hours. Viral supernatant was collected, filtered through a 0.2 μM filter and mixed with Jurkat cells at a density of $2.5 \times 10^5$ cells/ml. Cells were spun at room temperature for 3 hours at 3000 rpm, followed by overnight incubation at 37° C.

Transfection and infection efficiencies were monitored by GFP expression and functional analysis was carried out 2–4 days after infection.

Libraries: RNA extracted from human lymph node, thymus, spleen and bone marrow was used to produce two cDNA libraries; one random primed and directionally cloned and the second non-directionally cloned and provided with 3 exogenous ATG in 3 frames. cDNAs were cloned into the pTRA-exs vector giving robust doxycycline-regulable transcription of cDNAs from the TRE promoter. The total combined library complexity was $5 \times 10^7$ independent clones.

Stimulation:

For CD69 upregulation experiments, tTA-Jurkat cells were split to $2.5 \times 10^5$ cells/ml 24 hours prior to stimulation. Cells were spun and resuspended at $5 \times 10^5$ cells/ml in fresh complete RPMI medium in the presence of 100 ng/ml C305 (anti-Jurkat clonotypic TCR) or 5 ng/ml PMA hybridoma supernatant for 20–26 hours at 37° C., and then assayed for surface CD69 expression.

Cell Surface Marker Analysis: Jurkat-N cells were stained with an APC-conjugated mouse monoclonal anti-human CD69 antibody (Caltag) at 4° C. for 20 minutes and analyzed using a Facscalibur instrument (Becton Dickinson) with Cellquest software. Cell sorts were performed on a MoFlo (Cytomation).

cDNA Screen: Phoenix A packaging cells were transfected with a mixture of the two tTA regulated retroviral pTRA-exs cDNA libraries. Supernatant containing packaged viral particles was used to infect tTA-Jurkat cells with an efficiency of ~85%. After 4 days of cDNA expression, library infected cells were stimulated with 0.3 μg/ml C305 for 20–26 hours, stained with APC-conjugated anti-CD69, and lowest CD69-expressing cells still expressing CD3 ($CD69^{low}CD3^+$) were isolated using a fluorescence activated cell sorter. Sorting was repeated over multiple rounds with a 6-day rest period between stimulations until the population was significantly enriched for non-responders. Single cells were deposited from 4 separate rounds of sorting. Cell clones were expanded in the presence and absence of Dox, stimulated and analyzed for CD69 upregulation.

Isolation of cDNA inserts: PCR primers were designed to amplify cDNA inserts from both libraries and did not amplify Lyt2 that was also under TRE regulation. The primers used contained flanking BstXI sites for subsequent cloning to pTRA-IRES-GFP vector. RT-PCR cloning was achieved with kits from Clontech or Life Technologies. The gel-purified RT-PCR products were submitted for sequencing directly and simultaneously digested for subcloning. Dominant negative ZAP70 (KI) and ZAP70SH2 (N+C) as well as selected hits from cDNA screens were subcloned to the retroviral pTRA-IRES-GFP vector. Selected hits form cDNA screens were also subcloned to CRU5-IRES-GFP for infection of human primary T lymphocytes and examination of IL-2 production.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for identifying a compound that modulates PAK2-mediated T lymphocyte activation, the method comprising the steps of:
   (i) contacting a host T cell comprising a PAK2 polypeptide having serine/threonine kinase activity with the compound, the PAK2 polypeptide encoded by a nucleic acid that hybridizes under stringent conditions to the complement of the nucleic acid encoding a polypeptide having an amino acid sequence of SEQ ID NO:2, wherein the stringent conditions comprise incubating at 42° C. in a solution comprising 50% formamide, 5x SSC, and 1% SDS and washing at 65° C. in a solution comprising 0.2xSSC and 0.1% SDS;
   (ii) activating the host T cell via a T cell receptor (TCR-CD3) and determining whether the compound modulates the TCR-CD3 signaling cascade in the host T cell; and
   (iii) determining whether the compound modulates PAK2 activity, whereby modulation of PAK2 activity and modulation of TCR-CD3 signaling cascade indicates the compound modulates PAK2-mediated T lymphocyte activation.

2. The method of claim 1, wherein the host cell is a primary T lymphocyte.

3. The method of claim 1, wherein the host cell is a cultured T cell.

4. The method of claim 3, wherein the host cell is a Jurkat cell.

5. The method of claim 1, wherein modulation is inhibition of T lymphocyte activation.

6. The method of claim 1, wherein the polypeptide is recombinant.

7. The method of claim 1, wherein the PAK2 polypeptide comprises an amino acid sequence of SEQ ID NO:2.

8. The method of claim 1, wherein the PAK2 polypeptide is encoded by a nucleic acid comprising a nucleotide sequence of SEQ ID NO:1.

9. The method of claim 1, wherein the compound is a small organic molecule.

10. The method of claim 1, wherein said nucleic acid encoding a polypeptide having an amino acid sequence of SEQ ID NO:2 consists of a sequence of SEQ IDNO:1.

11. The method of claim 1, wherein the compound binds to the PAK2 polypeptide.

12. The method of claim 1, wherein modulation of the TCR-CD3 signaling cascade in the host T cell is determined by measuring a parameter selected from the group consisting of CD69 expression, NFAT expression, CD4OL expression, IL-2 production, intracellular $Ca^{2+}$ mobilization, $Ca^{2+}$ influx, and lymphocyte proliferation.

* * * * *

SEQUENCE LISTING

<160> NUMBER OF SEQ ID NOS: 19

<210> SEQ ID NO 1
<211> LENGTH: 2019
<212> TYPE: DNA
<213> ORGANISM: Homo sapiens
<220> FEATURE:
<223> OTHER INFORMATION: p21 (CDKN1A)-activated kinase 2 (PAK2) mRNA
<220> FEATURE:
<221> NAME/KEY: CDS
<222> LOCATION: (40)..(1617)
<223> OTHER INFORMATION: PAK2

<400> SEQUENCE: 1

```
gaccttggct tgcccggggc catttcataa ttctgaatc atg tct gat aac gga          54
                                            Met Ser Asp Asn Gly
                                              1               5 gaa ctg gaa gat aag cct cca gca cct cct gtg cga atg agc agc acc        102
Glu Leu Glu Asp Lys Pro Pro Ala Pro Pro Val Arg Met Ser Ser Thr
             10                  15                  20 atc ttt agc act gga ggc aaa gac cct ttg tca gcc aat cac agt ttg        150
Ile Phe Ser Thr Gly Gly Lys Asp Pro Leu Ser Ala Asn His Ser Leu
         25                  30                  35 aaa cct ttg ccc tct gtt cca gaa gag aaa aag ccc agg cat aaa atc        198
Lys Pro Leu Pro Ser Val Pro Glu Glu Lys Lys Pro Arg His Lys Ile
     40                  45                  50 atc tcc ata ttc tca ggc aca gag aaa gga agt aaa aag aaa gaa aag        246
Ile Ser Ile Phe Ser Gly Thr Glu Lys Gly Ser Lys Lys Lys Glu Lys
 55                  60                  65 gaa cgg cca gaa att tct cct cca tct gat ttt gag cac acc atc cat        294
Glu Arg Pro Glu Ile Ser Pro Pro Ser Asp Phe Glu His Thr Ile His
 70                  75                  80                  85 gtt ggc ttt gat gct gtt act gga gaa ttc act ggc atg cca gaa cag        342
Val Gly Phe Asp Ala Val Thr Gly Glu Phe Thr Gly Met Pro Glu Gln
                 90                  95                 100 tgg gct cga tta cta cag acc tcc aat atc acc aaa cta gag caa aag        390
Trp Ala Arg Leu Leu Gln Thr Ser Asn Ile Thr Lys Leu Glu Gln Lys
            105                 110                 115 aag aat cct cag gct gtg ctg gat gtc cta aag ttc tac gac tcc aac        438
Lys Asn Pro Gln Ala Val Leu Asp Val Leu Lys Phe Tyr Asp Ser Asn
        120                 125                 130 aca gtg aag cag aaa tat ctg agc ttt act cct cct gag aaa gat ggc        486
Thr Val Lys Gln Lys Tyr Leu Ser Phe Thr Pro Pro Glu Lys Asp Gly
    135                 140                 145 ctt cct tct gga acg cca gca ctg aat gcc aag gga aca gaa gca ccc        534
Leu Pro Ser Gly Thr Pro Ala Leu Asn Ala Lys Gly Thr Glu Ala Pro
150                 155                 160                 165 gca gta gtg aca gag gag gag gat gat gat gaa gag act gct cct ccc        582
Ala Val Val Thr Glu Glu Glu Asp Asp Asp Glu Glu Thr Ala Pro Pro
                170                 175                 180 gtt att gcc ccg cga ccg gat cat acg aaa tca att tac aca cgg tct        630
Val Ile Ala Pro Arg Pro Asp His Thr Lys Ser Ile Tyr Thr Arg Ser
            185                 190                 195 gta att gac cct gtt cct gca cca gtt ggt gat tca cat gtt gat ggt        678
Val Ile Asp Pro Val Pro Ala Pro Val Gly Asp Ser His Val Asp Gly
        200                 205                 210 gct gcc aag tct tta gac aaa cag aaa aag aag cct aag atg aca gat        726
Ala Ala Lys Ser Leu Asp Lys Gln Lys Lys Lys Pro Lys Met Thr Asp
    215                 220                 225 gaa gag att atg gag aaa tta aga act atc gtg agc ata ggt gac cct        774
```

|  |  |  |  |  |  |  |  |  |  |  |  |  |  |  |  |
|---|---|---|---|---|---|---|---|---|---|---|---|---|---|---|---|
| Glu | Glu | Ile | Met | Glu | Lys | Leu | Arg | Thr | Ile | Val | Ser | Ile | Gly | Asp | Pro |
| 230 |  |  |  |  | 235 |  |  |  |  | 240 |  |  |  |  | 245 |

| aag | aaa | aaa | tat | aca | aga | tat | gaa | aaa | att | gga | caa | ggg | gct | tct | ggt | 822 |
|---|---|---|---|---|---|---|---|---|---|---|---|---|---|---|---|---|
| Lys | Lys | Lys | Tyr | Thr | Arg | Tyr | Glu | Lys | Ile | Gly | Gln | Gly | Ala | Ser | Gly |  |
|  |  |  |  |  | 250 |  |  |  |  | 255 |  |  |  |  | 260 |  |

| aca | gtt | ttc | act | gct | act | gac | gtt | gca | ctg | gga | cag | gag | gtt | gct | atc | 870 |
|---|---|---|---|---|---|---|---|---|---|---|---|---|---|---|---|---|
| Thr | Val | Phe | Thr | Ala | Thr | Asp | Val | Ala | Leu | Gly | Gln | Glu | Val | Ala | Ile |  |
|  |  |  |  | 265 |  |  |  |  | 270 |  |  |  |  | 275 |  |  |

| aaa | caa | att | aat | tta | cag | aaa | cag | cca | aag | aag | gaa | ctg | atc | att | aac | 918 |
|---|---|---|---|---|---|---|---|---|---|---|---|---|---|---|---|---|
| Lys | Gln | Ile | Asn | Leu | Gln | Lys | Gln | Pro | Lys | Lys | Glu | Leu | Ile | Ile | Asn |  |
|  |  |  | 280 |  |  |  |  | 285 |  |  |  |  | 290 |  |  |  |

| gag | att | ctg | gtg | atg | aaa | gaa | ttg | aaa | aat | ccc | aac | atc | gtt | aac | ttt | 966 |
|---|---|---|---|---|---|---|---|---|---|---|---|---|---|---|---|---|
| Glu | Ile | Leu | Val | Met | Lys | Glu | Leu | Lys | Asn | Pro | Asn | Ile | Val | Asn | Phe |  |
|  | 295 |  |  |  |  | 300 |  |  |  |  | 305 |  |  |  |  |  |

| ttg | gac | agt | tac | ctg | gta | gga | gat | gaa | ttg | ttt | gtg | gtc | atg | gaa | tac | 1014 |
|---|---|---|---|---|---|---|---|---|---|---|---|---|---|---|---|---|
| Leu | Asp | Ser | Tyr | Leu | Val | Gly | Asp | Glu | Leu | Phe | Val | Val | Met | Glu | Tyr |  |
| 310 |  |  |  |  | 315 |  |  |  |  | 320 |  |  |  |  | 325 |  |

| ctt | gct | ggg | ggg | tca | ctc | act | gat | gtg | gta | aca | gaa | aca | gct | tgc | atg | 1062 |
|---|---|---|---|---|---|---|---|---|---|---|---|---|---|---|---|---|
| Leu | Ala | Gly | Gly | Ser | Leu | Thr | Asp | Val | Val | Thr | Glu | Thr | Ala | Cys | Met |  |
|  |  |  |  | 330 |  |  |  |  | 335 |  |  |  |  | 340 |  |  |

| gat | gaa | gca | cag | att | gct | gct | gta | tgc | aga | gag | tgt | tta | cag | gca | ttg | 1110 |
|---|---|---|---|---|---|---|---|---|---|---|---|---|---|---|---|---|
| Asp | Glu | Ala | Gln | Ile | Ala | Ala | Val | Cys | Arg | Glu | Cys | Leu | Gln | Ala | Leu |  |
|  |  |  | 345 |  |  |  |  | 350 |  |  |  |  | 355 |  |  |  |

| gag | ttt | tta | cat | gct | aat | caa | gtg | atc | cac | aga | gac | atc | aaa | agt | gac | 1158 |
|---|---|---|---|---|---|---|---|---|---|---|---|---|---|---|---|---|
| Glu | Phe | Leu | His | Ala | Asn | Gln | Val | Ile | His | Arg | Asp | Ile | Lys | Ser | Asp |  |
|  |  | 360 |  |  |  |  | 365 |  |  |  |  | 370 |  |  |  |  |

| aat | gta | ctt | ttg | gga | atg | gaa | gga | tct | gtt | aag | ctc | act | gac | ttt | ggt | 1206 |
|---|---|---|---|---|---|---|---|---|---|---|---|---|---|---|---|---|
| Asn | Val | Leu | Leu | Gly | Met | Glu | Gly | Ser | Val | Lys | Leu | Thr | Asp | Phe | Gly |  |
| 375 |  |  |  |  | 380 |  |  |  |  | 385 |  |  |  |  |  |  |

| ttc | tgt | gcc | cag | atc | acc | cct | gag | cag | agc | aaa | cgc | agt | acc | atg | gtc | 1254 |
|---|---|---|---|---|---|---|---|---|---|---|---|---|---|---|---|---|
| Phe | Cys | Ala | Gln | Ile | Thr | Pro | Glu | Gln | Ser | Lys | Arg | Ser | Thr | Met | Val |  |
| 390 |  |  |  |  | 395 |  |  |  |  | 400 |  |  |  |  | 405 |  |

| gga | acg | cca | tac | tgg | atg | gca | cca | gag | gtg | gtt | aca | cgg | aaa | gct | tat | 1302 |
|---|---|---|---|---|---|---|---|---|---|---|---|---|---|---|---|---|
| Gly | Thr | Pro | Tyr | Trp | Met | Ala | Pro | Glu | Val | Val | Thr | Arg | Lys | Ala | Tyr |  |
|  |  |  |  | 410 |  |  |  |  | 415 |  |  |  |  | 420 |  |  |

| ggc | cct | aaa | gtc | gac | ata | tgg | tct | ctg | ggt | atc | atg | gct | att | gag | atg | 1350 |
|---|---|---|---|---|---|---|---|---|---|---|---|---|---|---|---|---|
| Gly | Pro | Lys | Val | Asp | Ile | Trp | Ser | Leu | Gly | Ile | Met | Ala | Ile | Glu | Met |  |
|  |  | 425 |  |  |  |  | 430 |  |  |  |  | 435 |  |  |  |  |

| gta | gaa | gga | gag | cct | cca | tac | ctc | aat | gaa | aat | ccc | ttg | agg | gcc | ttg | 1398 |
|---|---|---|---|---|---|---|---|---|---|---|---|---|---|---|---|---|
| Val | Glu | Gly | Glu | Pro | Pro | Tyr | Leu | Asn | Glu | Asn | Pro | Leu | Arg | Ala | Leu |  |
|  |  | 440 |  |  |  |  | 445 |  |  |  |  | 450 |  |  |  |  |

| tac | cta | ata | gca | act | aat | gga | acc | cca | gaa | ctt | cag | aat | cca | gag | aaa | 1446 |
|---|---|---|---|---|---|---|---|---|---|---|---|---|---|---|---|---|
| Tyr | Leu | Ile | Ala | Thr | Asn | Gly | Thr | Pro | Glu | Leu | Gln | Asn | Pro | Glu | Lys |  |
| 455 |  |  |  |  | 460 |  |  |  |  | 465 |  |  |  |  |  |  |

| ctt | tcc | cca | ata | ttt | cgg | gat | ttc | tta | aat | cga | tgt | ttg | gaa | atg | gat | 1494 |
|---|---|---|---|---|---|---|---|---|---|---|---|---|---|---|---|---|
| Leu | Ser | Pro | Ile | Phe | Arg | Asp | Phe | Leu | Asn | Arg | Cys | Leu | Glu | Met | Asp |  |
| 470 |  |  |  |  | 475 |  |  |  |  | 480 |  |  |  |  | 485 |  |

| gtg | gaa | aaa | agg | ggt | tca | gcc | aaa | gaa | tta | tta | cag | cat | cct | ttc | ctg | 1542 |
|---|---|---|---|---|---|---|---|---|---|---|---|---|---|---|---|---|
| Val | Glu | Lys | Arg | Gly | Ser | Ala | Lys | Glu | Leu | Leu | Gln | His | Pro | Phe | Leu |  |
|  |  |  | 490 |  |  |  |  | 495 |  |  |  |  | 500 |  |  |  |

| aaa | ctg | gcc | aaa | ccg | tta | tct | agc | ttg | aca | cca | ctg | atc | atg | gca | gct | 1590 |
|---|---|---|---|---|---|---|---|---|---|---|---|---|---|---|---|---|
| Lys | Leu | Ala | Lys | Pro | Leu | Ser | Ser | Leu | Thr | Pro | Leu | Ile | Met | Ala | Ala |  |
|  |  |  | 505 |  |  |  |  | 510 |  |  |  |  | 515 |  |  |  |

| aaa | gaa | gca | atg | aag | agt | aac | cgt | taa | catcactgct | gtgggctcat | 1637 |
|---|---|---|---|---|---|---|---|---|---|---|---|
| Lys | Glu | Ala | Met | Lys | Ser | Asn | Arg |  |  |  |  |
| 520 |  |  |  |  | 525 |  |  |  |  |  |  | actctttttt ccattttcta caagaagcct tttagtatat gaaatgatg actctgttgg    1697 gggtttaaag aaatggtctg cataacctga atgaagaag gaaatgacta ttctctgaag    1757

-continued

```
acaaccaaga gaaaattgga aaagacaagg tatgactttg ttatgaaccc ctgcttttag      1817
gggtccagga agggatttgt gggacttgaa ttcactaggc ttaggtcttt caggaaacag      1877
gctatcaggg gcatttatca tgtgtgagat tggattctac ttgggtgatt tggtggatag      1937
acccatgaat ggcccctggg ggttttcaat cttggattgg aggtgggggt ttcagagtgt      1997
tgccacgtct agctcctctc cc                                               2019
```

<210> SEQ ID NO 2
<211> LENGTH: 525
<212> TYPE: PRT
<213> ORGANISM: Homo sapiens
<223> OTHER INFORMATION: p21 (CDKN1A)-activated kinase 2 (PAK2)

<400> SEQUENCE: 2

```
Met Ser Asp Asn Gly Glu Leu Glu Asp Lys Pro Pro Ala Pro Pro Val
  1               5                  10                  15

Arg Met Ser Ser Thr Ile Phe Ser Thr Gly Gly Lys Asp Pro Leu Ser
                 20                  25                  30

Ala Asn His Ser Leu Lys Pro Leu Pro Ser Val Pro Glu Glu Lys Lys
             35                  40                  45

Pro Arg His Lys Ile Ile Ser Ile Phe Ser Gly Thr Glu Lys Gly Ser
         50                  55                  60

Lys Lys Lys Glu Lys Glu Arg Pro Glu Ile Ser Pro Pro Ser Asp Phe
 65                  70                  75                  80

Glu His Thr Ile His Val Gly Phe Asp Ala Val Thr Gly Glu Phe Thr
                 85                  90                  95

Gly Met Pro Glu Gln Trp Ala Arg Leu Leu Gln Thr Ser Asn Ile Thr
            100                 105                 110

Lys Leu Glu Gln Lys Lys Asn Pro Gln Ala Val Leu Asp Val Leu Lys
        115                 120                 125

Phe Tyr Asp Ser Asn Thr Val Lys Gln Lys Tyr Leu Ser Phe Thr Pro
    130                 135                 140

Pro Glu Lys Asp Gly Leu Pro Ser Gly Thr Pro Ala Leu Asn Ala Lys
145                 150                 155                 160

Gly Thr Glu Ala Pro Ala Val Val Thr Glu Glu Asp Asp Asp Glu
                165                 170                 175

Glu Thr Ala Pro Pro Val Ile Ala Pro Arg Pro Asp His Thr Lys Ser
            180                 185                 190

Ile Tyr Thr Arg Ser Val Ile Asp Pro Val Pro Ala Pro Val Gly Asp
        195                 200                 205

Ser His Val Asp Gly Ala Ala Lys Ser Leu Asp Lys Gln Lys Lys Lys
    210                 215                 220

Pro Lys Met Thr Asp Glu Glu Ile Met Glu Lys Leu Arg Thr Ile Val
225                 230                 235                 240

Ser Ile Gly Asp Pro Lys Lys Lys Tyr Thr Arg Tyr Glu Lys Ile Gly
                245                 250                 255

Gln Gly Ala Ser Gly Thr Val Phe Thr Ala Thr Asp Val Ala Leu Gly
            260                 265                 270

Gln Glu Val Ala Ile Lys Gln Ile Asn Leu Gln Lys Gln Pro Lys Lys
        275                 280                 285

Glu Leu Ile Ile Asn Glu Ile Leu Val Met Lys Glu Leu Lys Asn Pro
    290                 295                 300

Asn Ile Val Asn Phe Leu Asp Ser Tyr Leu Val Gly Asp Glu Leu Phe
305                 310                 315                 320
```

-continued

```
Val Val Met Glu Tyr Leu Ala Gly Gly Ser Leu Thr Asp Val Val Thr
                325                 330                 335

Glu Thr Ala Cys Met Asp Glu Ala Gln Ile Ala Ala Val Cys Arg Glu
            340                 345                 350

Cys Leu Gln Ala Leu Glu Phe Leu His Ala Asn Gln Val Ile His Arg
        355                 360                 365

Asp Ile Lys Ser Asp Asn Val Leu Leu Gly Met Glu Gly Ser Val Lys
    370                 375                 380

Leu Thr Asp Phe Gly Phe Cys Ala Gln Ile Thr Pro Glu Gln Ser Lys
385                 390                 395                 400

Arg Ser Thr Met Val Gly Thr Pro Tyr Trp Met Ala Pro Glu Val Val
                405                 410                 415

Thr Arg Lys Ala Tyr Gly Pro Lys Val Asp Ile Trp Ser Leu Gly Ile
            420                 425                 430

Met Ala Ile Glu Met Val Glu Gly Glu Pro Pro Tyr Leu Asn Glu Asn
        435                 440                 445

Pro Leu Arg Ala Leu Tyr Leu Ile Ala Thr Asn Gly Thr Pro Glu Leu
    450                 455                 460

Gln Asn Pro Glu Lys Leu Ser Pro Ile Phe Arg Asp Phe Leu Asn Arg
465                 470                 475                 480

Cys Leu Glu Met Asp Val Glu Lys Arg Gly Ser Ala Lys Glu Leu Leu
                485                 490                 495

Gln His Pro Phe Leu Lys Leu Ala Lys Pro Leu Ser Ser Leu Thr Pro
            500                 505                 510

Leu Ile Met Ala Ala Lys Glu Ala Met Lys Ser Asn Arg
        515                 520                 525

<210> SEQ ID NO 3
<211> LENGTH: 372
<212> TYPE: DNA
<213> ORGANISM: Artificial Sequence
<220> FEATURE:
<223> OTHER INFORMATION: Description of Artificial Sequence:PAK2deltaS,
      PAK2 hit 1

<400> SEQUENCE: 3
cttgcccggg gccatttcat aattctgaat catgtctgat aacggagaac tggaagataa      60
gcctccagca cctcctgtgc gaatgagcag caccatcttt agcactggag gcaaagaccc     120
tttgtcagcc aatcacagtt tgaaaccttt gccctctgtt ccagaagaga aaaagcccag     180
gcataaaatc atctccatat tctcaggcac agagaaagga agtaaaaaga agaaaaagga     240
acggccagaa atttctcctc catctgattt tgagcacacc atccatgttg gctttgatgc     300
tgttactgga gaattcactg gcatgccaga acagtgggct cgattactac agacctccaa     360
tatcaccaaa ct                                                         372

<210> SEQ ID NO 4
<211> LENGTH: 711
<212> TYPE: DNA
<213> ORGANISM: Artificial Sequence
<220> FEATURE:
<223> OTHER INFORMATION: Description of Artificial Sequence:PAK2deltaL,
      PAK2 Hit 2

<400> SEQUENCE: 4
gaccttggct tgcccggggc catttcataa ttctgaatca tgtctgataa cggagaactg      60
gaagataagc ctccagcacc tcctgtgcga atgagcagca ccatctttag cactggaggc     120
```

-continued

| | |
|---|---|
| aaagacccctt tgtcagccaa tcacagtttg aaaccctttgc cctctgttcc agaagagaaa | 180 |
| aagcccaggc ataaaatcat ctccatattc tcaggcacag agaaaggaag taaaaagaaa | 240 |
| gaaaaggaac ggccagaaat ttctcctcca tctgattttg agcacaccat ccatgttggc | 300 |
| tttgatgctg ttactggaga attcactggc atgccagaac agtgggctcg attactacag | 360 |
| acctccaata tcaccaaact agagcaaaag aagaatcctc aggctgtgct ggatgtccta | 420 |
| aagttctacg actccaacac agtgaagcag aaatatctga gctttactcc tcctgagaaa | 480 |
| gatggccttc cttctggaac gccagcactg aatgccaagg aacagaagc acccgcagta | 540 |
| gtgacagagg aggaggatga tgatgaagag actgctcctc ccgttattgc cccgcgaccg | 600 |
| gatcatacga aatcaattta cacacggtct gtaattgacc ctgttcctgc accagttggt | 660 |
| gattcacatg ttgatggtgc tgccaagtct ttagacaaac agaaaaagaa g | 711 |

<210> SEQ ID NO 5
<211> LENGTH: 545
<212> TYPE: PRT
<213> ORGANISM: Homo sapiens
<220> FEATURE:
<223> OTHER INFORMATION: p21/Cdc42/Rac1-activated kinase 1 (PAK1)

<400> SEQUENCE: 5

```
Met Ser Asn Asn Gly Leu Asp Ile Gln Asp Lys Pro Pro Ala Pro Pro
  1               5                  10                  15

Met Arg Asn Thr Ser Thr Met Ile Gly Val Gly Ser Lys Asp Ala Gly
             20                  25                  30

Thr Leu Asn His Gly Ser Lys Pro Leu Pro Pro Asn Pro Glu Glu Lys
         35                  40                  45

Lys Lys Lys Asp Arg Phe Tyr Arg Ser Ile Leu Pro Gly Asp Lys Thr
     50                  55                  60

Asn Lys Lys Lys Glu Lys Glu Arg Pro Glu Ile Ser Leu Pro Ser Asp
 65                  70                  75                  80

Phe Glu His Thr Ile His Val Gly Phe Asp Ala Val Thr Gly Glu Phe
                 85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Val Ile Ala Pro
            180                 185                 190

Arg Pro Glu His Thr Lys Ser Val Tyr Thr Arg Ser Val Ile Glu Pro
        195                 200                 205

Leu Pro Val Thr Pro Thr Arg Asp Val Ala Thr Ser Pro Ile Ser Pro
    210                 215                 220

Thr Glu Asn Asn Thr Thr Pro Pro Asp Ala Leu Thr Arg Asn Thr Glu
225                 230                 235                 240

Lys Gln Lys Lys Lys Pro Lys Met Ser Asp Glu Glu Ile Leu Glu Lys
                245                 250                 255

Leu Arg Ser Ile Val Ser Val Gly Asp Pro Lys Lys Lys Tyr Thr Arg
```

-continued

```
                260                 265                 270
Phe Glu Lys Ile Gly Gln Gly Ala Ser Gly Thr Val Tyr Thr Ala Met
        275                 280                 285
Asp Val Ala Thr Gly Gln Glu Val Ala Ile Lys Gln Met Asn Leu Gln
        290                 295                 300
Gln Gln Pro Lys Lys Glu Leu Ile Ile Asn Glu Ile Leu Val Met Arg
305                 310                 315                 320
Glu Asn Lys Asn Pro Asn Ile Val Asn Tyr Leu Asp Ser Tyr Leu Val
                325                 330                 335
Gly Asp Glu Leu Trp Val Val Met Glu Tyr Leu Ala Gly Gly Ser Leu
        340                 345                 350
Thr Asp Val Val Thr Glu Thr Cys Met Asp Glu Gly Gln Ile Ala Ala
        355                 360                 365
Val Cys Arg Glu Cys Leu Gln Ala Leu Glu Phe Leu His Ser Asn Gln
    370                 375                 380
Val Ile His Arg Asp Ile Lys Ser Asp Asn Ile Leu Leu Gly Met Asp
385                 390                 395                 400
Gly Ser Val Lys Leu Thr Asp Phe Gly Phe Cys Ala Gln Ile Thr Pro
                405                 410                 415
Glu Gln Ser Lys Arg Ser Thr Met Val Gly Thr Pro Tyr Trp Met Ala
                420                 425                 430
Pro Glu Val Val Thr Arg Lys Ala Tyr Gly Pro Lys Val Asp Ile Trp
        435                 440                 445
Ser Leu Gly Ile Met Ala Ile Glu Met Ile Glu Gly Glu Pro Pro Tyr
    450                 455                 460
Leu Asn Glu Asn Pro Leu Arg Ala Leu Tyr Leu Ile Ala Thr Asn Gly
465                 470                 475                 480
Thr Pro Glu Leu Gln Asn Pro Glu Lys Leu Ser Ala Ile Phe Arg Asp
                485                 490                 495
Phe Leu Asn Arg Cys Leu Asp Met Asp Val Glu Lys Arg Gly Ser Ala
                500                 505                 510
Lys Glu Leu Leu Gln His Gln Phe Leu Lys Ile Ala Lys Pro Leu Ser
        515                 520                 525
Ser Leu Thr Pro Leu Ile Ala Ala Ala Lys Glu Ala Thr Lys Asn Asn
    530                 535                 540
His
545
```

<210> SEQ ID NO 6
<211> LENGTH: 544
<212> TYPE: PRT
<213> ORGANISM: Homo sapiens
<220> FEATURE:
<223> OTHER INFORMATION: p21 (CDKN1A)-activated kinase 3 (PAK3)

<400> SEQUENCE: 6

```
Met Ser Asp Gly Leu Asp Asn Glu Glu Lys Pro Pro Ala Pro Pro Leu
1               5                   10                  15
Arg Met Asn Ser Asn Asn Arg Asp Ser Ser Ala Leu Asn His Ser Ser
            20                  25                  30
Lys Pro Leu Pro Met Ala Pro Glu Glu Lys Asn Lys Lys Ala Arg Leu
        35                  40                  45
Arg Ser Ile Phe Pro Gly Gly Gly Asp Lys Thr Asn Lys Lys Lys Glu
    50                  55                  60
Lys Glu Arg Pro Glu Ile Ser Leu Pro Ser Asp Phe Glu His Thr Ile
```

-continued

```
             65                  70                  75                  80
His Val Gly Phe Asp Ala Val Thr Gly Glu Phe Thr Gly Ile Pro Glu
                 85                  90                  95
Gln Trp Ala Arg Leu Leu Gln Thr Ser Asn Ile Thr Lys Leu Glu Gln
            100                 105                 110
Lys Lys Asn Pro Gln Ala Val Leu Asp Val Lys Phe Tyr Asp Ser
            115                 120                 125
Lys Glu Thr Val Asn Asn Gln Lys Tyr Met Ser Phe Thr Ser Gly Asp
            130                 135                 140
Lys Ser Ala His Gly Tyr Ile Ala Ala His Pro Ser Ser Thr Lys Thr
145                 150                 155                 160
Ala Ser Glu Pro Pro Leu Ala Pro Val Ser Glu Glu Asp Glu
                165                 170                 175
Glu Glu Glu Glu Glu Glu Asp Glu Asn Glu Pro Pro Val Ile Ala
            180                 185                 190
Pro Arg Pro Glu His Thr Lys Ser Ile Tyr Thr Arg Ser Val Val Glu
            195                 200                 205
Ser Ile Ala Ser Pro Ala Val Pro Asn Lys Glu Val Thr Pro Pro Ser
210                 215                 220
Ala Glu Asn Ala Asn Ser Ser Thr Leu Tyr Arg Asn Thr Asp Arg Gln
225                 230                 235                 240
Arg Lys Lys Ser Lys Met Thr Asp Glu Glu Ile Leu Glu Lys Leu Arg
                245                 250                 255
Ser Ile Val Ser Val Gly Asp Pro Lys Lys Lys Tyr Thr Arg Phe Glu
            260                 265                 270
Lys Ile Gly Gln Gly Ala Ser Gly Thr Val Tyr Thr Ala Leu Asp Ile
            275                 280                 285
Ala Thr Gly Gln Glu Val Ala Ile Lys Gln Met Asn Leu Gln Gln Gln
            290                 295                 300
Pro Lys Lys Glu Leu Ile Ile Asn Glu Ile Leu Val Met Arg Glu Asn
305                 310                 315                 320
Lys Asn Pro Asn Ile Val Asn Tyr Leu Asp Ser Tyr Leu Val Gly Asp
                325                 330                 335
Glu Leu Trp Val Val Met Glu Tyr Leu Ala Gly Gly Ser Leu Thr Asp
            340                 345                 350
Val Val Thr Glu Thr Cys Met Asp Glu Gly Gln Ile Ala Ala Val Cys
            355                 360                 365
Arg Glu Cys Leu Gln Ala Leu Asp Phe Leu His Ser Asn Gln Val Ile
            370                 375                 380
His Arg Asp Ile Lys Ser Asp Asn Ile Leu Leu Gly Met Asp Gly Ser
385                 390                 395                 400
Val Lys Leu Thr Asp Phe Gly Phe Cys Ala Gln Ile Thr Pro Glu Gln
                405                 410                 415
Ser Lys Arg Ser Thr Met Val Gly Thr Pro Tyr Trp Met Ala Pro Glu
            420                 425                 430
Val Val Thr Arg Lys Ala Tyr Gly Pro Lys Val Asp Ile Trp Ser Leu
            435                 440                 445
Gly Ile Met Ala Ile Glu Met Val Glu Gly Glu Pro Pro Tyr Leu Asn
450                 455                 460
Glu Asn Pro Leu Arg Ala Leu Tyr Leu Ile Ala Thr Asn Gly Thr Pro
465                 470                 475                 480
Glu Leu Gln Asn Pro Glu Arg Leu Ser Ala Val Phe Arg Asp Phe Leu
                485                 490                 495
```

Asn Arg Cys Leu Glu Met Asp Val Asp Arg Arg Gly Ser Ala Lys Glu
            500                 505                 510

Leu Leu Gln His Pro Phe Leu Lys Leu Ala Lys Pro Leu Ser Ser Leu
        515                 520                 525

Thr Pro Leu Ile Ile Ala Ala Lys Glu Ala Ile Lys Asn Ser Ser Arg
    530                 535                 540

<210> SEQ ID NO 7
<211> LENGTH: 137
<212> TYPE: DNA
<213> ORGANISM: Artificial Sequence
<220> FEATURE:
<223> OTHER INFORMATION: Description of Artificial Sequence:
      PAK2-NM002577 ORF sequence

<400> SEQUENCE: 7
gggaatggaa ggatctgtta agctcactga ctttggtttc tgtgcccaga tcacccctga      60
gcagagcaaa cgcagtacca tggtcggaac gccatactgg atggcaccag aggtggttac     120
acggaaagct tatggcc                                                    137

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:PAK2/Forward

<400> SEQUENCE: 8
gaatggaagg atctgttaag ctcact                                           26

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:PAK2/Probe

<400> SEQUENCE: 9
tcacccctga gcagagcaaa cgc                                              23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:PAK2/Reverse

<400> SEQUENCE: 10
ggttacacgg aaagcttatg gc                                               22

<210> SEQ ID NO 11
<211> LENGTH: 137
<212> TYPE: DNA
<213> ORGANISM: Artificial Sequence
<220> FEATURE:
<223> OTHER INFORMATION: Description of Artificial Sequence:PAK1
      ORF-NM_002576 sequence

<400> SEQUENCE: 11
gggaatggat ggctctgtca agctaactga ctttggattc tgtgcacaga taaccccaga      60
gcagagcaaa cggagcacca tggtaggaac cccatactgg atggcaccag aggttgtgac     120
acgaaaggcc tatgggc                                                    137

<210> SEQ ID NO 12
<211> LENGTH: 137
<212> TYPE: DNA
<213> ORGANISM: Artificial Sequence
<220> FEATURE:
<223> OTHER INFORMATION: Description of Artificial Sequence:Fragment
      base #1,335 of 1,648

<400> SEQUENCE: 12
gggaatggaa ggatctgtta agctcactga ctttggwttc tgtgcmcaga tcacccctga      60
gcagagcaaa cgcagyacca tggtmggaac sccatactgg atggcaccag aggtggttac     120
acggaaagct tatggcc                                                    137

<210> SEQ ID NO 13
<211> LENGTH: 91
<212> TYPE: DNA
<213> ORGANISM: Artificial Sequence
<220> FEATURE:
<223> OTHER INFORMATION: Description of Artificial Sequence:PAK1
      w/UTR-NM_002576 sequence

<400> SEQUENCE: 13
ccttccccct tggactctca ttccctttc cacggagccc cgcgctttcg tgagccccct      60
cgaggaacct ggtctccgca tccagttacc a                                    91

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:PAK1/Forward

<400> SEQUENCE: 14
ttggactctc attccctttt cc                                              22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:PAK1/Probe

<400> SEQUENCE: 15
ccccgcgctt tcgtgagcc                                                  19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:PAK1/Reverse

<400> SEQUENCE: 16
acctggtctc cgcatcca                                                   18

<210> SEQ ID NO 17
<211> LENGTH: 82
<212> TYPE: PRT
<213> ORGANISM: Artificial Sequence
<220> FEATURE:
<223> OTHER INFORMATION: Description of Artificial Sequence:PAK1 kinase
      inhibitory segment

<400> SEQUENCE: 17

```
Glu Arg Pro Glu Ile Ser Leu Pro Ser Asp Phe Glu His Thr Ile His
 1               5                  10                  15

Val Gly Phe Asp Ala Val Thr Gly Glu Phe Thr Gly Met Pro Glu Gln
             20                  25                  30

Trp Ala Arg Leu Leu Gln Thr Ser Asn Ile Thr Lys Ser Glu Gln Lys
         35                  40                  45

Lys Asn Pro Gln Ala Val Leu Asp Val Leu Glu Phe Tyr Asn Ser Lys
     50                  55                  60

Lys Thr Ser Asn Ser Gln Lys Tyr Met Ser Phe Thr Asp Lys Ser Ala
 65                  70                  75                  80

Glu Asp

<210> SEQ ID NO 18
<211> LENGTH: 80
<212> TYPE: PRT
<213> ORGANISM: Artificial Sequence
<220> FEATURE:
<223> OTHER INFORMATION: Description of Artificial Sequence:PAK2 kinase
      inhibitory segment

<400> SEQUENCE: 18

Glu Arg Pro Glu Ile Ser Pro Pro Ser Asp Phe Glu His Thr Ile His
 1               5                  10                  15

Val Gly Phe Asp Ala Val Thr Gly Glu Phe Thr Gly Met Pro Glu Gln
             20                  25                  30

Trp Ala Arg Leu Leu Gln Thr Ser Asn Ile Thr Lys Leu Glu Gln Lys
         35                  40                  45

Lys Asn Pro Gln Ala Val Leu Asp Val Leu Lys Phe Tyr Asp Ser Asn
     50                  55                  60

Thr Val Lys Gln Lys Tyr Leu Ser Phe Thr Pro Pro Glu Lys Asp Gly
 65                  70                  75                  80

<210> SEQ ID NO 19
<211> LENGTH: 200
<212> TYPE: PRT
<213> ORGANISM: Artificial Sequence
<220> FEATURE:
<223> OTHER INFORMATION: Description of Artificial Sequence:poly Gly tag
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 19

Gly Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
             85                  90                  95
```

```
Gly Gly Gly Gly Gly Gly Gly Gly Gly Gly Gly Gly Gly Gly Gly
            100             105             110
Gly Gly Gly Gly Gly Gly Gly Gly Gly Gly Gly Gly Gly Gly Gly
        115             120             125
Gly Gly Gly Gly Gly Gly Gly Gly Gly Gly Gly Gly Gly Gly Gly
    130             135             140
Gly Gly Gly Gly Gly Gly Gly Gly Gly Gly Gly Gly Gly Gly Gly
145             150             155             160
Gly Gly Gly Gly Gly Gly Gly Gly Gly Gly Gly Gly Gly Gly Gly
            165             170             175
Gly Gly Gly Gly Gly Gly Gly Gly Gly Gly Gly Gly Gly Gly Gly
        180             185             190
Gly Gly Gly Gly Gly Gly Gly Gly
        195             200
```